United States Patent
Abe et al.

(10) Patent No.: US 9,130,244 B2
(45) Date of Patent: Sep. 8, 2015

(54) NONAQUEOUS ELECTROLYTE SOLUTION AND ELECTROCHEMICAL ELEMENT USING SAME

(75) Inventors: Koji Abe, Ube (JP); Shoji Shikita, Ube (JP); Kazuyuki Kawabe, Ube (JP); Masahide Kondo, Ube (JP); Tatsuo Fujino, Ube (JP)

(73) Assignee: UBE INDUSTRIES, LTD., Ube-shi (JP)

( * ) Notice: Subject to any disclaimer, the term of this patent is extended or adjusted under 35 U.S.C. 154(b) by 739 days.

(21) Appl. No.: 13/395,660

(22) PCT Filed: Sep. 14, 2010

(86) PCT No.: PCT/JP2010/065877
§ 371 (c)(1),
(2), (4) Date: Mar. 13, 2012

(87) PCT Pub. No.: WO2011/034067
PCT Pub. Date: Mar. 24, 2011

(65) Prior Publication Data
US 2012/0171581 A1    Jul. 5, 2012

(30) Foreign Application Priority Data

| Sep. 15, 2009 | (JP) | 2009-212808 |
| Sep. 15, 2009 | (JP) | 2009-213088 |
| Feb. 18, 2010 | (JP) | 2010-033891 |
| Mar. 30, 2010 | (JP) | 2010-076730 |
| Mar. 30, 2010 | (JP) | 2010-076731 |
| Mar. 30, 2010 | (JP) | 2010-078916 |
| Jun. 22, 2010 | (JP) | 2010-142085 |

(51) Int. Cl.
| H01M 10/0567 | (2010.01) |
| H01M 6/16 | (2006.01) |
| C07F 7/18 | (2006.01) |
| H01M 10/052 | (2010.01) |
| H01M 10/0569 | (2010.01) |
| H01M 10/0566 | (2010.01) |

(52) U.S. Cl.
CPC ......... H01M 10/0567 (2013.01); C07F 7/1852 (2013.01); H01M 6/168 (2013.01); H01M 10/052 (2013.01); H01M 10/0569 (2013.01); H01M 10/0566 (2013.01); H01M 2300/0017 (2013.01); Y02E 60/122 (2013.01); Y02T 10/7011 (2013.01)

(58) Field of Classification Search
CPC ............ H01M 6/168; H01M 10/0567; H01M 10/0566; H01M 10/1569; H01M 2300/0017; H01M 10/052; Y02E 60/122; Y02E 60/12; Y02T 10/7011
See application file for complete search history.

(56) References Cited

U.S. PATENT DOCUMENTS

| 2004/0035715 A1 | 2/2004 | Putter et al. |
| 2008/0102377 A1 | 5/2008 | Abe et al. |
| 2009/0309060 A1 | 12/2009 | Oka et al. |
| 2010/0035147 A1 | 2/2010 | Kotato et al. |

FOREIGN PATENT DOCUMENTS

| EP | 1 650 826 | 4/2006 |
| JP | 2002 367673 | 12/2002 |
| JP | 2002 367674 | 12/2002 |
| JP | 2003 059529 | 2/2003 |
| JP | 2004-514786 A | 5/2004 |
| JP | 2007-39737 A | 2/2007 |
| JP | 2008 146930 | 6/2008 |
| JP | 2008-176046 A | 7/2008 |
| JP | 2008 262908 | 10/2008 |
| JP | 2009-164053 A | 7/2009 |
| WO | 2006 070546 | 7/2006 |
| WO | 2008 001955 | 1/2008 |
| WO | WO 2008/133112 A1 | 11/2008 |
| WO | 2009 113545 | 9/2009 |

OTHER PUBLICATIONS

Japanese Office Action issued Jul. 22, 2014 in Patent Application No. 2011-531937.
Office Action issued Dec. 16, 2014 in Japanese Patent Application No. 2011-531937.
International Search Report Issued Dec. 21, 2010 in PCT/JP10/65877 Filed Sep. 14, 2010.
European Search Report issued Jul. 7, 2015, in corresponding European Patent Application No. 15 16 1857.

*Primary Examiner* — Laura Weiner
(74) *Attorney, Agent, or Firm* — Oblon, McClelland, Maier & Neustadt, L.L.P.

(57) ABSTRACT

A nonaqueous electrolytic solution of an electrolyte salt dissolved in a nonaqueous solvent, which contains a carboxylate represented by the following general formula (8) in an amount of from 0.01 to 5% by mass of the nonaqueous electrolytic solution:

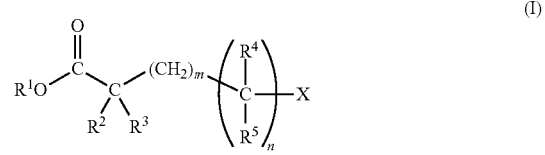

(I)

wherein $X^{31}$ represents $-A^2-C{\equiv}Y^2$, $-A^2-C({=}O)O-A^3-C{\equiv}Y^2$ or $-A^2-C({=}O)O-A^4$; $A^1$, $A^2$ and $A^3$ each independently represent an alkylene group having from 1 to 6 carbon atoms; $A^4$ represents an alkyl group having from 1 to 6 carbon atoms; $Y^1$ and $Y^2$ each independently represent CH or N.

9 Claims, No Drawings

NONAQUEOUS ELECTROLYTE SOLUTION AND ELECTROCHEMICAL ELEMENT USING SAME

TECHNICAL FIELD

The present invention relates to a nonaqueous electrolytic solution capable of improving electrochemical characteristics, and to an electrochemical element using it.

BACKGROUND ART

In recent years, electrochemical elements, especially lithium secondary batteries have been widely used as power supplies for small-sized electronic devices such as mobile telephones, notebook-size personal computers and the like, power supplies for electric vehicles, as well as for electric power storage. These electronic devices and vehicles may be used in a broad temperature range, for example, at midsummer high temperatures or at frigid low temperatures, and are therefore required to be improved in point of the discharge capacity in a broad temperature range even after long-term use.

In this specification, the term of lithium secondary battery is used as a concept including so-called lithium ion secondary batteries.

The lithium secondary battery is mainly constituted of a positive electrode and a negative electrode containing a material capable of absorbing and releasing lithium, and a nonaqueous electrolytic solution containing a lithium salt and a nonaqueous solvent. For the nonaqueous solvent, used are carbonates such as ethylene carbonate (EC), propylene carbonate (PC), etc.

As the negative electrode, known are metal lithium, and metal compounds (metal elemental substances, oxides, alloys with lithium, etc.) and carbon materials capable of absorbing and releasing lithium. In particular, a lithium secondary battery using a carbon material capable of absorbing and releasing lithium, such as coke, artificial graphite, natural graphite or the like, has been widely put into practical use.

For example, it is known that, in a lithium secondary battery using a highly-crystalline carbon material such as natural graphite, artificial graphite or the like as the negative electrode material therein, the decomposed product or gas generated through reductive decomposition of the solvent in the nonaqueous electrolytic solution on the surface of the negative electrode during charging detracts from the electrochemical reaction favorable for the battery, therefore worsening the cycle properties of the battery. Deposition of the decomposed product of the nonaqueous solvent interferes with smooth absorption and release of lithium by the negative electrode, and therefore, in particular, the cycle properties at low temperatures and at high temperatures may be thereby often worsened.

In addition, it is known that a lithium secondary battery using a lithium metal or its alloy, or a metal elemental substance such as tin, silicon or the like or its metal oxide as the negative electrode material therein may have a high initial battery capacity but its battery performance such as battery capacity and cycle properties greatly worsens, since the micronized powdering of the material is promoted during cycles thereby bringing about accelerated reductive decomposition of the nonaqueous solvent, as compared with the negative electrode of a carbon material. In addition, the micronized powdering of the negative electrode material and the deposition of the decomposed product of the nonaqueous solvent may interfere with smooth absorption and release of lithium by the negative electrode, and therefore, in particular, the cycle properties at low temperatures and at high temperatures may be thereby often worsened.

On the other hand, it is known that, in a lithium secondary battery using, for example, $LiCoO_2$, $LiMn_2O_4$, $LiNiO_2$, $LiFePO_4$ or the like as the positive electrode, when the nonaqueous solvent in the nonaqueous electrolytic solution is heated at a high temperature in the charged state, the decomposed product or the gas thereby locally generated through partial oxidative decomposition in the interface between the positive electrode material and the nonaqueous electrolytic solution interferes with the electrochemical reaction favorable for the battery, and therefore the battery performance such as cycle properties and others are thereby also worsened.

As in the above, the decomposed product and the gas generated through decomposition of the nonaqueous electrolytic solution on the positive electrode or the negative electrode may interfere with the movement of lithium ions or may swell the battery, and the battery performance is thereby worsened. Despite the situation, electronic appliances equipped with lithium secondary batteries therein are offering more and more an increasing range of functions and are being in a stream of further increase in the power consumption. With that, the capacity of lithium secondary batteries is being much increased, and the space volume for the nonaqueous electrolytic solution in the battery is decreased by increasing the density of the electrode and by reducing the useless space volume in the battery. Accordingly, the situation is that even decomposition of only a small amount of the nonaqueous electrolytic solution may worsen the battery performance at low temperatures and at high temperatures.

Patent Reference 1 discloses a lithium ion secondary battery that comprises a positive electrode containing a lithium manganese oxide having a spinel structure, a negative electrode containing a carbon material and an organic electrolytic solution, wherein the organic electrolytic solution contains a malonic diester in an amount of from 0.5 to 3.0%, saying that the cycle properties of the battery at 25° C. are thereby enhanced.

Patent Reference 2 discloses an electrolytic solution with a silyl carboxylate such as trimethylsilyl trimethylsilyloxyacetate or the like added thereto. This shows that the hydroxy acid derivative compound of that type in which both the hydrogen atoms of the hydroxyl group and the carboxyl group of the hydroxy acid each are substituted with an alkylsilyl group forms a "tough modified" SEI film (surface film) on the carbon electrode surface of the anode (negative electrode), thereby enhancing the cycle properties of the battery having a silicon thin film as the negative electrode.

Patent Reference 3 discloses a lithium ion secondary battery in which an oxygen-containing aliphatic compound having an alkynyl group and/or an alkynylene group with no active hydrogen is added to the nonaqueous electrolytic solution, saying that the cycle properties at 20° C. and 60° C. of the battery can be improved.

Patent Reference 4 discloses an electrolytic solution containing a dialkyl ester compound such as dimethyl succinate in an amount of from 10 to 30% by volume in a nonaqueous solvent, showing excellent high-temperature storage properties and cycle properties.

As a lithium primary battery, for example, known is one in which the positive electrode is formed of manganese dioxide or fluorographite and the negative electrode is formed of lithium metal, and the lithium primary battery of the type is widely used as having a high energy density, for which, however, it is desired to prevent the increase in the internal resistance during long term storage and to enhance the discharge load characteristic at high temperatures and at low temperatures.

Recently, further, as a novel power source for electric vehicles or hybrid electric vehicles, electric storage devices have been developed, for example, an electric double layer capacitor using activated carbon or the like as the electrode from the viewpoint of the output density thereof, and a hybrid capacitor including a combination of the electric storage principle of a lithium ion secondary battery and that of an electric double layer capacitor (an asymmetric capacitor where both the capacity by lithium absorption and release and the electric double layer capacity are utilized) from the viewpoint of both the energy density and the output density thereof; and it is desired to improve the properties such as the cycle properties at high temperatures and at low temperatures of these capacitors.

[Patent Reference 1] JP-A 2000-223153
[Patent Reference 2] JP-A 2006-351535
[Patent Reference 3] JP-A 2001-256995
[Patent Reference 4] JP-A 7-272756

DISCLOSURE OF THE INVENTION

Problems that the Invention is to Solve

An object of the present invention is to provide a nonaqueous electrolytic solution capable of improving electrochemical characteristics in a broad temperature range such as low-temperature and high-temperature cycle properties as well as low-temperature load characteristics after high-temperature charging storage, and to provide an electrochemical element using the nonaqueous electrolytic solution.

Means for Solving the Problems

The present inventors have investigated in detail the performance of the nonaqueous electrolytic solution in the above-mentioned prior art. As a result, the actual situation is that the nonaqueous electrolytic solution in the Patent Reference 1 could not obtain good cycle properties in a broad range of low temperatures and high temperatures.

Given the situation, the present inventors have assiduously studied for the purpose of solving the above-mentioned problems, and have found that, in a nonaqueous electrolytic solution of an electrolyte salt dissolved in a nonaqueous solvent, when a hydroxy acid derivative compound where two different substituents, of which one is a substituent (—CO$_2$R) selected from an alkyloxycarbonyl group, an alkenyloxycarbonyl group and an alkynyloxycarbonyl group and the other is a substituent selected from a sulfonyloxy group (—OSO$_2$R), an acyloxy group (—OC(=O)R), an alkyloxycarbonyloxy group, an alkenyloxycarbonyloxy group, an alkynyloxycarbonyloxy group (—OC(=O)OR), a formyloxy group (—OCHO), a dialkylphosphoryl group (—OP(=O)R$_2$), an alkyl(alkoxy)phosphoryl group (—OP(=O)(OR)R') and a dialkoxyphosphoryl group (—OP(=O)(OR')$_2$), are bonded to each other via a hydrocarbon group therebetween is added to the nonaqueous electrolytic solution, then the low-temperature and high-temperature cycle properties can be improved (relative to the first nonaqueous electrolytic solution mentioned below).

The nonaqueous electrolytic solution that contains, as added thereto, a compound where the both hydrogen atoms of the hydroxyl group and the carboxyl groups of the hydroxy acid each are substituted with an alkylsilyl group, such as trimethylsilyl trimethylsilyloxyacetate in the Patent Reference 2, has a problem in that a surface film having a high resistance is formed on the negative electrode, and therefore the low-temperature properties after high-temperature cycles may rather worsen.

Consequently, the present inventors have found that, in a nonaqueous electrolytic solution of an electrolyte salt dissolved in a nonaqueous solvent, when a hydroxy acid derivative compound where the hydrogen atom of any one only of the hydroxyl group and the carboxyl group of the hydroxy acid is substituted with an alkylsilyloxy group is added to the nonaqueous electrolytic solution, then the high-temperature cycle properties and the low-temperature properties after high-temperature cycles can be improved (relative to the second nonaqueous electrolytic solution mentioned below).

The nonaqueous electrolytic solution of the Patent Reference 3 could not exhibit any remarkable effect for low-temperature cycle properties.

With that, the present inventors added a compound, which has a carbon-carbon triple bond (ethynyl group) or a carbon-nitrogen triple bond (cyano group) in the alcohol moiety of the ester group of a carboxylate and has any of an ester, ethynyl or cyano group at the carbonyl carbon of the carboxylate via an alkylene group therebetween, to a nonaqueous electrolytic solution, and have found that the low-temperature cycle properties can be improved (relative to the third nonaqueous electrolytic solution mentioned below).

The nonaqueous electrolytic solution in the Patent Reference 4 could not exhibit any remarkable effect for the low-temperature load characteristics after high-temperature charging storage.

With that, the present inventors added a compound, which has at least two carboxylate moieties and additionally has a specific functional group completely differing from the carboxylate, in the linking group that links these two functional groups, to a nonaqueous electrolytic solution of an electrolyte salt dissolved in an nonaqueous solvent, and have found that the low-temperature load characteristics after high-temperature charging storage can be improved (relative to the fourth nonaqueous electrolytic solution mentioned below).

Specifically, the present invention provides the following (1) to (9):

(1) A nonaqueous electrolytic solution of an electrolyte dissolved in a nonaqueous solvent, which contains a carboxylate represented by the following general formula (I) in an amount of from 0.01 to 10% by mass of the nonaqueous electrolytic solution:

[Chemical Formula 1]

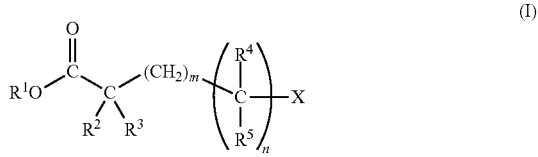

(In the formula, R$^1$ represents an alkyl group having from 1 to 6 carbon atoms, an alkenyl group having from 2 to 7 carbon atoms, an alkynyl group having from 3 to 8 carbon atoms, a cycloalkyl group having from 3 to 8 carbon atoms, or a cyanoalkyl group having from 2 to 7 carbon atoms; R$^2$ represents a hydrogen atom, an alkoxy group having from 1 to 6 carbon atoms, a formyloxy group, an acyloxy group having from 2 to 7 carbon atoms, an alkoxycarbonyloxy group having from 2 to 7 carbon atoms, an alkanesulfonyloxy group having from 1 to 6 carbon atoms, an arylsulfonyloxy group having from 6 to 12 carbon atoms, an alkylsilyloxy group having from 3 to 18 carbon atoms, a dialkylphosphoryloxy group having from 2 to 12 carbon atoms, an alkoxy(alkyl)phosphoryloxy group having from 2 to 12 carbon atoms, a dialkoxyphosphoryloxy group having from 2 to 12 carbon atoms; $R^3$ represents a hydrogen atom, —$CH_2COOR^6$ or an alkyl group having from 1 to 6 carbon atoms; $R^4$ represents a hydrogen atom or an alkyl group having from 1 to 6 carbon atoms; $R^5$ has the same meaning as $R^2$, or represents a hydrogen atom, an alkyl group having from 1 to 6 carbon atoms or —$CH_2COOR^7$; $R^6$ and $R^7$ each independently represent an alkyl group having from 1 to 6 carbon atoms, an alkenyl group having from 2 to 7 carbon atoms, an alkynyl group having from 3 to 8 carbon atoms, or a cycloalkyl group having from 3 to 8 carbon atoms; X represents —$OR^8$, -$A^2$-C≡$Y^2$, -$A^2$-C(=O)O-$A^3$-C≡$Y^2$, -$A^2$-C(=O)O-$A^4$ or $COOR^1$; $R^8$ is the same as $R^1$; $A^1$ to $A^3$ each independently represent an alkylene group having from 1 to 6 carbon atoms; $A^4$ represents an alkyl group having from 1 to 6 carbon atoms; $Y^2$ represents CH or N; m indicates an integer of from 0 to 4; n indicates 0 or 1; at least one of the hydrogen atoms on the carbon atoms of $R^1$ to $R^6$, independently of each other, may be substituted with a halogen atom, an alkoxy group having from 1 to 4 carbon atoms, or a nitrile group.)

(2) A nonaqueous electrolytic solution of an electrolyte dissolved in a nonaqueous solvent, which contains at least one hydroxy acid derivative compound represented by the following general formula (I-I) in an amount of from 0.01 to 10% by mass of the nonaqueous electrolytic solution (hereinafter this may be referred to as "first nonaqueous electrolytic solution"):

[Chemical Formula 2]

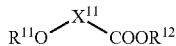

(I-I)

(In the formula, $X^{11}$ represents —$CR^{13}R^{14}$—$(CH_2)_n$—, or represents the following general formula (I-II)).

[Chemical Formula 3]

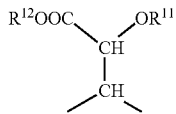

(I-II)

(In the formula, $R^{11}$ represents a sulfonyl group (—$SO_2R^{15}$, in which $R^{15}$ represents an alkyl group having from 1 to 6 carbon atoms, an alkyl group having from 1 to 6 carbon atoms in which at least one hydrogen atom is substituted with a halogen atom, or an aryl group having from 6 to 12 carbon atoms), an acyl group having from 2 to 6 carbon atoms, an alkyloxycarbonyl group having from 2 to 7 carbon atoms, an alkenyloxycarbonyl group having from 3 to 7 carbon atoms, an alkynyloxycarbonyl group having from 4 to 7 carbon atoms, a formyl group (—CHO), a dialkylphosphoryl group having from 2 to 16 carbon atoms, an alkyl(alkoxy)phosphoryl group having from 2 to 16 carbon atoms, or a dialkoxyphosphoryl group having from 2 to 16 carbon atoms; $R^{12}$ represents an alkyl group having from 1 to 6 carbon atoms, an alkenyl group having from 2 to 6 carbon atoms, or an alkynyl group having from 3 to 6 carbon atoms; $R^{13}$ and $R^{14}$ each represent a hydrogen atom or an alkyl group having from 1 to 6 carbon atoms; n indicates an integer of from 0 to 3; at least one hydrogen atom on the carbon atoms of $R^2$ may be substituted with a halogen atom, an alkoxy group having from 1 to 4 carbon atoms, or a nitrile group.)

(3) A nonaqueous electrolytic solution of an electrolyte dissolved in a nonaqueous solvent, which contains at least one hydroxy acid derivative compound represented by the following general formula (II-I) in an amount of from 0.01 to 10% by mass of the nonaqueous electrolytic solution (hereinafter this may be referred to as "second nonaqueous electrolytic solution"):

[Chemical Formula 4]

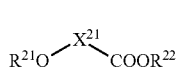

(II-I)

(In the formula, $X^{21}$ represents —$CR^{23}R^{24}$—$(CH_2)_n$—, or represents the following general formula (II-II).)

[Chemical Formula 5]

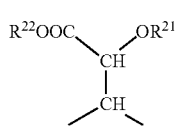

(II-II)

(In the formula, $R^{21}$ represents an alkylsilyl group having from 3 to 12 carbon atoms, an alkyl group having from 1 to 6 carbon atoms, an alkenyl group having from 2 to 6 carbon atoms, an alkynyl group having from 3 to 6 carbon atoms, an alkanesulfonyl group having from 1 to 6 carbon atoms, an arylsulfonyl group having from 6 to 12 carbon atoms, an acyl group having from 2 to 6 carbon atoms, an alkoxycarbonyl group having from 2 to 6 carbon atoms, an alkenyloxycarbonyl group having from 3 to 7 carbon atoms, an alkynyloxycarbonyl group having from 4 to 7 carbon atoms, a formyl group, a dialkylphosphoryl group having from 2 to 16 carbon atoms, an alkyl(alkoxy)phosphoryl group having from 2 to 16 carbon atoms, or a dialkoxyphosphoryl group having from 2 to 16 carbon atoms; when $R^{21}$ is an alkylsilyl group, then $R^{22}$ is an alkyl group having from 1 to 6 carbon atoms, an alkenyl group having from 2 to 6 carbon atoms, or an alkynyl group having from to 6 carbon atoms; when $R^{21}$ is an alkyl group having from 1 to 6 carbon atoms, an alkenyl group having from 2 to 6 carbon atoms, an alkynyl group having from 3 to 6 carbon atoms, an alkanesulfonyl group having from 1 to 6 carbon atoms, an acyl group having from 2 to 6 carbon atoms, an alkoxycarbonyl group having from 2 to 6 carbon atoms, an alkenyloxycarbonyl group having from 3 to 7 carbon atoms, an alkynyloxycarbonyl group having from 4 to 7 carbon atoms, a formyl group, a dialkylphosphoryl group having from 2 to 16 carbon atoms, an alkyl(alkoxy)phosphoryl group having from 2 to 16 carbon atoms, or a dialkoxyphosphoryl group having from 2 to 16 carbon atoms, then $R^{22}$ is an alkylsilyl group having from 3 to 12 carbon atoms; $R^{23}$ and $R^{24}$ each represent a hydrogen atom or an alkyl group having from 1 to 6 carbon atoms; n indicates an integer of from 0 to 3; at least one hydrogen atom on the carbon atoms of $R^{22}$ may be substituted with a halogen atom, an alkoxy group having from 1 to 4 carbon atoms, or a nitrile group.)

(4) A hydroxy acid derivative compound represented by the following general formula (II-III) (hereinafter this may be referred to as "second compound"):

[Chemical Formula 6]

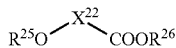
(II-III)

(In the formula, $X^{22}$ represents $-CR^{27}R^{28}-(CH_2)_n-$, or represents the following general formula (II-IV).)

[Chemical Formula 7]

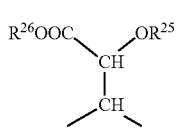
(II-IV)

(In the formula, $R^{25}$ represents an alkylsilyl group having from 3 to 12 carbon atoms, an alkyl group having from 1 to 6 carbon atoms, an alkenyl group having from 2 to 6 carbon atoms, an alkynyl group having from 3 to 6 carbon atoms, an alkanesulfonyl group having from 1 to 6 carbon atoms, an acyl group having from 2 to 6 carbon atoms, an alkoxycarbonyl group having from 2 to 6 carbon atoms, an alkenyloxycarbonyl group having from 3 to 7 carbon atoms, an alkynyloxycarbonyl group having from 4 to 7 carbon atoms, a formyl group, a dialkylphosphoryl group having from 2 to 16 carbon atoms, an alkyl(alkoxy)phosphoryl group having from 2 to 16 carbon atoms, or a dialkoxyphosphoryl group having from 2 to 16 carbon atoms; when $R^{25}$ is an alkylsilyl group, then $R^{26}$ is an alkenyl group having from 2 to 6 carbon atoms, or an alkynyl group having from 3 to 6 carbon atoms; when $R^{25}$ is an alkenyl group having from 2 to 6 carbon atoms, an alkynyl group having from 3 to 6 carbon atoms, an alkanesulfonyl group having from 1 to 6 carbon atoms, an alkoxycarbonyl group having from 2 to 6 carbon atoms, an alkenyloxycarbonyl group having from 3 to 7 carbon atoms, an alkynyloxycarbonyl group having from 4 to 7 carbon atoms, a formyl group, a dialkylphosphoryl group having from 2 to carbon atoms, an alkyl(alkoxy)phosphoryl group having from 2 to 16 carbon atoms, or a dialkoxyphosphoryl group having from 2 to 16 carbon atoms, then $R^{26}$ is an alkylsilyl group having from 3 to 12 carbon atoms; $R^{27}$ and $R^{28}$ each represent a hydrogen atom or an alkyl group having from 1 to 6 carbon atoms; n indicates an integer of from 0 to 3; at least one hydrogen atom on the carbon atoms of $R^{26}$ may be substituted with a halogen atom, an alkoxy group having from 1 to 4 carbon atoms, or a nitrile group; provided that when $R^{25}$ is an alkenyl group, then n=0, and when $R^{26}$ is an alkenyl group, then $R^{25}$ is a trimethylsilyl group.)

(5) A nonaqueous electrolytic solution of an electrolyte salt dissolved in a nonaqueous solvent, which contains a carboxylate represented by the following general formula (III-I) in an amount of from 0.01 to 5% by mass of the nonaqueous electrolytic solution (hereinafter this may be referred to as "third nonaqueous electrolytic solution"):

[Chemical Formula 8]

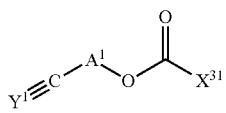
(III-I)

(In the formula, $X^{31}$ represents $-A^2-C\equiv Y^2$, $-A^2-C(\!=\!O)O-A^3-C\equiv Y^2$ or $-A^2-C(\!=\!O)O-A^4$; $A^1$, $A^2$ and $A^3$ each independently represent an alkylene group having from 1 to 6 carbon atoms; $A^4$ represents an alkyl group having from 1 to 6 carbon atoms; $Y^1$ and $Y^2$ each independently represent CH or N.)

(6) A carboxylate compound represented by the following general formula (III-II) (hereinafter this may be referred to as "third compound").

[Chemical Formula 9]

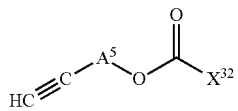
(III-II)

(In the formula, $X^{32}$ represents $-A^6-C\equiv N$ or $A^7-C(\!=\!O)O-A^8-C\equiv N$; $A^5$, $A^7$ and $A^8$ each independently represent an alkylene group having from 1 to 6 carbon atoms; $A^6$ represents an alkylene group having from 2 to 6 carbon atoms.)

(7) A nonaqueous electrolytic solution of an electrolyte salt dissolved in a nonaqueous solvent, which contains a carboxylate represented by the following general formula (IV-I) in an amount of from 0.01 to 10% by mass of the nonaqueous electrolytic solution (hereinafter this may be referred to as "fourth nonaqueous electrolytic solution"):

[Chemical Formula 10]

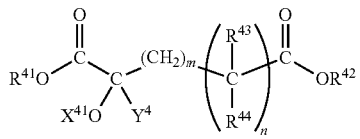
(IV-I)

(In the formula, $R^{41}$ and $R^{42}$ each independently represent an alkyl group having from 1 to 6 carbon atoms, an alkenyl group having from 2 to 7 carbon atoms, an alkynyl group having from 3 to 8 carbon atoms, or a cycloalkyl group having from 3 to 8 carbon atoms; $R^{43}$ represents a hydrogen atom, or an alkyl group having from 1 to 6 carbon atoms; $R^{44}$ represents a hydrogen atom, an alkyl group having from 1 to 6 carbon atoms, or $CH_2COOR^{45}$; $X^{41}$ represents an alkyl group having from 1 to 6 carbon atoms, a formyl group, an acyl group having from 2 to 7 carbon atoms, an alkoxycarbonyl group having from 2 to 7 carbon atoms, an alkanesulfonyl group having from 1 to 6 carbon atoms, an aryl group having from 6 to 12 carbon atoms, an alkylsilyl group having from 3 to 18 carbon atoms, a dialkylphosphoryl group having from 2 to 12 carbon atoms, an alkoxy(alkyl)phosphoryl group having from 2 to 12 carbon atoms, or a dialkoxyphosphoryl group having from 2 to 12 carbon atoms; $Y^4$ represents a hydrogen atom, $-CH_2COOR^{46}$ or an alkyl group having from 1 to 6 carbon atoms; $R^{45}$ and $R^{46}$ each independently represent an alkyl group having from 1 to 6 carbon atoms, an alkenyl group having from 2 to 7 carbon atoms, an alkynyl group having from 3 to 8 carbon atoms, a cycloalkyl group having from 3 to 8 carbon atoms; m indicates an integer of from 0 to 4; n indicates 0 or 1; at least one hydrogen atom on the carbon atoms of $R^{41}$, $R^{42}$, $R^{45}$ and $R^{46}$ may be substituted with a halogen atom, an alkoxy group having from 1 to 4 carbon atoms, or a nitrile group.)

(8) A carboxylate compound represented by the following general formula (IV-II) (hereinafter referred to as "fourth compound"):

[Chemical Formula 11]

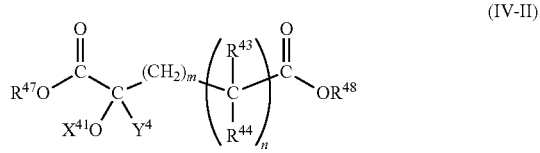

(IV-II)

(In the formula, $R^{47}$ and $R^{48}$ each independently represent an alkynyl group having from 3 to 8 carbon atoms; $R^{43}$, $R^{44}$, $X^{41}$, $Y^4$, m and n have the same meanings as above.)

(9) An electrochemical element comprising a positive electrode, a negative electrode, and a nonaqueous electrolytic solution of an electrolyte salt dissolved in a nonaqueous solvent, wherein the nonaqueous electrolytic solution contains a carboxylate represented by any of the above-mentioned general formulae (I) in an amount of from 0.01 to 10% by mass of the nonaqueous electrolytic solution.

Advantage of the Invention

According to the present invention, there are provided a nonaqueous electrolytic solution capable of improving low-temperature and high-temperature cycle properties, and an electrochemical element using the nonaqueous electrolytic solution.

Also according to the present invention, there are provided a nonaqueous electrolytic solution capable of improving high-temperature cycle properties and low-temperature properties after high-temperature cycles, and an electrochemical element using the nonaqueous electrolytic solution, as well as a hydroxy acid derivative compound and a carboxylate compound useful as intermediate materials for medicines, agricultural chemicals, electronic materials, polymer materials and others, or as battery materials.

Also according to the present invention, there are provided a nonaqueous electrolytic solution capable of improving low-temperature load characteristics after high-temperature charging storage, and an electrochemical element using the nonaqueous electrolytic solution.

BEST MODE FOR CARRYING OUT THE INVENTION

[Nonaqueous Electrolytic Solution]

The nonaqueous electrolytic solution of the present invention comprises an electrolyte dissolved in a nonaqueous solvent, and contains a carboxylate represented by any of the following general formula (I) in an amount of from 0.01 to 10% by mass of the nonaqueous electrolytic solution.

[Chemical Formula 12]

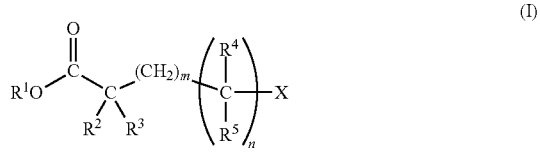

(I)

(In the formula, $R^1$ represents an alkyl group having from 1 to 6 carbon atoms, an alkenyl group having from 2 to 7 carbon atoms, an alkynyl group having from 3 to 8 carbon atoms, a cycloalkyl group having from 3 to 8 carbon atoms, or a cyanoalkyl group having from 2 to 7 carbon atoms; $R^2$ represents a hydrogen atom, an alkoxy group having from 1 to 6 carbon atoms, a formyloxy group, an acyloxy group having from 2 to 7 carbon atoms, an alkoxycarbonyloxy group having from 2 to 7 carbon atoms, an alkanesulfonyloxy group having from 1 to 6 carbon atoms, an arylsulfonyloxy group having from 6 to 12 carbon atoms, an alkylsilyloxy group having from 3 to 18 carbon atoms, a dialkylphosphoryloxy group having from 2 to 12 carbon atoms, an alkoxy(alkyl)phosphoryloxy group having from 2 to 12 carbon atoms, a dialkoxyphosphoryloxy group having from 2 to 12 carbon atoms; $R^3$ represents a hydrogen atom, —$CH_2COOR^6$, or an alkyl group having from 1 to 6 carbon atoms; $R^4$ represents a hydrogen atom or an alkyl group having from 1 to 6 carbon atoms; $R^5$ has the same meaning as $R^2$, or represents a hydrogen atom, an alkyl group having from 1 to 6 carbon atoms or —$CH_2COOR^7$; $R^6$ and $R^7$ each independently represent an alkyl group having from 1 to 6 carbon atoms, an alkenyl group having from 2 to 7 carbon atoms, an alkynyl group having from 3 to 8 carbon atoms, or a cycloalkyl group having from 3 to 8 carbon atoms; X represents —$OR^8$, -$A^2$-C≡$Y^2$, -$A^2$-C(=O)O-$A^3$-C≡$Y^2$, -$A^2$-C(=O)O-$A^4$ or $COOR^1$; $R^8$ is the same as $R^1$; $A^1$ to $A^3$ each independently represent an alkylene group having from 1 to 6 carbon atoms; $A^4$ represents an alkyl group having from 1 to 6 carbon atoms; $Y^2$ represents CH or N; m indicates an integer of from 0 to 4; n indicates 0 or 1; at least one of the hydrogen atoms on the carbon atoms of $R^1$ to $R^6$, independently of each other, may be substituted with a halogen atom, an alkoxy group having from 1 to 4 carbon atoms, or a nitrile group.)

More concretely, the nonaqueous electrolytic solution of the present invention includes the first nonaqueous electrolytic solution to the fourth nonaqueous electrolytic solution.

[The First Nonaqueous Electrolytic Solution]

The first nonaqueous electrolytic solution of the present invention comprises an electrolyte dissolved in a nonaqueous solvent and contains at least one hydroxy acid derivative compound represented by the following general formula (I-I) in an amount of from 0.01 to 10% by mass of the nonaqueous electrolytic solution.

[Chemical Formula 13]

(I-I)

(In the formula, $X^{11}$ represents —$CR^{13}R^{14}$—$(CH_2)_n$—, or represents the following general formula (I-II)).

[Chemical Formula 14]

(I-II)

(In the formula, $R^{11}$ represents a sulfonyl group (—$SO_2R^{15}$, in which $R^{15}$ represents an alkyl group having from 1 to 6 carbon atoms, an alkyl group having from 1 to 6 carbon atoms in which at least one hydrogen atom is substituted with a halogen atom, or an aryl group having from 6 to 12 carbon atoms), an acyl group having from 2 to 6 carbon atoms, an alkyloxycarbonyl group having from 2 to 7 carbon atoms, an alkenyloxycarbonyl group having from 3 to 7 carbon atoms, an alkynyloxycarbonyl group having from 4 to 7 carbon atoms, a formyl group (—CHO), a dialkylphosphoryl group having from 2 to 16 carbon atoms, an alkyl(alkoxy)phosphoryl group having from 2 to 16 carbon atoms, or a dialkoxyphosphoryl group having from 2 to 16 carbon atoms; $R^{12}$ represents an alkyl group having from 1 to 6 carbon atoms, an alkenyl group having from 2 to 6 carbon atoms, or an alkynyl group having from 3 to 6 carbon atoms; $R^{13}$ and $R^{14}$ each represent a hydrogen atom or an alkyl group having from 1 to 6 carbon atoms; n indicates an integer of from 0 to 3; at least one hydrogen atom on the carbon atoms of $R^2$ may be substituted with a halogen atom, an alkoxy group having from 1 to 4 carbon atoms, or a nitrile group.)

The first nonaqueous electrolytic solution containing, as added thereto, the hydroxy acid derivative compound represented by the general formula (I-I) can improve low-temperature and high-temperature cycle properties. Though not always clear, the reason may be considered as follows:

Specifically, it has been known that the hydroxy acid derivative compound represented by the general formula (I-II) has one reduction potential quite different from that of a compound having the same substituent at both ends of the hydrocarbon group therein, since in the former, two different substituents, of which one is a substituent (—$CO_2R$) selected from an alkyloxycarbonyl group, an alkenyloxycarbonyl group and an alkynyloxycarbonyl group and the other is a substituent selected from a sulfonyloxy group (—$OSO_2R$), an acyloxy group (—OC(=O)R), an alkyloxycarbonyloxy group, an alkenyloxycarbonyloxy group, an alkynyloxycarbonyloxy group (—OC(=O)OR), a formyloxy group (—OCHO), a dialkylphosphoryl group (—OP(=O)$R_2$), an alkyl(alkoxy)phosphoryl group (—OP(=O)(OR)R') and a dialkoxyphosphoryl group (—OP(=O)(OR')$_2$), are bonded to each other via a hydrocarbon group therebetween. This is because a mixture surface film derived from the two different substituents of the hydroxy acid derivative compound represented by the general formula (I-I) is formed on the electrode, and therefore, the mixture surface film formed at a reduction potential that could not be anticipated in the case where a compound having the same substituent of an alkoxycarbonyl group at both ends of the hydrocarbon group therein, like the malonic diester described in the Patent Reference 1, is used could exhibit the characteristic effect of improving low-temperature and high-temperature cycle properties.

In the general formula (I-I), the linear or branched acyl group having from 2 to 6 carbon atoms of $R^{11}$ includes an acetyl group, a propionyl group, a butyryl group, an isobutyryl group, a pivaloyl group, etc. Of those, preferred are an acetyl group and a propionyl group; and more preferred is an acetyl group.

The linear or branched alkyloxycarbonyl group having from 2 to 7 carbon atoms of $R^{11}$ includes a methoxycarbonyl group, an ethoxycarbonyl group, a propoxycarbonyl group, an isopropoxycarbonyl group, a butoxycarbonyl group. Of those preferred are a methoxycarbonyl group and an ethoxycarbonyl group; and more preferred is a methoxycarbonyl group.

The linear or branched alkenyloxycarbonyl group having from 3 to 7 carbon atoms of $R^{11}$ includes a vinyloxycarbonyl group, a 2-propenyloxycarbonyl group, a 2-butenyloxycarbonyl group, a 3-butenyloxycarbonyl group, a 4-pentenyloxycarbonyl group, a 2-methyl-2-propenyloxycarbonyl group, a 2-methyl-2-butenyloxycarbonyl group, a 3-methyl-2-butenyloxycarbonyl group. Of those, preferred are a vinyloxycarbonyl group and a 2-propenyloxycarbonyl group; and more preferred is a 2-propenyloxycarbonyl group.

The linear or branched alkynyloxycarbonyl group having from 4 to 7 carbon atoms of $R^{11}$ includes a 2-propynyloxycarbonyl group, a 2-butynyloxycarbonyl group, a 3-butynyloxycarbonyl group, a 4-pentynyloxycarbonyl group, a 5-hexynyloxycarbonyl group, a 1-methyl-2-propynyloxycarbonyl group, a 1-methyl-2-butynyloxycarbonyl group, a 1,1-dimethyl-2-propynyloxycarbonyl group, etc. Of those, preferred are a 2-propynyloxycarbonyl group and a 1-methyl-2-propynyloyxcarbonyl group; and more preferred is a 2-propynyloxycarbonyl group.

In the general formula (I-I), the linear or branched dialkylphosphoryl group having from 2 to 16 carbon atoms of $R^{11}$ is preferably a dimethylphosphoryl group, a diethylphosphoryl group, a dipropylphosphoryl group, or a dibutylphosphoryl group. Of those, more preferred are a dimethylphosphoryl group and a diethylphosphoryl group.

The linear or branched alkyl(alkoxy)phosphoryl group having from 2 to 16 carbon atoms of $R^{11}$ is preferably a methoxy(methyl)phosphoryl group, an ethoxy(ethyl)phosphoryl group, a propyl(propyloxy)phosphoryl group, a dibutoxy(butyl)phosphoryl group, an ethoxy(methyl)phosphoryl group, or an ethyl(methoxy)phosphoryl group. Of those, more preferred are a methoxy(methyl)phosphoryl group and an ethoxy(ethyl)phosphoryl group.

The linear or branched dialkoxyphosphoryl having from 2 to 16 carbon atoms of $R^{11}$ is preferably a dimethoxyphosphoryl group, a diethoxyphosphoryl group, a dipropoxyphosphoryl group, or a dibutoxyphosphoryl group.

Of those, more preferred are a dimethoxyphosphoryl group and a diethoxyphosphoryl group.

In the general formula (I-I) where the substituent $R^{11}$ is a sulfonyl group (—$SO_2R^{15}$), the linear or branched alkyl group having from 1 to 6 carbon atoms of the substituent $R^{15}$ includes a methyl group, an ethyl group, a propyl group, a butyl group, a pentyl group, a hexyl group, a 2-propyl group, etc.

The linear or branched alkyl group having from 1 to 6 carbon atoms of $R^{15}$ in which at least one hydrogen atom is substituted with a halogen atom includes the above-mentioned linear or branched alkyl group in which at least one hydrogen atom is substituted with a halogen atom; and its specific examples include a trifluoromethyl group, and a 2,2,2-trifluoroethyl group.

Of those, preferred are a methyl group, an ethyl group and a trifluoromethyl group; and most preferred is a methyl group.

The aryl group having from 6 to 12 carbon atoms of the substituent $R^{15}$ includes a phenyl group, a tolyl group, a mesityl group, etc.

The aryl group having from 6 to 12 carbon atoms of $R^{15}$ in which at least one hydrogen atom is substituted with a halogen atom includes the above-mentioned aryl group in which at least one hydrogen atom is substituted with a halogen atom; and its specific examples include a 4-fluorophenyl group and a 4-trifluoromethylphenyl group.

Of those, preferred are a phenyl group and a tolyl group; and most preferred is a tolyl group.

The substituent $R^{11}$ is more preferably a sulfonyl group (—$SO_2R^{15}$), a linear or branched alkoxycarbonyl group having from 2 to 6 carbon atoms, a formyl group, or a dialkoxyphosphoryl group, even more preferably a sulfonyl group (—$SO_2R^{15}$) or a formyl group, and most preferably a sulfonyl group (—$SO_2R^{15}$). Of those, preferred are a methanesulfonyl group, an ethanesulfonyl group, a benzenesulfonyl group, a 4-methylbenzenesulfonyl group, an acetyl group, a propionyl group, a methoxycarbonyl group, an ethoxycarbonyl group, a formyl group, a dimethylphosphoryl group, a dimethoxyphosphoryl group, and a diethoxyphosphoryl group; more preferred are a methanesulfonyl group, a 4-methylbenzenesulfonyl group, an acetyl group, a methoxycarbonyl group and a formyl group; and most preferred is a methanesulfonyl group.

In the general formula (I-II), the linear or branched alkyl group having from 1 to 6 of the substituent $R^{12}$ includes a methyl group, an ethyl group, a propyl group, a butyl group, a pentyl group, a hexyl group, a 2-propyl group, etc.

The linear or branched alkenyl group having from 2 to 6 carbon atoms of $R^{12}$ includes a vinyl group, a 2-propenyl group, a 2-butenyl group, a 3-butenyl group, a 4-pentenyl group, a 2-methyl-2-propenyl group, a 2-methyl-2-butenyl group, a 3-methyl-2-butenyl group, etc.

The linear or branched alkynyl group having from 3 to 6 carbon atoms of $R^{12}$ includes a 2-propynyl group, a 2-butynyl group, a 3-butynyl group, a 4-pentynyl group, a 5-hexynyl group, a 1-methyl-2-propynyl group, a 1-methyl-2-butynyl group, a 1,1-dimethyl-2-propynyl group, etc.

The above-mentioned group $R^{12}$, in which at least one hydrogen atom on the carbon atom is substituted with a halogen atom, an alkoxy group having from 1 to 4 carbon atoms or a nitrile group, is preferably a 2,2,2-trifluoroethyl group, a 2-methoxyethyl group, a 3-methoxypropyl group, a 2-ethoxyethyl group, a cyanomethyl group, a 2-cyanoethyl group, a 2-cyanopropyl group, etc.

In the general formula (I-I), the substituent $R^{12}$ is more preferably a linear or branched alkenyl group having from 2 to 6 carbon atoms or a linear or branched alkynyl group having from 3 to 6 carbon atoms rather than a linear or branched alkyl group having from 1 to 6 carbon atoms, and most preferably a linear or branched alkynyl group having from 3 to 6 carbon atoms. Of those, preferred are a methyl group, an ethyl group, a vinyl group, a 2-propenyl group and a 2-propynyl group; more preferred are a vinyl group, a 2-propenyl group and a 2-propynyl group; and most preferred is a 2-propynyl group [or that is, a propargyl group].

The halogen atom with which the hydrogen atom on the carbon atom is substituted in $R^{12}$ includes a fluorine atom, a chlorine atom, a bromine atom and an iodine atom. Preferred is a fluorine atom or a chlorine atom; and more preferred is a fluorine atom.

In the general formula (I-I) where $X^{11}$ is $-CR^{13}R^{14}-(CH_2)_n-$, the linear or branched alkyl group having from 1 to 6 carbon atoms of the substituents $R^{13}$ and $R^{14}$ includes a methyl group, an ethyl group, a propyl group, a butyl group, a pentyl group, a hexyl group, a 2-propyl group, etc. Of those, preferred are a methyl group and an ethyl group; and more preferred is a methyl group.

Preferably, at least one of $R^{13}$ and $R^{14}$ is a linear or branched alkyl group having from 1 to 6 carbon atoms (and the other is a hydrogen atom); and more preferably, both of $R^{13}$ and $R^{14}$ are linear or branched alkyl groups each having from 1 to 6 carbon atoms. Above all, preferred are a case where at least one of $R^{13}$ and $R^{14}$ is a methyl group (and the other is a hydrogen atom), and a case where both of $R^{13}$ and $R^{14}$ are methyl groups. In the general formula (I-I) where $X^{11}$ is $-CR^{13}R^{14}-(CH_2)_n-$, n is an integer of from 0 to 3, but most preferably n=0.

In the general formula (I-I), in case where $X^{11}$ is $-CR^{13}R^{14}-(CH_2)_n-$, in which $R^{13}$ and $R^{14}$ are different substituents, and $X^{11}$ is the general formula (I-II), the formula includes optical isomers. The optical isomers include R-form and S-form, both of which exhibit the effect of the present invention. The optical isomers may be in the form of a mixture thereof in a desired ratio; and both a case where one optical isomer is excessive over the other (optical active form) and a case where the two optical isomers exist in the same amount (racemic form) exhibit the effect of the present invention.

Further, in the general formula (I-I), in case where $X^{11}$ is the general formula (I-II), the formula has two asymmetric carbons, or that is, the formula further includes diastereomers in addition to the above-mentioned optical isomers. The diastereomers are not always the same in point of the chemical property or the electrochemical property thereof; and therefore, depending on the ratio of the diastereomers, the degree of the effect of the present invention may vary; however, any case where any of the optical isomers is used either singly or in the form of a mixture thereof can exhibit the effect of the present invention.

The compounds of the general formula (I-I) where the substituents fall within the above-mentioned range are preferred as more effective for improving battery characteristics such as low-temperature and high-temperature cycle properties, etc.

Not specifically defined, the hydroxy acid derivative compounds represented by the general formula (I-I) where $X^{11}$ is $-CR^{13}R^{14}-(CH_2)_n-$ concretely include the following compounds.

[1] As compounds that may include optical active form (compounds having an asymmetric carbon in the main structure of the hydroxy acid moiety);

there may be mentioned one or more R-forms, S-forms and mixtures of R-form and S-form selected from the following compounds:

(i) methyl 2-(methanesulfonyloxy)propionate, ethyl 2-(methanesulfonyloxy)propionate, vinyl 2-(methanesulfonyloxy)propionate, 2-propenyl 2-(methanesulfonyloxy)propionate, 2-propynyl 2-(methanesulfonyloxy)propionate, 2,2,2-trifluoroethyl 2-(methanesulfonyloxy)propionate, 2-methoxyethyl 2-(methanesulfonyloxy)propionate, cyanomethyl 2-(methanesulfonyloxy)propionate, 2-cyanoethyl 2-(methanesulfonyloxy)propionate, methyl 2-(benzenesulfonyloxy)propionate, 2-propenyl 2-(benzenesulfonyloxy)propionate, 2-propynyl 2-(benzenesulfonyloxy)propionate, methyl 2-(4-methylbenzenesulfonyloxy)propionate, 2-propenyl 2-(4-methylbenzenesulfonyloxy)propionate, 2-propynyl 2-(4-methylbenzenesulfonyloxy)propionate, (ii) methyl 2-(acetyloxy)propionate, ethyl 2-(acetyloxy)propionate, vinyl 2-(acetyloxy)propionate, 2-propenyl 2-(acetyloxy)propionate, 2-propynyl 2-(acetyloxy)propionate, 2,2,2-trifluoroethyl 2-(acetyloxy)propionate, 2-methoxyethyl 2-(acetyloxy)propionate, cyanomethyl 2-(acetyloxy)propionate, 2-cyanoethyl 2-(acetyloxy)propionate, methyl 2-(methoxycarbonyloxy)propionate, ethyl 2-(methoxycarbonyloxy)propionate, vinyl 2-(methoxycarbonyloxy)propionate, 2-propenyl 2-(methoxycarbonyloxy)propionate, 2-propynyl 2-(methoxycarbonyloxy)propionate, 2,2,2-trifluoroethyl 2-(methoxycarbonyloxy)propionate, 2-methoxyethyl 2-(methoxycarbonyloxy)propionate, cyanomethyl 2-(methoxycarbonyloxy)propionate, 2-cyanoethyl 2-(methoxycarbonyloxy)propionate, (iii) methyl 2-(vinyloxycarbonyloxy)propionate, ethyl 2-(vinyloxycarbonyloxy)propionate, vinyl 2-(vinyloxycarbonyloxy)propionate, 2-propenyl 2-(vinyloxycarbonyloxy)propionate, 2-propynyl 2-(vinyloxycarbonyloxy)propionate, (iv) methyl 2-(2-propenyloxycarbonyloxy)propionate, ethyl 2-(2-propenyloxycarbonyloxy)propionate, vinyl 2-(2-propenyloxycarbonyloxy)propionate, 2-propenyl 2-(2-propenyloxycarbonyloxy)propionate, 2-propynyl 2-(2-propenyloxycarbonyloxy)propionate, methyl 2-(2-propynyloxycarbonyloxy)propionate, ethyl 2-(2-propynyloxycarbonyloxy)propionate, vinyl 2-(2-propynyloxycarbonyloxy)propionate, 2-propenyl 2-(2- propynyloxycarbonyloxy)propionate, 2-propynyl 2-(2-propynyloxycarbonyloxy)propionate, 2,2,2-trifluoroethyl 2-(2-propynyloxycarbonyloxy)propionate, 2-methoxyethyl 2-(2-propynyloxycarbonyloxy)propionate, cyanomethyl 2-(2-propynyloxycarbonyloxy)propionate, 2-cyanoethyl 2-(2-propynyloxycarbonyloxy)propionate, (v) methyl 2-(formyloxy)propionate, ethyl 2-(formyloxy)propionate, vinyl 2-(formyloxy)propionate, 2-propenyl 2-(formyloxy)propionate, 2-propynyl 2-(formyloxy)propionate, 2,2,2-trifluoroethyl 2-(formyloxy)propionate, 2-methoxyethyl 2-(formyloxy)propionate, cyanomethyl 2-(formyloxy)propionate, 2-cyanoethyl 2-(formyloxy)propionate, (vi) methyl 2-(dimethylphosphoryloxy)propionate, ethyl 2-(dimethylphosphoryloxy)propionate, vinyl 2-(dimethylphosphoryloxy)propionate, 2-propenyl 2-(dimethylphosphoryloxy)propionate, 2-propynyl 2-(dimethylphosphoryloxy)propionate, methyl 2-(dimethoxyphosphoryloxy)propionate, ethyl 2-(dimethoxyphosphoryloxy)propionate, vinyl 2-(dimethoxyphosphoryloxy)propionate, 2-propenyl 2-(dimethoxyphosphoryloxy)propionate, 2-propynyl 2-(dimethoxyphosphoryloxy)propionate, methyl 2-(diethoxyphosphoryloxy)propionate, ethyl 2-(diethoxyphosphoryloxy)propionate, vinyl 2-(diethoxyphosphoryloxy)propionate, 2-propenyl 2-(diethoxyphosphoryloxy)propionate, 2-propynyl 2-(diethoxyphosphoryloxy)propionate, methyl 2-[methoxy(methyl)phosphoryloxy]propionate, ethyl 2-[methoxy(methyl)phosphoryloxy]propionate, vinyl 2-[methoxy(methyl)phosphoryloxy]propionate, 2-propenyl 2-[methoxy(methyl)phosphoryloxy]propionate, 2-propynyl 2-[methoxy(methyl)phosphoryloxy]propionate, methyl 2-[ethoxy(methyl)phosphoryloxy]propionate, 2-propynyl 2-[ethoxy(methyl)phosphoryloxy]propionate, methyl 2-[ethyl(methoxy)phosphoryloxy]propionate, and 2-propynyl 2-[ethyl(methoxy)phosphoryloxy]propionate.

The following compounds are further mentioned:

[2] As compounds not including optical active form (compounds not having an asymmetric carbon in the main structure of the hydroxy acid moiety);

the following are mentioned:

(i) methyl methanesulfonyloxyacetate, 2-propenyl methanesulfonyloxyacetate, 2-propynyl methane sulfonyloxyacetate, methyl benzenesulfonyloxyacetate, 2-propenyl benzenesulfonyloxyacetate, 2-propynyl benzenesulfonyloxyacetate, methyl 4-methylbenzenesulfonyloxyacetate, 2-propenyl 4-methylbenzenesulfonyloxyacetate, 2-propynyl 4-methylbenzenesulfonyloxyacetate, methyl acetyloxyacetate, 2-propenyl acetyoxyacetate, 2-propynyloxy acetyloxyacetate, methyl methoxycarbonyloxyacetate, 2-propenyl methoxycarbonyoxyacetate, 2-propynyl methoxycarbonyoxyacetate, (ii) methyl 2-propenyloxycarbonyloxyacetate, 2-propenyl 2-propenyloxycarbonyloxyacetate, methyl 2-propynyloxycarbonyloxyacetate, 2-propenyl 2-propynyloxycarbonyloxyacetate, 2-propynyl 2-propynyloxycarbonyloxyacetate, (iii) methyl formyloxyacetate, 2-propenyl formyloxyacetate, 2-propynyl formyloxyacetate, (iv) methyl dimethylphosphoryloxyacetate, 2-propenyl dimethylphosphoryloxyacetate, methyl dimethoxyphosphoryloxyacetate, 2-propenyl dimethoxyphosphoryloxyacetate, 2-propynyl dimethoxyphosphoryloxyacetate, methyl diethoxyphosphoryloxyacetate, 2-propenyl diethoxyphosphoryloxyacetate, 2-propynyl diethoxyphosphoryloxyacetate, methyl methoxy(methyl)phosphoryloxyacetate, 2-propynyl methoxy(methyl)phosphoryloxyacetate, methyl ethoxy(methyl)phosphoryloxyacetate, 2-propynyl ethoxy(methyl)phosphoryloxyacetate, methyl ethyl(methoxy)phosphoryloxyacetate, 2-propynyl ethyl(methoxy)phosphoryloxyacetate, (v) methyl 2-(methanesulfonyloxy)-2-methylpropionate, 2-propenyl 2-(methanesulfonyloxy)-2-methylpropionate, 2-propynyl 2-(methanesulfonyloxy)-2-methylpropionate, methyl 2-(benzenesulfonyloxy)-2-methylpropionate, 2-propenyl 2-(benzenesulfonyloxy)-2-methylpropionate, 2-propynyl 2-(benzenesulfonyloxy)-2-methylpropionate, methyl 2-(4-methylbenzenesulfonyloxy)-2-methylpropionate, 2-propenyl 2-(4-methylbenzenesulfonyloxy)-2-methylpropionate, 2-propynyl 2-(4-methylbenzenesulfonyloxy)-2-methylpropionate, methyl 2-(acetyloxy)-2-methylpropionate, 2-propenyl 2-(acetyloxy)-2-methylpropionate, 2-propynyl 2-(acetyloxy)-2-methylpropionate, (vi) methyl 2-(methoxycarbonyloxy)-2-methylpropionate, 2-propenyl 2-(methoxycarbonyloxy)-2-methylpropionate, 2-propynyl 2-(methoxycarbonyloxy)-2-methylpropionate, methyl 2-methyl-2-(2-propenyloxycarbonyloxy)propionate, 2-propenyl 2-methyl-2-(2-propenyloxycarbonyloxy)propionate, 2-propynyl 2-methyl-2-(2-propenyloxycarbonyloxy)propionate, (vii) methyl 2-methyl-2-(2-propynyloxycarbonyloxy)propionate, 2-propenyl 2-methyl-2-(2-propynyloxycarbonyloxy)propionate, 2-propynyl 2-methyl-2-(2-propynyloxycarbonyloxy)propionate, (viii) methyl 2-(formyloxy)-2-methylpropionate, 2-propenyl 2-(formyloxy)-2-methylpropionate, 2-propynyl 2-(formyloxy)-2-methylpropionate, (ix) methyl 2-(dimethylphosphoryloxy)-2-methylpropionate, 2-propynyl 2-(dimethylphosphoryloxy)-2-methylpropionate, methyl 2-(dimethoxyphosphoryloxy)-2-methylpropionate, 2-propynyl 2-(dimethoxyphosphoryloxy)-2-methylpropionate, methyl 2-(diethoxyphosphoryloxy)-2-methylpropionate, 2-propynyl 2-(diethoxyphosphoryloxy)-2-methylpropionate, methyl 2-[methoxy(methyl)phosphoryloxy]-2-methylpropionate, 2-propynyl 2-[methoxy(methyl)phosphoryloxy]-2-methylpropionate.

Preferred examples of the hydroxy acid derivative compounds represented by the above-mentioned general formula (I-I) where $X^{11}$ is $—CR^{13}R^{14}—(CH_2)_n—$ include methyl 2-(methanesulfonyloxy)propionate, 2-propenyl 2-(methanesulfonyloxy)propionate, 2-propynyl 2-(methanesulfonyloxy)propionate, methyl 2-(benzenesulfonyloxy)propionate, 2-propenyl 2-(benzenesulfonyloxy)propionate, 2-propynyl 2-(benzenesulfonyloxy)propionate, methyl 2-(4-methylbenzenesulfonyloxy)propionate, 2-propenyl 2-(4-methylbenzenesulfonyloxy)propionate, 2-propynyl 2-(4-methylbenzenesulfonyloxy)propionate, methyl 2-(acetyloxy)propionate, 2-propenyl 2-(acetyloxy)propionate, 2-propynyl 2-(acetyloxy)propionate, methyl 2-(methoxycarbonyloxy)propionate, 2-propenyl 2-(methoxycarbonyloxy)propionate, 2-propynyl 2-(methoxycarbonyl)propionate, methyl 2-(2-propyloxycarbonyloxy)propionate, methyl 2-(formyloxy)propionate, 2-propenyl 2-(formyloxy)propionate, 2-propynyl 2-(formyloxy)propionate, 2-propynyl 2-(dimethoxyphosphoryloxy)propionate, 2-propynyl 2-(diethoxyphosphoryloxy)propionate, methyl 2-(methanesulfonyloxy)-2-methylpropionate, 2-propenyl 2-(methanesulfonyloxy)-2-methylpropionate, 2-propynyl 2-(methanesulfonyloxy)-2-methylpropionate, methyl 2-(benzenesulfonyloxy)-2-methylpropionate, 2-propenyl 2-(benzenesulfonyloxy)-2-methylpropionate, 2-propynyl 2-(benzenesulfonyloxy)-2-methylpropionate, methyl 2-(4-methylbenzenesulfonyloxy)-2-methylpropionate, 2-propenyl 2-(4-methylbenzenesulfonyloxy)-2-methylpropionate, 2-propynyl 2-(4-methylbenzenesulfonyloxy)-2-methylpropionate, methyl 2-(acetyloxy)-2-methylpropionate, 2-propenyl 2-(acetyloxy)-2-methylpropionate, 2-propynyl 2-(acetyloxy)-2-methylpropionate, methyl 2-(methoxycarbonyloxy)-2-methylpropionate, 2-propenyl 2-(methoxycarbonyloxy)-2-methylpropionate, 2-propynyl 2-(methoxycarbonyloxy)-2-methylpropionate, methyl 2-methyl-2-(2-propyloxycarbonyloxy)propionate, methyl 2-(formyloxy)-2-methylpropionate, 2-propenyl 2-(formyloxy)-2-methylpropionate, 2-propynyl 2-(formyloxy)-2-methylpropionate, 2-propynyl 2-(dimethoxyphosphoryloxy)-2-methylpropionate, 2-propynyl 2-(diethoxyphosphoryloxy)-2-methylpropionate. More preferred are 2-propynyl 2-(methanesulfonyloxy)propionate, 2-propynyl 2-(benzenesulfonyloxy)propionate, 2-propynyl 2-(4-methylbenzenesulfonyloxy)propionate, 2-propynyl 2-(acetyloxy)propionate, 2-propynyl 2-(methoxycarbonyloxy)propionate, 2-propynyl 2-(formyloxy)propionate, 2-propynyl 2-(diethoxyphosphoryloxy)propionate, 2-propynyl 2-(methanesulfonyloxy)-2-methylpropionate, 2-propynyl 2-(benzenesulfonyloxy)-2-methylpropionate, 2-propynyl 2-(4-methylbenzenesulfonyloxy)-2-methylpropionate, 2-propynyl 2-(acetyloxy)-2-methylpropionate, 2-propynyl 2-(methoxycarbonyloxy)-2-methylpropionate, 2-propynyl 2-(formyloxy)-2-methylpropionate, 2-propynyl 2-(dimethoxyphosphoryloxy)-2-methylpropionate, and 2-propynyl 2-(diethoxyphosphoryloxy)-2-methylpropionate.

Of those, especially preferred are 2-propynyl 2-(methanesulfonyloxy)propionate, 2-propynyl 2-(benzenesulfonyloxy)propionate, 2-propynyl 2-(4-methylbenzenesulfonyloxy)propionate, 2-propynyl 2-(acetyloxy)propionate, 2-propynyl 2-(methoxycarbonyloxy)propionate, 2-propynyl 2-(2-propynyloxycarbonyloxy)propionate, 2-propynyl 2-(formyloxy)propionate, 2-propynyl 2-(dimethoxyphosphoryloxy)propionate, 2-propynyl 2-(diethoxyphosphoryloxy)propionate, methyl 2-(methanesulfonyloxy)propionate, 2-propynyl 2-(methanesulfonyloxy)-2-methylpropionate, 2-propynyl 2-(methoxycarbonyloxy)-2-methylpropionate, and 2-propynyl 2-(formyloxy)-2-methylpropionate.

As the compounds represented by the general formula (I-I) where $X^{11}$ is the general formula (I-II), there may be mentioned (2R,3R) forms, (2S,3S) forms, (2R,3S) forms, (2S,3R) forms and their mixture of one or more selected from the following: dimethyl 2,3-di(methanesulfonyloxy)succinate, diethyl 2,3-di(methanesulfonyloxy)succinate, divinyl 2,3-di(methanesulfonyloxy)succinate, di(2-propenyl) 2,3-di(methanesulfonyloxy)succinate, di(2-propynyl) 2,3-di(methanesulfonyloxy)succinate, di(2,2,2-trifluoroethyl) 2,3-di(methanesulfonyloxy)succinate, di(2-methoxyethyl) 2,3-di(methanesulfonyloxy)succinate, di(cyanomethyl) 2,3-di(methanesulfonyloxy)succinate, di(2-cyanoethyl) 2,3-di(methanesulfonyloxy)succinate, dimethyl 2,3-di(benzenesulfonyloxy)succinate, di(2-propenyl) 2,3-di(benzenesulfonyloxy)succinate, di(2-propynyl) 2,3-di(benzenesulfonyloxy)succinate, dimethyl 2,3-di(4-methylbenzenesulfonyloxy)succinate, di(2-propenyl) 2,3-di(4-methylbenzenesulfonyloxy)succinate, di(2-propynyl) 2,3-di(4-methylbenzenesulfonyloxy)succinate, dimethyl 2,3-di(acetyloxy)succinate, diethyl 2,3-di(acetyloxy)succinate, divinyl 2,3-di(acetyloxy)succinate, di(2-propenyl) 2,3-di(acetyloxy)succinate, di(2-propynyl) 2,3-di(acetyloxy)succinate, dimethyl 2,3-di(methoxycarbonyloxy)succinate, diethyl 2,3-di(methoxycarbonyloxy)succinate, divinyl 2,3-di(methoxycarbonyloxy)succinate, di(2-propenyl) 2,3-di(methoxycarbonyloxy)succinate, di(2-propynyl) 2,3-di(methoxycarbonyloxy)succinate, dimethyl 2,3-di(2-propenyloxycarbonyloxy)succinate, divinyl 2,3-di(2-propenyloxycarbonyloxy)succinate, di(2-propenyl) 2,3-di(2-propenyloxycarbonyloxy)succinate, di(2-propynyl) 2,3-di(2-propenyloxycarbonyloxy)succinate, dimethyl 2,3-di(2-propynyloxycarbonyloxy)succinate, divinyl 2,3-di(2-propynyloxycarbonyloxy)succinate, di(2-propenyl) 2,3-di(2-propynyloxycarbonyloxy)succinate, di(2-propynyl) 2,3-di(2-propynyloxycarbonyloxy)succinate, dimethyl 2,3-di(formyloxy)succinate, diethyl 2,3-di(formyloxy)succinate, divinyl 2,3-di(formyloxy)succinate, di(propenyl) 2,3-di(formyloxy)succinate, di(2-propynyl) 2,3-di(formyloxy)succinate, dimethyl 2,3-di(dimethylphosphoryloxy)succinate, diethyl 2,3-di(dimethylphosphoryloxy)succinate, divinyl 2,3-di(dimethylphosphoryloxy)succinate, di(2-propynyl) 2,3-di(dimethylphosphoryloxy)succinate, dimethyl 2,3-di(dimethoxyphosphoryloxy)succinate, diethyl 2,3-di(dimethoxyphosphoryloxy)succinate, divinyl 2,3-di(dimethoxyphosphoryloxy)succinate, di(2-propynyl) 2,3-di(dimethoxyphosphoryloxy)succinate, dimethyl 2,3-di(diethoxyphosphoryloxy)succinate, diethyl 2,3-di(diethoxyphosphoryloxy)succinate, divinyl 2,3-di(diethoxyphosphoryloxy)succinate, di(2-propynyl) 2,3-di(diethoxyphosphoryloxy)succinate, dimethyl 2,3-di[methoxy(methyl)phosphoryloxy]succinate, diethyl 2,3-di[methoxy(methyl)phosphoryloxy]succinate, divinyl 2,3-di[methoxy(methyl)phosphoryloxy]succinate, di(2-propynyl) 2,3-di[methoxy(methyl)phosphoryloxy]succinate, dimethyl 2,3-di[ethoxy(methyl)phosphoryloxy]succinate, di(2-propynyl) 2,3-di[ethoxy(methyl)phosphoryloxy]succinate, dimethyl 2,3-di[ethyl(methoxy)phosphoryloxy]succinate, and di(2-propynyl) 2,3-di[ethyl(methoxy)phosphoryloxy]succinate.

Of those, more preferred is use of one or more compounds selected from di(2-propenyl) 2,3-di(methanesulfonyloxy)succinate, di(2-propynyl) 2,3-di(methanesulfonyloxy)succinate, di(2-propenyl) 2,3-di(benzenesulfonyloxy)succinate, di(2-propynyl) 2,3-di(benzenesulfonyloxy)succinate, di(2-propenyl) 2,3-di(4-methylbenzenesulfonyloxy)succinate, di(2-propynyl) 2,3-di(4-methylbenzenesulfonyloxy)succinate, dimethyl 2,3-di(2-propenyloxycarbonyloxy)succinate, dimethyl 2,3-di(formyloxy)succinate, di(2-propenyl 2,3-di(formyloxy)succinate, di(2-propynyl) 2,3-di(formyloxy)succinate, dimethyl 2,3-di(dimethoxyphosphoryloxy)succinate, di(2-propynyl) 2,3-di(dimethoxyphosphoryloxy)succinate, dimethyl 2,3-di(diethoxyphosphoryloxy)succinate, and di(2-propynyl) 2,3-di(diethoxyphosphoryloxy)succinate.

Of the specific compounds represented by the general formula (I-I), most preferred is use of one or more compounds selected from 2-propynyl 2-(methanesulfonyloxy)propionate, 2-propynyl 2-(4-methylbenzenesulfonyloxy)propionate, 2-propynyl 2-(acetyloxy)propionate, 2-propynyl 2-(methoxycarbonyloxy)propionate, 2-propynyl 2-(2-propynyloxycarbonyloxy)propionate, 2-propynyl 2-(formyloxy)propionate, 2-propynyl 2-(dimethoxyphosphoryloxy)propionate, methyl 2-(methanesulfonyloxy)propionate, dimethyl 2,3-di(methanesulfonyloxy)succinate, di(2-propynyl) 2,3-di(methanesulfonyloxy)succinate, dimethyl 2,3-di(formyloxy)succinate, di(2-propynyl) 2,3-di(formyloxy)succinate, dimethyl 2,3-di(dimethoxyphosphoryloxy)succinate, and di(2-propynyl) 2,3-di(dimethoxyphosphoryloxy)succinate.

Regarding the general formula (I-I), the R-form of lactic acid, or that is, L-lactic acid that constitutes the main structure of the starting hydroxy acid derivative compound is industrially widely used, and therefore, the R-form compounds are more preferred.

Regarding the content of at least one compound selected from the hydroxy acid derivative compounds represented by the general formula (I-I) to be contained in the nonaqueous electrolytic solution of the present invention, in case where the content is more than 10% by mass, a surface film may be formed excessively on an electrode to worsen low-temperature cycle properties; but when the content is less than 0.01% by mass, then the surface film formation would be insufficient, therefore failing in attaining the effect of improving high-temperature cycle properties. Consequently, the lower limit of the content of the compound is preferably at least 0.01% by mass relative to the mass of the nonaqueous electrolytic solution, more preferably at least 0.1% by mass, even more preferably at least 0.5% by mass, most preferably at least 1% by mass. The upper limit of the content is preferably at most 10% by mass, more preferably at most 7% by mass, even more preferably at most 5% by mass, most preferably at most 3% by mass.

In the nonaqueous electrolytic solution of the present invention, the compound represented by the general formula (I-I) may exhibit the effect thereof of improving low-temperature and high-temperature cycle properties even when the compound is singly therein; however, when combined with a nonaqueous solvent, an electrolyte salt and further other additives to be mentioned below, the compound can exhibit a specific effect of synergistically improving low-temperature and high-temperature cycle properties. Though not always clear, it may be considered that a mixture surface film having a high ionic conductivity and comprising the constitutive elements of the compound of the general formula (I-I) and, as combined therewith, the nonaqueous solvent, electrolyte salt and other additives could be formed.

[The Second Nonaqueous Electrolytic Solution]

The second nonaqueous electrolytic solution of the present invention comprises an electrolyte dissolved in a nonaqueous solvent and contains at least one hydroxy acid derivative compound represented by the following general formula (II-I) in an amount of from 0.01 to 10% by mass of the nonaqueous electrolytic solution.

[Chemical Formula 15]

(II-I)

(In the formula, $X^{21}$ represents $-CR^{23}R^{24}-(CH_2)_n-$, or represents the following general formula (II-II).)

[Chemical Formula 16]

(II-II)

(In the formula, $R^{21}$ represents an alkylsilyl group having from 3 to 12 carbon atoms, an alkyl group having from 1 to 6 carbon atoms, an alkenyl group having from 2 to 6 carbon atoms, an alkynyl group having from 3 to 6 carbon atoms, an alkanesulfonyl group having from 1 to 6 carbon atoms, an arylsulfonyl group having from 6 to 12 carbon atoms, an acyl group having from 2 to 6 carbon atoms, an alkoxycarbonyl group having from 2 to 6 carbon atoms, an alkenyloxycarbonyl group having from 3 to 7 carbon atoms, an alkynyloxycarbonyl group having from 4 to 7 carbon atoms, a formyl group, a dialkylphosphoryl group having from 2 to 16 carbon atoms, an alkyl(alkoxy)phosphoryl group having from 2 to 16 carbon atoms, or a dialkoxyphosphoryl group having from 2 to 16 carbon atoms; when $R^{21}$ is an alkylsilyl group, then $R^{22}$ is an alkyl group having from 1 to 6 carbon atoms, an alkenyl group having from 2 to 6 carbon atoms, or an alkynyl group having from to 6 carbon atoms; when $R^{21}$ is an alkyl group having from 1 to 6 carbon atoms, an alkenyl group having from 2 to 6 carbon atoms, an alkynyl group having from 3 to 6 carbon atoms, an alkanesulfonyl group having from 1 to 6 carbon atoms, an acyl group having from 2 to 6 carbon atoms, an alkoxycarbonyl group having from 2 to 6 carbon atoms, an alkenyloxycarbonyl group having from 3 to 7 carbon atoms, an alkynyloxycarbonyl group having from 4 to 7 carbon atoms, a formyl group, a dialkylphosphoryl group having from 2 to 16 carbon atoms, an alkyl(alkoxy)phosphoryl group having from 2 to 16 carbon atoms, or a dialkoxyphosphoryl group having from 2 to 16 carbon atoms, then $R^{22}$ is an alkylsilyl group having from 3 to 12 carbon atoms; $R^{23}$ and $R^{24}$ each represent a hydrogen atom or an alkyl group having from 1 to 6 carbon atoms; n indicates an integer of from 0 to 3; at least one hydrogen atom on the carbon atoms of $R^{22}$ may be substituted with a halogen atom, an alkoxy group having from 1 to 4 carbon atoms, or a nitrile group.)

The halogen atom with which the hydrogen atom on the carbon atom of $R^{22}$ is substituted includes a fluorine atom, a chlorine atom, a bromine atom and an iodine atom. Preferred is a fluorine atom or a chlorine atom; and more preferred is a fluorine atom.

The second nonaqueous electrolytic solution containing, as added thereto, the hydroxy acid derivative compound represented by the general formula (II-I) can improve high-temperature cycle properties and low-temperature properties after high-temperature cycles. Though not always clear, the reason may be considered as follows:

In trimethylsilyl trimethylsilyloxyacetate, the hydrogen atoms of both the hydroxyl group and the carboxyl group of the hydroxy acid each are substituted with an alkylsilyl group, and therefore, the compound has a problem in that it decomposes excessively to form a surface film having a high resistance on a negative electrode, therefore worsening the low-temperature properties after high-temperature cycles. In the hydroxy acid derivative compound in the present invention, the hydrogen atom alone of one of the hydroxyl group and the carboxyl group is substituted with an alkylsilyl group and the remaining one has a specific different substituent, and therefore, the surface film to be formed on a negative electrode is prevented from being excessively densified, and is free from the above-mentioned problem. Further, the hydroxy acid derivative compound in the present invention forms a protective surface film also on a positive electrode, and especially in high-temperature cycles, the solvent in the electrolytic solution is prevented from being decomposed on a positive electrode; and consequently, the increase in the positive electrode resistance after high-temperature cycles can be thereby prevented. Accordingly, it is considered that the low-temperature properties after high-temperature cycles can be noticeably improved. In particular, in case where the hydrogen atom of the hydroxyl group is substituted with an alkylsilyl group and when the hydrogen atom of the carboxyl group is substituted with an alkenyl group or an alkynyl group, then the decomposition of the electrolytic solution on a positive electrode can be more effectively inhibited, and the low-temperature properties after high-temperature cycles can be thereby much more improved. In case where the hydrogen atom of the carboxyl group is substituted with an alkylsilyl group and when the hydrogen atom of the hydroxyl group is substituted with a sulfonyl group, the decomposition of the electrolytic solution on a positive electrode can also be more effectively inhibited, and the low-temperature properties after high-temperature cycles can be thereby further more improved.

In the general formula (II-I), the linear or branched alkylsilyl group having from 3 to 12 carbon atoms of the substituents $R^{21}$ and $R^{22}$ includes a trimethylsilyl group, a triethylsilyl group, a tripropylsilyl group, a tributylsilyl group, a tert-butyldimethylsilyl group, etc. Of those, preferred are a trimethylsilyl group and a triethylsilyl group; and more preferred is a trimethylsilyl group.

In the general formula (II-I), the linear or branched alkyl group having from 1 to 6 carbon atoms of the substituents $R^{21}$ and $R^{22}$ includes a methyl group, an ethyl group, a propyl group, a butyl group, a pentyl group, a hexyl group, a 2-propyl group, etc. Of those, preferred are a methyl group and an ethyl group; and more preferred is a methyl group.

The linear or branched alkenyl group having from 2 to 6 carbon atoms of $R^{21}$ and $R^{22}$ includes a vinyl group, a 2-propenyl group, a 2-butenyl group, a 3-butenyl group, a 4-pentenyl group, a 2-methyl-2-propenyl group, a 2-methyl-2-butenyl group, a 3-methyl-2-butenyl group, etc. Of those, preferred is a vinyl group and a 2-propenyl group, and more preferred is a 2-propenyl group.

The linear or branched alkynyl group having from 3 to 6 carbon atoms of $R^{21}$ and $R^{22}$ includes a 2-propynyl group, a 2-butynyl group, a 3-butynyl group, a 4-pentynyl group, a 5-hexynyl group, a 1-methyl-2-propynyl group, a 1-methyl-2-butynyl group, a 1,1-dimethyl-2-propynyl group, etc. Of those, preferred are a 2-propynyl group and a 1,1-dimethyl-2-propynyl group; and more preferred is a 2-propynyl group.

The linear or branched alkanesulfonyl group having from 1 to 6 carbon atoms of the substituent $R^{21}$ in the general formula (II-I) includes a methanesulfonyl group, an ethanesulfonyl group, a propanesulfonyl group, a butanesulfonyl group, a pentanesulfonyl group, a hexanesulfonyl group, etc. Of those, preferred are a methanesulfonyl group, an ethanesulfonyl group, and a propanesulfonyl group; and more preferred is a methanesulfonyl group.

At least one hydrogen atom of the alkanesulfonyl group may be substituted with a fluorine atom. Concretely, there may be mentioned a trifluoromethanesulfonyl group, a trifluoroethanesulfonyl group, etc.

The arylsulfonyl group having from 6 to 12 carbon atoms of the substituent $R^{21}$ in the general formula (II-I) includes a phenyl group, a tolyl group, a mesityl group, etc. Of those, preferred are a phenyl group and a tolyl group; and more preferred is a tolyl group.

At least one hydrogen atom of the arylsulfonyl group may be substituted with a fluorine atom. Concretely, there may be mentioned a 4-fluorobenzenesulfonyl group, a 4-trifluorobenzenesulfonyl group, etc.

The linear or branched acyl group having from 2 to 6 carbon atoms of the substituent $R^{21}$ in the general formula (II-I) includes an acetyl group, a propionyl group, a butyryl group, an isobutyryl group, s pivaloyl group, etc. Of those, preferred are an acetyl group and a propionyl group; and more preferred is an acetyl group.

The linear or branched alkoxycarbonyl group having from 2 to 6 carbon atoms of the substituent $R^{21}$ in the general formula (II-I) includes a methoxycarbonyl group, an ethoxycarbonyl group, a propoxycarbonyl group, an isopropoxycarbonyl group, a butoxycarbonyl group, etc. Of those, preferred are a methoxycarbonyl group and an ethoxycarbonyl group; and more preferred is a methoxycarbonyl group.

The linear or branched alkenyloxycarbonyl group having from 3 to 7 carbon atoms of the substituent $R^{21}$ includes a vinyloxycarbonyl group, a 2-propenyloxycarbonyl group, a 2-butenyloxycarbonyl group, a 3-butenyloxycarbonyl group, a 4-pentenyloxycarbonyl group, a 2-methyl-2-propenyloxycarbonyl group, a 2-methyl-2-butenyloxycarbonyl group, a 3-methyl-2-butenyloxycarbonyl group. Of those, preferred are a vinyloxycarbonyl group and a 2-propenyloxycarbonyl group; and more preferred is a 2-propenyloxycarbonyl group.

The linear or branched alkynyloxycarbonyl group having from 4 to 7 carbon atoms of the substituent $R^{21}$ includes a 2-propynyloxycarbonyl group, a 2-butynyloxycarbonyl group, a 3-butynyloxycarbonyl group, a 4-pentynyloxycarbonyl group, a 5-hexynyloxycarbonyl group, a 1-methyl-2-propynyloxycarbonyl group, a 1-methyl-2-butynyloxycarbonyl group, a 1,1-dimethyl-2-propynyloxycarbonyl group, etc. Of those, preferred are a 2-propynyloxycarbonyl group, and a 1-methyl-2-propynyloxycarbonyl group; and more preferred is a 2-propynyloxycarbonyl group.

The linear or branched dialkylphosphoryl group having from 2 to 16 carbon atoms of the substituent $R^{21}$ in the general formula (II-I) is preferably a dimethylphosphoryl group, a diethylphosphoryl group, a dipropylphosphoryl group or a dibutylphosphoryl group. Of those, more preferred are a dimethylphosphoryl group and a diethylphosphoryl group.

The linear or branched alkyl(alkoxy)phosphoryl group having from 2 to 16 carbon atoms of the substituent $R^{21}$ in the general formula (II-I) is preferably a methoxy(methyl)phosphoryl group, an ethoxy(ethyl)phosphoryl group, a propyl(propyloxy)phosphoryl group, a dibutoxy(butyl)phosphoryl group, an ethoxy(methyl)phosphoryl group, or an ethyl(methoxy)phosphoryl group. Of those, preferred are a methoxy(methyl)phosphoryl group and an ethoxy(ethyl)phosphoryl group.

The linear or branched dialkoxyphosphoryl group having from 2 to 16 carbon atoms of the substituent $R^{21}$ in the general formula (II-I) is preferably a dimethoxyphosphoryl group, a diethoxyphosphoryl group, a dipropoxyphosphoryl group, or a dibutoxyphosphoryl group. Of those, more preferred are a dimethoxyphosphoryl group and a diethoxyphosphoryl group.

When the substituent $R^{21}$ is an alkylsilyl group, the substituent $R^{22}$ is preferably a linear or branched alkenyl group having from 2 to 6 carbon atoms or a linear or branched alkynyl group having from 3 to 6 carbon atoms, rather than a linear or branched alkyl group having from 1 to 6 carbon atoms, most preferably a linear or branched alkynyl group having from 3 to 6 carbon atoms. Of those, preferred are a methyl group, an ethyl group, a vinyl group, a 2-propenyl group, and a 2-propynyl group; more preferred are a vinyl group, a 2-propenyl group and a 2-propynyl group; and most preferred is a 2-propynyl group (or that is, a propargyl group).

When the substituent $R^{22}$ is an alkylsilyl group, the substituent $R^{21}$ is preferably a linear or branched alkenyl group having from 2 to 6 carbon atoms, a linear or branched alkynyl group having from 3 to 6 carbon atoms, a linear or branched alkanesulfonyl group having from 1 to 6 carbon atoms, an arylsulfonyl group having from 6 to 12 carbon atoms, a linear or branched acyl group having from 2 to 6 carbon atoms, a linear or branched alkoxycarbonyl group having from 2 to 6 carbon atoms, a linear or branched alkenyloxycarbonyl group having from 3 to 7 carbon atoms, a linear or branched alkynyloxycarbonyl group having from 4 to 7 carbon atoms, a formyl group, a linear or branched dialkylphosphoryl group having from 2 to 16 carbon atoms, a linear or branched alkyl(alkoxy)phosphoryl group having from 2 to 16 carbon atoms or a linear or branched dialkoxyphosphoryl group having from 2 to 16 carbon atoms, rather than a linear or branched alkyl group having from 1 to 6 carbon atoms, and is more preferably an alkanesulfonyl group, an arylsulfonyl group, an acyl group, an alkoxycarbonyl group, a formyl group, or a dialkoxyphosphoryl group, even more preferably an alkanesulfonyl group, an arylsulfonyl group, an acyl group or a formyl group, and most preferably an alkanesulfonyl group. Of those, preferred are a methyl group, an ethyl group, a vinyl group, a 2-propenyl group, a 2-propynyl group, a methanesulfonyl group, an ethanesulfonyl group, a benzenesulfonyl group, a 4-methylbenzenesulfonyl group, an acetyl group, a propionyl group, a methoxycarbonyl group, an ethoxycarbonyl group, a vinyloxycarbonyl group, a 2-propenyloxycarbonyl group, a 2-propynyloxycarbonyl group, and a formyl group; more preferred are a methanesulfonyl group, a 4-methylbenzenesulfonyl group, an acetyl group, a methoxycarbonyl group, a formyl group, and a dimethoxyphosphoryl group; and most preferred is a methanesulfonyl group.

The substituent $R^{22}$ in the general formula (II-I) where at least one hydrogen atom on the carbon atoms is substituted with a halogen atom, an alkoxy group having from 1 to 4 carbon atoms or a nitrile group is preferably a 2,2,2-trifluoroethyl group, a 2-methoxyethyl group, a 3-methoxypropyl group, a 2-ethoxyethyl group, a cyanomethyl group, a 2-cyanoethyl group, a 2-cyanopropyl group, etc.

In the general formula (II-I) where $X^{21}$ is —$CR^3R^4$—$(CH_2)_n$—, the linear or branched alkyl group having from 1 to 6 carbon atoms of the substituents $R^3$ and $R^4$ is preferably a methyl group, an ethyl group, a propyl group, a butyl group, a pentyl group, a hexyl group, a 2-propyl group, etc. Of those, preferred are a methyl group and an ethyl group; and more preferred is a methyl group.

Preferably, at least one of $R^3$ and $R^4$ is a linear or branched alkyl group having from 1 to 6 carbon atoms (and the other is a hydrogen atom), and more preferably, both of $R^3$ and $R^4$ are linear or branched alkyl groups each having from 1 to 6 carbon atoms. Above all, preferred are a case where at least one of $R^3$ and $R^4$ is a methyl group (and the other is a hydrogen atom), and a case where both of $R^3$ and $R^4$ are methyl groups.

In the general formula (II-I) where $X^{21}$ is —$CR^3R^4$—$(CH_2)_n$—, n is an integer of from 0 to 3, but most preferably n=0.

In the general formula (II-I), in case where $X^{21}$ is —$CR^3R^4$—$(CH_2)_n$—, in which $R^3$ and $R^4$ are different substituents, and $X^{21}$ is the general formula (II-II), the formula includes optical isomers. The optical isomers include R-form and S-form, both of which exhibit the effect of the present invention. The optical isomers may be in the form of a mixture thereof in a desired ratio; and both a case where one optical isomer is excessive over the other (optical active form) and a case where the two optical isomers exist in the same amount (racemic form) exhibit the effect of the present invention.

Further, in the general formula (II-I), in case where $X^{21}$ is the general formula (II-II), the formula has two asymmetric carbons, or that is, the formula further includes diastereomers in addition to the above-mentioned optical isomers. The diastereomers are not always the same in point of the chemical property or the electrochemical property thereof; and therefore, depending on the ratio of the diastereomers, the degree of the effect of the present invention may vary; however, any case where any of the optical isomers is used either singly or in the form of a mixture thereof can exhibit the effect of the present invention.

The compounds of the general formula (II-I) where the substituents fall within the above-mentioned range are preferred as more effective for improving high-temperature cycle properties and low-temperature properties after high-temperature cycles.

Not specifically defined, the hydroxy acid derivative compounds represented by the general formula (II-I) concretely include the following compounds.

The compounds of the general formula (II-I) where $X^{21}$ is —$CR^3R^4$—$(CH_2)_n$—, and $R^{21}$ is an alkylsilyl group include methyl trimethylsilyloxyacetate, ethyl trimethylsilyloxyacetate, n-propyl trimethylsilyloxyacetate, n-butyl trimethylsilyloxyacetate, iso-propyl trimethylsilyloxyacetate, tert-butyl trimethylsilyloxyacetate, vinyl trimethylsilyloxyacetate, 2-propenyl trimethylsilyloxyacetate, 2-butenyl trimethylsilyloxyacetate, 2-propynyl trimethylsilyloxyacetate, 2-butynyl trimethylsilyloxyacetate, 2,2,2-trifluoroethyl trimethylsilyloxyacetate, 2-methoxyethyl trimethylsilyloxyacetate, 2-ethoxyethyl trimethylsilyloxyacetate, cyanomethyl trimethylsilyloxyacetate, 2-cyanoethyl trimethylsilyloxyacetate, 3-cyanopropyl trimethylsilyloxyacetate, etc.;

methyl 2-(trimethylsilyloxy)propionate, ethyl 2-(trimethylsilyloxy)propionate, n-propyl 2-(trimethylsilyloxy)propionate, n-butyl 2-(trimethylsilyloxy)propionate, iso-propyl 2-(trimethylsilyloxy)propionate, tert-butyl 2-(trimethylsilyloxy)propionate, vinyl 2-(trimethylsilyloxy)propionate, 2-propenyl 2-(trimethylsilyloxy)propionate, 2-butenyl 2-(trimethylsilyloxy)propionate, 2-propynyl 2-(trimethylsilyloxy)propionate, 2-butynyl 2-(trimethylsilyloxy)propionate, 2,2,2-trifluoroethyl 2-(trimethylsilyloxy)propionate, 2-methoxyethyl 2-(trimethylsilyloxy)propionate, 2-ethoxyethyl 2-(trimethylsilyloxy)propionate, cyanomethyl 2-(trimethylsilyloxy)propionate, 2-cyanoethyl 2-(trimethylsilyloxy)propionate, 3-cyanopropyl 2-(trimethylsilyloxy)propionate, etc.;

methyl 2-methyl-2-(trimethylsilyloxy)propionate, ethyl 2-methyl-2-(trimethylsilyloxy)propionate, n-propyl 2-methyl-2-(trimethylsilyloxy)propionate, n-butyl 2-methyl-2-(trimethylsilyloxy)propionate, isopropyl 2-methyl-2-(trimethylsilyloxy)propionate, tert-butyl 2-methyl-2-(trimethylsilyloxy)propionate, vinyl 2-methyl-2-(trimethylsilyloxy)propionate, 2-propenyl 2-methyl-2-(trimethylsilyloxy)propionate, 2-butenyl 2-methyl-2-(trimethylsilyloxy)propionate, 2-propynyl 2-methyl-2-(trimethylsilyloxy)propionate, 2-butynyl 2-methyl-2-(trimethylsilyloxy)propionate, 2,2,2-trifluoroethyl 2-methyl-2-(trimethylsilyloxy)propionate, 2-methoxyethyl 2-methyl-2-(trimethylsilyloxy)propionate, cyanomethyl 2-methyl-2-(trimethylsilyloxy)propionate, etc.;

The compounds of the general formula (II-I) where $X^{21}$ is —$CR^3R^4$—$(CH_2)_n$—, and $R^{22}$ is an alkylsilyl group include trimethylsilyl methoxyacetate, trimethylsilyl 2-methoxypropionate, trimethylsilyl 2-methoxy-2-methylpropionate, trimethylsilyl methanesulfonyloxyacetate, trimethylsilyl 2-(methanesulfonyloxy)propionate, trimethylsilyl 2-(methanesulfonyloxy)-2-methylpropionate, trimethylsilyl benzenesulfonyloxyacetate, trimethylsilyl 2-(benzenesulfonyloxy)propionate, trimethylsilyl 2-(benzenesulfonyloxy)-2-methylpropionate, trimethylsilyl 4-methylbenzenesulfonyloxyacetate, trimethylsilyl 2-(4-methylbenzenesulfonyloxy)propionate, trimethylsilyl 2-(4-methylbenzenesulfonyloxy)-2-methylpropionate, trimethylsilyl acetyloxyacetate, trimethylsilyl 2-(acetyloxy)propionate, trimethylsilyl 2-(acetyloxy)-2-methylpropionate, trimethylsilyl formyloxyacetate, trimethylsilyl 2-(formyloxy)propionate, trimethylsilyl 2-(formyloxy)-2-methylpropionate, trimethylsilyl methoxycarbonyloxyacetate, trimethylsilyl 2-(methoxycarbonyloxy)propionate, trimethylsilyl 2-(methoxycarbonyloxy)-2-methylpropionate, trimethylsilyl 2-vinyloxycarbonyloxyacetate, trimethylsilyl 2-propenyloxycarbonyloxyacetate, trimethylsilyl 2-propynyloxycarbonyloxyacetate, trimethylsilyl 2-vinyloxycarbonyloxypropionate, trimethylsilyl 2-(propenyloxycarbonyloxy)propionate, trimethylsilyl 2-(propynyloxycarbonyloxy)propionate, trimethylsilyl dimethylphopshoryloxyacetate, trimethylsilyl 2-(dimethylphosphoryloxy)propionate, trimethylsilyl 2-(dimethylphosphoryloxy)-2-methylpropionate, trimethylsilyl methoxy(methyl)phosphoryloxyacetate, trimethylsilyl 2-[methoxy(methyl)phosphoryloxy]propionate, trimethylsilyl 2-[methoxy(methyl)phosphoryloxy]-2-methylpropionate, trimethylsilyl ethyl(methoxy)phosphoryloxyacetate, trimethylsilyl 2-[ethyl(methoxy)phosphoryloxy]propionate, trimethylsilyl 2-[ethyl(methoxy)phosphoryloxy]-2-methylpropionate, trimethylsilyl ethoxy(methyl)phosphoryloxyacetate, trimethylsilyl 2-[ethoxy(methyl)phosphoryloxy]propionate, trimethylsilyl 2-[ethoxy(methyl)phosphoryloxy]-2-methylpropionate, trimethylsilyl dimethoxyphosphoryloxyacetate, trimethylsilyl diethoxyphosphoryloxyacetate, trimethylsilyl 2-(dimethoxyphosphoryloxy)propionate, trimethylsilyl 2-(dimethoxyphosphoryloxy)-2-methylpropionate, trimethylsilyl 2-(diethoxyphosphoryloxy)propionate, trimethylsilyl 2-(diethoxyphosphoryloxy)-2-methylpropionate, etc.

Preferred examples of the hydroxy acid derivative compounds of the general formula (II-I) where $X^{21}$ is —$CR^3R^4$—$(CH_2)_n$— are one or more selected from methyl 2-(trimethylsilyloxy)propionate, 2-propenyl 2-(trimethylsilyloxy)propionate, 2-propynyl 2-(trimethylsilyloxy)propionate, trimethylsilyl methoxyacetate, trimethylsilyl 2-(methanesulfonyloxy)propionate, trimethylsilyl 2-(benzenesulfonyloxy)propionate, trimethylsilyl 2-(4-methylbenzenesulfonyloxy)propionate, trimethylsilyl acetyloxyacetate, trimethylsilyl formyloxyacetate, trimethylsilyl methoxycarbonyloxyacetate, trimethylsilyl 2-propenyloxycarbonyloxyacetate, trimethylsilyl 2-propynyloxycarbonyloxyacetate, trimethylsilyl dimethoxyphosphoryloxyacetate, and trimethylsilyl diethoxyphosphoryloxyacetate.

Of those, more preferred are 2-propynyl 2-(trimethylsilyloxy)propionate, trimethylsilyl 2-(methanesulfonyloxy)propionate, trimethylsilyl 2-(benzenesulfonyloxy)propionate, trimethylsilyl 2-(4-methylbenzenesulfonyloxy)propionate, trimethylsilyl acetyloxyacetate, trimethylsilyl formyloxyacetate, trimethylsilyl dimethoxyphosphoryloxyacetate, and trimethylsilyl diethoxyphosphoryloxyacetate; and even more preferred are 2-propynyl 2-(trimethylsilyloxy)propionate, trimethylsilyl 2-(methanesulfonyloxy)propionate, trimethylsilyl 2-(benzenesulfonyloxy)propionate, trimethylsilyl 2-(4-methylbenzenesulfonyloxy)propionate, trimethylsilyl 2-propenyloxycarbonyloxyacetate, and trimethylsilyl 2-propynyloxycarbonyloxyacetate.

The compounds of the general formula (II-I) where $X^{21}$ is the general formula (II-II) and $R^{21}$ is an alkylsilyl group include dimethyl 2,3-di(trimethylsilyloxy)succinate, diethyl 2,3-di(trimethylsilyloxy)succinate, di(n-propyl 2,3-di(trimethylsilyloxy)succinate, di(n-butyl) 2,3-di(trimethylsilyloxy)succinate, di(iso-propyl) 2,3-di(trimethylsilyloxy)succinate, di(tert-butyl) 2,3-di(trimethylsilyloxy)succinate, divinyl 2,3-di(trimethylsilyloxy)succinate, di(2-propenyl) 2,3-di(trimethylsilyloxy)succinate, di(2-butenyl) 2,3-di(trimethylsilyloxy)succinate, di-(2-propynyl) 2,3-di(trimethylsilyloxy)succinate, di(2-butynyl) 2,3-di(trimethylsilyloxy)succinate, di(2,2,2-trifluoroethyl) 2,3-di(trimethylsilyloxy)succinate, di(2-methoxyethyl) 2,3-di(trimethylsilyloxy)succinate, di(2-cyanoethyl) 2,3-di(trimethylsilyloxy)succinate, etc.

Of those, preferred are one or more selected from dimethyl 2,3-di(trimethylsilyloxy)succinate, di(2-propenyl) 2,3-di(trimethylsilyloxy)succinate, and di(2-propynyl) 2,3-di(trimethylsilyloxy)succinate.

The compounds of the general formula (II-I) where $X^{21}$ is the general formula (II-II) and $R^{22}$ is an alkylsilyl group include di(trimethylsilyl) 2,3-di(methanesulfonyloxy)succinate, di(trimethylsilyl) 2,3-di(benzenesulfonyloxy)succinate, di(trimethylsilyl) 2,3-di(4-methylbenzenesulfonyloxy)succinate, di(trimethylsilyl) 2,3-di(acetyloxy)succinate, di(trimethylsilyl) 2,3-di(formyloxy)succinate, di(trimethylsilyl) 2,3-di(methoxycarbonyloxy)succinate, di(trimethylsilyl) 2,3-di(vinyloxycarbonyloxy)succinate, di(trimethylsilyl) 2,3-di(2-propenyloxycarbonyloxy)succinate, di(trimethylsilyl) 2,3-di(2-propynyloxycarbonyloxy)succinate, di(trimethylsilyl) 2,3-bis(dimethoxyphosphoryloxy)succinate, di(trimethylsilyl) 2,3-bis(diethoxyphosphoryloxy)succinate, etc.

Of the specific compounds represented by the general formula (II-I), more preferred are one or more selected from methyl trimethylsilyloxyacetate, methyl 2-(trimethylsilyloxy)propionate, methyl 2-methyl-2-(trimethylsilyloxy)propionate, 2-propenyl 2-(trimethylsilyloxy)propionate, 2-propynyl 2-(trimethylsilyloxy)propionate, trimethylsilyl methoxyacetate, trimethylsilyl 2-(methanesulfonyloxy)propionate, trimethylsilyl 2-(benzenesulfonyloxy)propionate, trimethylsilyl 2-(4-methylbenzenesulfonyloxy)propionate, trimethylsilyl acetyloxyacetate, trimethylsilyl formyloxyacetate, trimethylsilyl methoxycarbonyloxyacetate, trimethylsilyl 2-propenyloxycarbonyloxyacetate, trimethylsilyl 2-propynyloxycarbonyloxyacetate, trimethylsilyl dimethoxyphosphoryloxyacetate, trimethylsilyl diethoxyphosphoryloxyacetate, dimethyl 2,3-di(trimethylsilyloxy)succinate, di(2-propenyl) 2,3-di(trimethylsilyloxy)succinate, di(2-propynyl) 2,3-di(trimethylsilyloxy)succinate, di(trimethylsilyl) 2,3-di(methanesulfonyloxy)succinate, di(trimethylsilyl) 2,3-di(acetyloxy)succinate, and di(trimethylsilyl) 2,3-di(formyloxy)succinate; and most preferred are one or more selected from methyl trimethylsilyloxyacetate, methyl 2-(trimethylsilyloxy)propionate, methyl 2-methyl-2-(trimethylsilyloxy)propionate, 2-propenyl 2-(trimethylsilyloxy)propionate, 2-propynyl 2-(trimethylsilyloxy)propionate, trimethylsilyl methoxyacetate, trimethylsilyl 2-(methanesulfonyloxy)propionate, trimethylsilyl 2-(4-methylbenzenesulfonyloxy)propionate, trimethylsilyl acetyloxyacetate, trimethylsilyl formyloxyacetate, trimethylsilyl methoxycarbonyloxyacetate, trimethylsilyl 2-propynyloxycarbonyloxyacetate, trimethylsilyl dimethoxyphosphoryloxyacetate, dimethyl 2,3-di(trimethylsilyloxy)succinate, di(2-propynyl) 2,3-di(trimethylsilyloxy)succinate, and di(trimethylsilyl) 2,3-di(methanesulfonyloxy)succinate.

Regarding the content of at least one compound represented by the general formula (II-I) to be contained in the nonaqueous electrolytic solution of the present invention, in case where the content is more than 10% by mass, a surface film may be formed excessively on an electrode to worsen low-temperature cycle properties; but when the content is less than 0.01% by mass, then the surface film formation would be insufficient, therefore failing in attaining the effect of improving high-temperature cycle properties. Consequently, the lower limit of the content of the compound is preferably at least 0.01% by mass relative to the mass of the nonaqueous electrolytic solution, more preferably at least 0.1% by mass, even more preferably at least 0.5% by mass, most preferably at least 1% by mass. The upper limit of the content is preferably at most 10% by mass, more preferably at most 7% by mass, even more preferably at most 5% by mass, most preferably at most 3% by mass.

In the nonaqueous electrolytic solution of the present invention, the compound represented by the general formula (II-I) may exhibit the effect thereof of improving low-temperature and high-temperature cycle properties even when the compound is singly therein; however, when combined with a nonaqueous solvent, an electrolyte salt and further other additives to be mentioned below, the compound can exhibit a specific effect of synergistically improving low-temperature and high-temperature cycle properties. Though not always clear, it may be considered that a mixture surface film having a high ionic conductivity and comprising the constitutive elements of the compound of the general formula (II-I) and, as combined therewith, the nonaqueous solvent, electrolyte salt and other additives could be formed.

[The Third Nonaqueous Electrolytic Solution]

The third nonaqueous electrolytic solution of the present invention comprises an electrolyte salt dissolved in a nonaqueous solvent and contains a carboxylate represented by the following general formula (III-I) in an amount of from 0.01 to 5% by mass of the nonaqueous electrolytic solution.

[Chemical Formula 17]

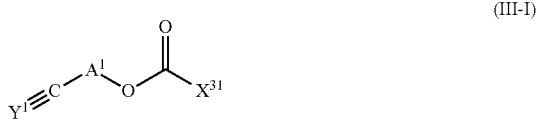

(III-I)

(In the formula, $X^{31}$ represents $-A^2-C\equiv Y^2$, $-A^2-C(=O)O-A^3-C\equiv Y^2$ or $-A^2-C(=O)O-A^4$; $A^1$, $A^2$ and $A^3$ each independently represent an alkylene group having from 1 to 6 carbon atoms; $A^4$ represents an alkyl group having from 1 to 6 carbon atoms; $Y^1$ and $Y^2$ each independently represent CH or N.)

Though not always clear, the reason why the third nonaqueous electrolytic solution can greatly improve low-temperature cycle properties may be considered as follows:

The carboxylate represented by the general formula (III-I) in the present invention is a compound in which the alcohol moiety of the ester group of the carboxylate has a carbon-carbon triple bond (ethynyl group) or a carbon-nitrogen triple bond (cyano group) and the carbonyl carbon therein has any of an ester, ethynyl or cyano group via an alkylene group therebetween, or that is, the carboxylate has at least an ethynyl group or a cyano group in the molecular structure, and therefore can form a good surface film in initial charging. In other words, the compound has an electron-rich specific group (ethynyl group or cyano group) at the end of the molecular structure thereof and has a specific substituent, and therefore the electron-rich specific groups are taken in the surface film formed of the compound, as uniformly dispersed therein, or that is, the compound can form a surface film of high Li ion permeability. Accordingly, it is considered that the compound can noticeably improve low-temperature cycle properties.

The linear or branched alkylene group having from 1 to 6 carbon atoms of $A^1$ to $A^3$ in the general formula (III-I) concretely includes, as preferred examples thereof, a methylene group, an ethylene group, a trimethylene group, a tetramethylene group, a pentamethylene group, a hexamethylene group, a propane-1,2-diyl group, a butane-1,3-diyl group, a pentane-1,4-diyl group, a hexane-1,5-diyl group, a 2-methylpropane-1,3-diyl group, a 2,2-dimethylpropane-1,3-diyl group, an ethane-1,1-diyl group, a propane-2,2-diyl group, etc. However, the bonding position (that is, the bonding order) of these groups in the general formula (III-I) is not specifically defined.

Of those, the linear alkylene group of $A^2$ is more preferably an alkylene group having from 2 to 6 carbon atoms such as an ethylene group, a trimethylene group, a tetramethylene group, a pentamethylene group or a hexamethylene group, even more preferably an ethylene group, a trimethylene group or a tetramethylene group, from the viewpoint of improving low-temperature cycle properties. The branched alkylene group is more preferably an alkylene group having from 3 to 5 carbon atoms such as a propane-1,2-diyl group, a butane-1,3-diyl group, a pentane-1,4-diyl group, a 2-methylpropane-1,2-diyl group, a 2,2-dimethylpropane-1,3-diyl group or a propane-2,2-diyl group, even more preferably a propane-1,2-diyl group or a butane-1,3-diyl group.

The linear or branched alkyl group having from 1 to carbon atoms of $A^4$ in the general formula (III-I) concretely includes, as preferred examples thereof, a methyl group, an ethyl group, an n-propyl group, an n-butyl group, an n-pentyl group, an n-hexyl group, an iso-propyl group, a sec-butyl group, a tert-butyl group, a tert-amyl group, etc. Of those, more preferred are a methyl group, an ethyl group, an n-propyl group, an n-butyl group, and an iso-propyl group; and even more preferred are a methyl group and an ethyl group.

[a] [In case where $X^{31}$ in the general formula (III-I) is $-A^2-C\equiv CH$]

As concrete groups, preferably mentioned are a 2-propynyl group, a 3-butynyl group, a 4-pentynyl group, a 5-hexynyl group, a 1-methyl-2-propynyl group, a 1-methyl-3-butynyl group, a 1-methyl-4-pentynyl group, a 1-methyl-5-hexynyl group, a 1,1-dimethyl-2-propynyl group, a 1,1-dimethyl-3-butynyl group, a 1,1-dimethyl-4-pentynyl group, a 1,1-dimethyl-5-hexynyl group, etc.

Of those, preferred are a 2-propynyl group and a 1,1-dimethyl-2-propynyl group; and more preferred is a 2-propynyl group.

[b] [In case where $X^{31}$ in the general formula (III-I) is $-A^2-C\equiv N$]

As concrete groups, preferably mentioned are a cyanomethyl group, a 2-cyanoethyl group, a 3-cyanopropyl group, a 4-cyanobutyl group, a 2-cyano-1-methylethyl group, a 3-cyano-1-methylpropyl group, a 4-cyano-1-methylbutyl group, a 2-cyano-1,1-dimethylethyl group, a 3-cyano-1,1-dimethylpropyl group, a 4-cyano-1,1-dimethylbutyl group, etc.

Of those, preferred are a 4-cyanobutyl group and a 4-cyano-2-methylbutyl group; and more preferred is a 4-cyanobutyl group.

[c] [In case where $X^{31}$ in the general formula (III-I) is $-A^2-CO_2-A^3-C\equiv CH$]

As concrete groups, preferably mentioned are a (2-propynyloxycarbonyl)methyl group, a 2-(2-propynyloxycarbonyl)ethyl group, a 3-(2-propynyloxycarbonyl)propyl group, a 4-(2-propynyloxycarbonyl)butyl group, a (1-methyl-2-propynyloxycarbonyl)methyl group, a 2-(1-methyl-2-propynyloxycarbonyl)ethyl group, a 3-(1-methyl-2-propynyloxycarbonyl)propyl group, a 4-(1-methyl-2-propynyloxycarbonyl)butyl group, a (1,1-dimethyl-2-propynyloxycarbonyl)methyl group, a 2-(1,1-dimethyl-2-propynyloxycarbonyl)ethyl group, a 3-(1,1-dimethyl-2-propynyloxycarbonyl)propyl group, a 4-(1,1-dimethyl-2-propynyloxycarbonyl)butyl group, a 5-(2-propynyloxycarbonyl)pentyl group, a 6-(2-propynyloxycarbonyl)hexyl group, a 1-methyl-2-(2-propynyloxycarbonyl)ethyl group, a 2-methyl-2-(2-propynyloxycarbonyl)ethyl group, a 1-methyl-3-(2-propynyloxycarbonyl)propyl group, a 2-methyl-3-(2-propynyloxycarbonyl)propyl group, a 3-methyl-3-(2-propynyloxycarbonyl)propyl group, a 1-methyl-4-(2-propynyloxycarbonyl)butyl group, a 4-methyl-4-(2-propynyloxycarbonyl)butyl group, etc.

Of those, preferred are a 2-(2-propynyloxycarbonyl)ethyl group, a 3-(2-propynyloxycarbonyl)propyl group, a 4-(2-propynyloxycarbonyl)butyl group, a 2-(1,1-dimethyl-2-propynyloxycarbonyl)ethyl group, a 3-(1,1-dimethyl-2-propynyloxycarbonyl)propyl group, a 4-(1,1-dimethyl-2-propynyloxycarbonyl)butyl group, a 1-methyl-2-(2-propynyloxycarbonyl)ethyl group, a 2-methyl-2-(2-propynyloxycarbonyl)ethyl group, a 1-methyl-3-(2-propynyloxycarbonyl)propyl group, a 2-methyl-3-(2-propynyloxycarbonyl)propyl group, and a 3-methyl-4-(2-propynyloxycarbonyl)butyl group; and more preferred are a 2-(2-propynyloxycarbonyl)ethyl group, a 3-(2-propynyloxycarbonyl)propyl group, a 4-(2-propynyloxycarbonyl)butyl group, a 1-methyl-2-(2-propynyloxycarbonyl)ethyl group, a 2-methyl-2-(2-propynyloxycarbonyl)ethyl group, a 1-methyl-3-(2-propynyloxycarbonyl)propyl group, and a 2-methyl-3-(2-propynyloxycarbonyl)propyl group.

[d] [In case where $X''$ in the general formula (III-I) is -$A^2$-C(=O)O-$A^3$-C≡N]

As concrete groups, preferably mentioned are a (cyanomethoxycarbonyl)methyl group, a 2-(cyanomethoxycarbonyl)ethyl group, a 3-(cyanomethoxycarbonyl)propyl group, a 4-(cyanomethoxycarbonyl)butyl group, a (2-cyanoethoxycarbonyl)methyl group, a 2-(2-cyanoethoxycarbonyl)ethyl group, a 3-(2-cyanoethoxycarbonyl)propyl group, a 4-(2-cyanoethoxycarbonyl)butyl group, a (3-cyanopropoxycarbonyl)methyl group, a 2-(3-cyanopropoxycarbonyl)ethyl group, a 3-(3-cyanopropoxycarbonyl)propyl group, a 4-(3-cyanopropoxycarbonyl)butyl group, a (1,1-dimethylcyanomethoxycarbonyl)methyl group, a 2-(1,1-dimethylcyanomethoxycarbonyl)ethyl group, a 3-(1,1-dimethylcyanomethoxycarbonyl)propyl group, a 4-(1,1-dimethylcyanomethoxycarbonyl)butyl group, a 1-methyl-2-(2-cyanoethoxycarbonyl)ethyl group, a 2-methyl-2-(2-cyanoethoxycarbonyl)ethyl group, a 1-methyl-3-(2-cyanoethoxycarbonyl)propyl group, a 3-methyl-3-(2-cyanoethoxycarbonyl)propyl group, a 1-methyl-4-(2-cyanoethoxycarbonyl)butyl group, a 4-methyl-4-(2-cyanoethoxycarbonyl)butyl group, a 1-methyl-2-(1,1-dimethylcyanomethoxycarbonyl)ethyl group, a 2-methyl-2-(1,1-dimethylcyanomethoxycarbonyl)ethyl group, a 1-methyl-3-(1,1-dimethylcyanomethoxycarbonyl)propyl group, a 3-methyl-3-(1,1-dimethylcyanomethoxycarbonyl)propyl group, a 1-methyl-4-(1,1-dimethylcyanomethoxycarbonyl)butyl group, a 4-methyl-4-(1,1-dimethylcyanomethoxycarbonyl)butyl group, etc.

Of those, preferred are a 2-(2-cyanoethoxycarbonyl)ethyl group, a 3-(2-cyanoethoxycarbonyl)propyl group, a 4-(2-cyanoethoxycarbonyl)butyl group, a 2-(1,1-dimethyl-2-cyanoethoxycarbonyl)ethyl group, a 3-(1,1-dimethyl-2-cyanoethoxycarbonyl)propyl group, a 4-(1,1-dimethyl-2-cyanoethoxycarbonyl)butyl group, a 1-methyl-2-(2-cyanoethoxycarbonyl)ethyl group, a 2-methyl-2-(2-cyanoethoxycarbonyl)ethyl group, a 1-methyl-3-(2-cyanoethoxycarbonyl)propyl group, a 2-methyl-3-(2-cyanoethoxycarbonyl)propyl group, and a 3-(cyanoethoxycarbonyl)butyl group; and more preferred are a 2-(2-cyanoethoxycarbonyl)ethyl group, a 3-(2-cyanoethoxycarbonyl)propyl group, a 4-(2-cyanoethoxycarbonyl)butyl group, a 1-methyl-2-(2-cyanoethoxycarbonyl)ethyl group, a 2-methyl-2-(2-cyanoethoxycarbonyl)ethyl group, a 1-methyl-3-(2-cyanoethoxycarbonyl)propyl group, and a 2-methyl-3-(2-cyanoethoxycarbonyl)propyl group.

[e] [In case where $X^{31}$ in the general formula (III-I) is -$A^2$-$CO_2$-$A^4$]

As concrete groups, preferably mentioned are a (methoxycarbonyl)methyl group, an (ethoxycarbonyl)methyl group, a (1-propoxycarbonyl)methyl group, a (2-propoxycarbonyl)methyl group, a (1-butoxycarbonyl)methyl group, a (2-methyl-2-propoxycarbonyl)methyl group, a 2-(methoxycarbonyl)ethyl group, a 2-(ethoxycarbonyl)ethyl group, a 2-(1-propoxycarbonyl)ethyl group, a 2-(2-propoxycarbonyl)ethyl group, a 2-(1-butoxycarbonyl)ethyl group, a 2-(2-methyl-2-propoxycarbonyl)ethyl group, a 3-(methoxycarbonyl)propyl group, a 3-(ethoxycarbonyl)propyl group, a 3-(1-propoxycarbonyl)propyl group, a 3-(2-propoxycarbonyl)propyl group, a 3-(1-butoxycarbonyl)propyl group, a 3-(2-methyl-2-propoxycarbonyl)propyl group, a 4-(methoxycarbonyl)butyl group, a 4-(ethoxycarbonyl)butyl group, a 4-(1-propoxycarbonyl)butyl group, a 4-(2-propoxycarbonyl)butyl group, a 4-(1-butoxycarbonyl)butyl group, a 4-(2-methyl-2-propoxycarbonyl)butyl group, a 5-(methoxycarbonyl)pentyl group, a 5-(ethoxycarbonyl)pentyl group, a 6-(methoxycarbonyl)hexyl group, a 6-(ethoxycarbonyl)hexyl group, a 1-methyl-2-(methoxycarbonyl)ethyl group, a 2-methyl-2-(methoxycarbonyl)ethyl group, a 1-methyl-2-(ethoxycarbonyl)ethyl group, a 2-methyl-2-(ethoxycarbonyl)ethyl group, a 1-methyl-3-(methoxycarbonyl)propyl group, a 2-methyl-3-(methoxycarbonyl)propyl group, a 3-methyl-3-(methoxycarbonyl)propyl group, a 1-methyl-3-(ethoxycarbonyl)propyl group, a 2-methyl-3-(ethoxycarbonyl)propyl group, a 3-methyl-3-(ethoxycarbonyl)propyl group, a 1-methyl-4-(methoxycarbonyl)butyl group, a 4-methyl-4-(methoxycarbonyl)butyl group, a 1-methyl-4-(ethoxycarbonyl)butyl group, a 4-methyl-4-(ethoxycarbonyl)butyl group, etc.

Of those, preferred are a 2-(methoxycarbonyl)methyl group, a 2-(methoxycarbonyl)ethyl group, a 3-(methoxycarbonyl)propyl group, a 4-(methoxycarbonyl)butyl group, a 2-(ethoxycarbonyl)ethyl group, a 3-(ethoxycarbonyl)propyl group, a 4-(ethoxycarbonyl)butyl group, a 1-methyl-2-(methoxycarbonyl)ethyl group, a 2-methyl-2-(methoxycarbonyl)ethyl group, a 1-methyl-3-(methoxycarbonyl)propyl group, a 2-methyl-3-(2-methoxycarbonyl)propyl group, a 3-methyl-3-(methoxycarbonyl)propyl group, a 1-methyl-4-(methoxycarbonyl)butyl group, and a 4-methyl-4-(methoxycarbonyl)butyl group; and more preferred are a 2-(methoxycarbonyl)ethyl group, a 3-(methoxycarbonyl)propyl group, a 4-(methoxycarbonyl)butyl group, a 1-methyl-2-(methoxycarbonyl)ethyl group, and a 2-methyl-2-(methoxycarbonyl)ethyl group.

Of the above-mentioned [a] to [e], more preferred are [b], [c] and [d] from the viewpoint of low-temperature properties; and even more preferred are [c] and [d].

The compounds represented by the general formula (III-I) include compounds represented by the following general formula (III-III):

[Chemical Formula 18]

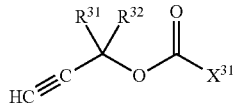

(III-III)

(In the formula, $R^{31}$ and $R^{32}$ each independently represent an alkyl group having from 1 to 4 carbon atoms, or a hydrogen atom; $X^{31}$ represents —$R^{33}$—$CO_2$—$CR^{31}R^{32}$C≡CH (where $R^{31}$ and $R^{32}$ are the same as above) or —$R^{33}$—C≡N; $R^{33}$ represents a linear or branched alkylene group having from 1 to 6 carbon atoms.)

In the general formula (III-III), the substituents $R^{31}$ and $R^{32}$ each are preferably an alkyl group having from 1 to 4 carbon atoms or a hydrogen atom. The alkyl group having from 1 to 4 carbon atoms is preferably a methyl group, an ethyl group, a propyl group or a butyl group.

Of those, more preferably, $R^{31}$ and $R^{32}$ each are a methyl group, an ethyl group or a hydrogen atom from the viewpoint of improving low-temperature cycle properties, even more preferably a methyl group or a hydrogen atom.

In the general formula (III-III), the substituent $R^{31}$ is more preferably a linear or branched alkylene group having from 1 to 6 carbon atoms. The linear or branched alkylene group having from 1 to 6 carbon atoms is preferably a methylene group, an ethylene group, a trimethylene group, a tetramethylene group, a pentamethylene group, a hexamethylene group, a propane-1,2-diyl group, a butane-1,3-diyl group, a pentane-1,4-diyl group, a hexane-1,5-diyl group, a 2-methylpropane-1,3-diyl group, a 2,2-dimethylpropane-1,3-diyl group, etc. However, the bonding position (that is, the bonding order) of these groups in the general formula (III-I) is not specifically defined.

Of those, the linear alkylene group of $R^3$ is more preferably an alkylene group having from 2 to 6 carbon atoms such as an ethylene group, a trimethylene group, a tetramethylene group or a pentamethylene group, even more preferably a tetramethylene group, a pentamethylene group or a hexamethylene group from the viewpoint of improving low-temperature cycle properties. The branched alkylene group is more preferably an alkylene group having from 3 to 5 carbon atoms such as a propane-1,2-diyl group, a butane-1,3-diyl group, a pentane-1,4-diyl group, a 2-methylpropane-1,2-diyl group or a 2,2-dimethylpropane-1,3-diyl group, even more preferably a propane-1,2-diyl group or a butane-1,3-diyl group.

In case where $X^{31}$ in the general formula (III-III) is —$R^{33}$—$CO_2$—$CR^{31}R^{32}$C≡CH, $R^{33}$ is especially preferably a branched alkylene group, most preferably a propane-1,2-diyl group or a butane-1,3-diyl group.

As specific examples of the compounds represented by the general formula (III-I) where $X^{31}$ is -$A^2$-C≡CH and $Y^1$ is CH, preferably mentioned are 2-propynyl 3-butynoate, 3-butynyl 3-butynoate, 1-methyl-2-propynyl 3-butynoate, 1,1-dimethyl-2-propynyl 3-butynoate, 2-propynyl 4-pentynoate, 3-butynyl 4-pentynoate, 1-methyl-2-propynyl 4-pentynoate, 1,1-dimethyl-2-propynyl 4-pentynoate, 2-propynyl 5-hexynoate, 3-butynyl 5-hexynoate, 1-methyl-2-propynyl 5-hexynoate, 1,1-dimethyl-2-propynyl 5-hexynoate, 2-propynyl 6-heptynoate, 3-butynyl 6-heptynoate, 1-methyl-2-propynyl 6-heptynoate, 1,1-dimethyl-2-propynyl 6-heptynoate.

Of the above-mentioned compounds, more preferred are carboxylates such as 2-propynyl 3-butynoate, 1-methyl-2-propynyl 3-butynoate and 1,1-dimethyl-2-propynyl 3-butynoate, from the viewpoint of improving low-temperature cycle properties.

In case where $X^{31}$ is -$A^2$-C≡CH and $Y^1$ is N, preferred are cyanomethyl 3-butynoate, 2-cyanoethyl 3-butynoate, 3-cyanopropyl 3-butynoate, 4-cyanobutyl 3-butynoate, 1,1-dimethylcyanomethyl 3-butynoate, cyanomethyl 4-pentynoate, 2-cyanoethyl 4-pentynoate, 3-cyanopropyl 4-pentynoate, 4-cyanobutyl 4-pentynoate, 1,1-dimethylcyanomethyl 4-pentynoate, cyanomethyl 5-hexynoate, 2-cyanoethyl 5-hexynoate, 3-cyanopropyl 5-hexynoate, 4-cyanobutyl 5-hexynoate, 1,1-dimethylcyanomethyl 5-hexynoate, cyanomethyl 6-heptynoate, 2-cyanoethyl 6-heptynoate, 3-cyanopropyl 6-heptynoate, 4-cyanobutyl 6-heptynoate, 1,1-dimethylcyanomethyl 6-heptynoate.

Of the above-mentioned compounds, more preferred are carboxylates such as 2-cyanoethyl 3-butynoate, 3-cyanopropyl 3-butynoate, 4-cyanobutyl 3-butynoate, etc., from the viewpoint of improving low-temperature cycle properties.

In case where $X^{31}$ is -$A^2$-C≡N and $Y^1$ is CH, preferred are 2-propynyl 3-cyanopropionate, 2-propynyl 4-cyanobutanoate, 2-propynyl 5-cyanovalerate, 1-methyl-2-propynyl 5-cyanovalerate, 1,1-dimethyl-2-propynyl 5-cyanovalerate, 2-propynyl 6-cyanohexanoate, 2-propynyl 7-cyanoheptanoate, 2-propynyl 3-cyano-2-methylpropionate, 2-propynyl 3-cyano-3-methylpropionate, 2-propynyl 4-cyano-2-methylbutanoate, 2-propynyl 4-cyano-3-methylbutanoate, 2-propynyl 4-cyano-4-methylbutanoate, 1-methyl-2-propynyl 3-cyano-2-methylpropionate, 1-methyl-2-propynyl 4-cyano-2-methylbutanoate, 1-methyl-2-propynyl 5-cyano-2-methylvalerate, 1,1-dimethyl-2-propynyl 3-cyano-2-methylpropionate, 1,1-dimethyl-2-propynyl 4-cyano-2-methylbutanoate, 1,1-dimethyl-2-propynyl 5-cyano-4-methylvalerate, 2-propynyl 3-cyano-2-methylpropionate, 2-propynyl 4-cyano-2-methylbutanoate, 2-propynyl 5-cyano-2-methylvalerate, 2-propynyl 3-cyano-2,2-dimethylpropionate, 2-propynyl 4-cyano-2,2-dimethylbutanoate, 2-propynyl 5-cyano-2,2-dimethylvalerate.

Of the above-mentioned compounds, more preferred are carboxylates such as 2-propynyl 3-cyanopropionate, 2-propynyl 4-cyanobutanoate, 2-propynyl 5-cyanovalerate, 1-methyl-2-propynyl 5-cyanovalerate, 1,1-dimethyl-2-propynyl 5-cyanovalerate, 2-propynyl 3-cyano-2-methylpropionate, 2-propynyl 3-cyano-3-methylpropionate, etc., from the viewpoint of improving low-temperature cycle properties.

In case where $X^{31}$ is -$A^2$-C≡N and $Y^1$ is N, preferred are 2-cyanoethyl 3-cyanopropionate, 2-cyanoethyl 4-cyanobutanoate, cyanomethyl 5-cyanovalerate, 2-cyanoethyl 5-cyanovalerate, 3-cyanopropyl 5-cyanovalerate, 4-cyanobutyl 5-cyanovalerate, 1,1-dimethylcyanomethyl 5-cyanovalerate, 2-cyanoethyl 6-cyanohexanoate, 2-cyanoethyl 7-cyanoheptanoate, 2-cyanoethyl 3-cyano-2-methylpropionate, 2-cyanoethyl 3-cyano-3-methylpropionate, 2-cyanoethyl 4-cyano-2-methylbutanoate, 2-cyanoethyl 4-cyano-3-methylbutanoate, 2-cyanoethyl 4-cyano-4-methylbutanoate, 3-cyanopropyl 3-cyano-2-methylpropionate, 3-cyanopropyl 4-cyano-2-methylbutanoate, 3-cyanopropyl 5-cyano-2-methylvalerate, 4-cyanobutyl 3-cyano-2-methylpropionate, 4-cyanobutyl 4-cyano-2-methylbutanoate, 4-cyanobutyl 5-cyano-2-methylvalerate, 2-cyanoethyl 3-cyano-2,2-dimethylpropionate, 2-cyanoethyl 4-cyano-2,2-dimethylbutanoate, 2-cyanoethyl 5-cyano-2,2-dimethylvalerate.

Of the above-mentioned compounds, more preferred are carboxylates such as 2-cyanoethyl 3-cyanopropyonate, 2-cyanoethyl 4-cyanobutanoate, 2-cyanoethyl 5-cyanovalerate, 2-cyanoethyl 3-cyano-2-methylpropionate, 2-cyanoethyl 3-cyano-3-methylpropionate, etc., from the viewpoint of improving low-temperature cycle properties.

In case where $X''$ is -$A^2$-$CO_2$-$A^3$-C≡CH and $Y^1$ is CH, preferred are di(2-propynyl)succinate, di(2-propynyl) glutarate, di(2-propynyl) adipate, di(2-propynyl) pimelate, di(2-propynyl) suberate, di(2-propynyl) 2-methylsuccinate, di(2-propynyl) 2-methylglutarate, di(2-propynyl) 3-methylglutarate, di(2-propynyl) 2-methyladipate, di(2-propynyl) 3-methyladipate, di(3-butynyl)succinate, di(3-butynyl) glutarate, di(3-butynyl) adipate, di(1-methyl-2-propynyl)succinate, di(1-methyl-2-propynyl) glutarate, di(1-methyl-2-propynyl) adipate, di(1,1-dimethyl-2-propynyl) succinate, di(1,1-dimethyl-2-propynyl) glutarate, di(1,1-dimethyl-2-propynyl) adipate.

Of the above-mentioned compounds, more preferred are linear carboxylic diesters in which the main chain is a straight chain, such as di(2-propynyl)succinate, di(2-propynyl glutarate, di(2-propynyl) adipate, di(2-propynyl) pimelate, etc., and branched carboxylic diesters such as di(2-propynyl) 2-methylsuccinate, di(2-propynyl) 2-methylglutarate, di(2-propynyl) 3-methylglutarate, di(2-propynyl) 2-methyladipate, di(2-propynyl) 3-methyladipate, etc., from the viewpoint of improving low-temperature cycle properties.

In case where $X^{31}$ is -A$^2$-CO$_2$-A$^3$-C≡CH and $Y^1$ is N, preferred are cyanomethyl(2-propynyl)succinate, (2-cyanoethyl)(2-propynyl)succinate, (2-cyanoethyl)(1-methyl-2-propynyl)succinate, (2-cyanoethyl)(1,1-dimethyl-2-propynyl)succinate, (3-cyanopropyl)(2-propynyl)succinate, (4-cyanobutyl)(2-propynyl)succinate, (1,1-dimethylcyanomethyl)(2-propynyl)succinate, cyanomethyl(2-propynyl) glutarate, (2-cyanoethyl)(2-propynyl) glutarate, 2-(cyanoethyl)(1-methyl-2-propynyl) glutarate, (2-cyanoethyl)(1,1-dimethyl-2-propynyl) glutarate, (3-cyanopropyl)(2-propynyl) glutarate, (4-cyanobutyl)(2-propynyl) glutarate, (1,1-dimethylcyanomethyl)(2-propynyl) glutarate, cyanomethyl (2-propynyl) adipate, (2-cyanoethyl)(2-propynyl) adipate, 2-(cyanoethyl)(1-methyl-2-propynyl) adipate, (2-cyanoethyl)(1,1-dimethyl-2-propynyl) adipate, (3-cyanopropyl)(2-propynyl) adipate, (4-cyanobutyl)(2-propynyl) adipate, (1,1-dimethylcyanomethyl)(2-propynyl) adipate, cyanomethyl(2-propynyl) pimelate, (2-cyanoethyl)(2-propynyl) pimelate, 2-(cyanoethyl)(1-methyl-2-propynyl) pimelate, (2-cyanoethyl)(1,1-dimethyl-2-propynyl) pimelate, (3-cyanopropyl)(2-propynyl) pimelate, (4-cyanobutyl)(2-propynyl) pimelate, (1,1-dimethylcyanomethyl)(2-propynyl) pimelate, (2-cyanoethyl)(2-propynyl) suberate, (1,1-dimethylcyanomethyl)(2-propynyl) suberate, 1-cyanomethyl 4-(2-propynyl) 2-methylsuccinate, 1-(2-cyanoethyl) 4-(2-propynyl) 2-methylsuccinate, 1-(2-cyanoethyl) 4-(1-methyl-2-propynyl) 2-methylsuccinate, 1-(2-cyanoethyl) 4-(1,1-dimethyl-2-propynyl) 2-methylsuccinate, 1-(3-cyanopropyl) 4-(2-propynyl) 2-methylsuccinate, 1-(4-cyanobutyl) 4-(2-propynyl) 2-methylsuccinate, 1-(1,1-dimethylcyanomethyl) 4-(2-propynyl) 2-methylsuccinate, 1-cyanomethyl 4-(2-propynyl) 3-methylsuccinate, 1-(2-cyanoethyl) 4-(2-propynyl) 3-methylsuccinate, 1-(2-cyanoethyl) 4-(1-methyl-2-propynyl) 3-methylsuccinate, 1-(2-cyanoethyl) 4-(1,1-dimethyl-2-propynyl) 3-methylsuccinate, 1-(3-cyanopropyl) 4-(2-propynyl) 3-methylsuccinate, 1-(4-cyanobutyl) 4-(2-propynyl) 3-methylsuccinate, 1-(1,1-dimethylcyanomethyl) 4-(2-propynyl) 3-methylsuccinate, 1-cyanomethyl 5-(2-propynyl) 2-methylglutarate, 1-(2-cyanoethyl) 5-(2-propynyl) 2-methylglutarate, 1-(2-cyanoethyl) 5-(1-methyl-2-propynyl) 2-methylglutarate, 1-(2-cyanoethyl) 5-(1,1-dimethyl-2-propynyl) 2-methylglutarate, 1-(3-cyanopropyl) 5-(2-propynyl) 2-methylglutarate, 1-(4-cyanobutyl) 5-(2-propynyl) 2-methylglutarate, (1,1-dimethylcyanomethyl) 5-(2-propynyl)$_{2-1}$-methylglutarate, 1-cyanomethyl 5-(2-propynyl) 4-methylglutarate, 1-(2-cyanoethyl) 5-(2-propynyl) 4-methylglutarate, 1-(2-cyanoethyl) 5-(1-methyl-2-propynyl) 4-methylglutarate, 1-(2-cyanoethyl) 5-(1,1-dimethyl-2-propynyl) 4-methylglutarate, 1-(3-cyanopropyl) 5-(2-propynyl) 4-methylglutarate, 1-(4-cyanobutyl) 5-(2-propynyl) 4-methylglutarate, 1-(1,1-dimethylcyanomethyl) 5-(2-propynyl) 4-methylglutarate, 1-cyanomethyl 6-(2-propynyl) 2-methyladipate, 1-(2-cyanoethyl) 6-(2-propynyl) 2-methyladipate, 1-(2-cyanoethyl) 6-(1-methyl-2-propynyl) 2-methyladipate, 1-(2-cyanoethyl) 6-(1,1-dimethyl-2-propynyl) 2-methyladipate, 1-(3-cyanopropyl) 6-(2-propynyl) 2-methyladipate, 1-(4-cyanobutyl) 6-(2-propynyl) 2-methyladipate, (1,1-dimethylcyanomethyl) 6-(2-propynyl) 2-methyladipate, 1-cyanomethyl 6-(2-propynyl) 5-methyladipate, 1-(2-cyanoethyl) 6-(2-propynyl) 5-methyladipate, 1-(2-cyanoethyl) 6-(1-methyl-2-propynyl) 5-methyladipate, 1-(2-cyanoethyl) 6-(1,1-dimethyl-2-propynyl) 5-methyladipate, 1-(3-cyanopropyl) 6-(2-propynyl) 5-methyladipate, 1-(4-cyanobutyl) 6-(2-propynyl) 5-methyladipate, 1-(1,1-dimethylcyanomethyl) 6-(2-propynyl) 2-methyladipate.

Of the above-mentioned compounds, more preferred are carboxylic diesters in which the main chain is a linear alkylene group, such as (2-cyanoethyl)(2-propynyl)succinate, (2-cyanoethyl)(1-methyl-2-propynyl)succinate, (2-cyanoethyl)(2-propynyl) glutarate, (2-cyanoethyl)(1-methyl-2-propynyl) glutarate, (2-cyanoethyl)(2-propynyl) adipate, (2-cyanoethyl)(1-methyl-2-propynyl) adipate, etc., and carboxylic diesters in which the main chain is a branched alkylene group, such as 1-(2-cyanoethyl) 4-(2-propynyl 2-methylsuccinate, 1-cyanomethyl 4-(2-propynyl) 3-methylsuccinate, 1-(2-cyanoethyl) 5-(2-propynyl) 2-methylglutarate, 1-(2-cyanoethyl) 5-(2-propynyl) 4-methylglutarate, 1-(2-cyanoethyl) 6-(2-propynyl) 2-methyladipate, 1-(2-cyanoethyl) 6-(2-propynyl) 5-methyladipate, etc., from the viewpoint of improving low-temperature cycle properties.

In case where $X^{31}$ is -A$^2$-C(=O)O-A$^3$-C≡N and $Y^1$ is N, preferred are dicyanomethyl succinate, di(2-cyanoethyl)succinate, di(3-cyanopropyl)succinate, di(4-cyanobutyl)succinate, di(1,1-dimethylcyanomethyl)succinate, dicyanomethyl glutarate, di(2-cyanoethyl) glutarate, di(3-cyanopropyl) glutarate, di(4-cyanobutyl) glutarate, di(1,1-dimethylcyanomethyl) glutarate, dicyanomethyl adipate, di(2-cyanoethyl) adipate, di(3-cyanopropyl) adipate, di(4-cyanobutyl) adipate, di(1,1-dimethylcyanomethyl) adipate, di(2-cyanoethyl) pimelate, di(1,1-dimethylcyanomethyl) pimelate, di(2-cyanoethyl) suberate, di(1,1-dimethylcyanomethyl) suberate, di(2-cyanoethyl) 2-methylsuccinate, di(1,1-dimethylcyanomethyl) 2-methylsuccinate, di(2-cyanoethyl) 2-methylglutarate, di(1,1-dimethylcyanomethyl) 2-methylglutarate, di(2-cyanoethyl) 3-methylglutarate, di(1,1-dimethylcyanomethyl) 3-methylglutarate, di(2-cyanoethyl) 2-methyladipate, di(1,1-dimethylcyanomethyl) 2-methyladipate, di(2-cyanoethyl) 3-methyladipate, di(1,1-dimethylcyanomethyl) 3-methyladipate.

Of the above-mentioned compounds, more preferred are dicarboxylic esters in which the main chain is a linear alkylene group, such as di(2-cyanoethyl)succinate, di(2-cyanoethyl) glutarate, di(2-cyanoethyl) adipate, etc., and dicarboxylic esters in which the main chain is a branched alkylene group, such as di(2-cyanoethyl) 2-methylsuccinate, di(2-cyanoethyl 2-methylglutarate, di(2-cyanoethyl) 2-methyladipate, etc., from the viewpoint of improving low-temperature cycle properties.

In case where $X^{31}$ is -A$^2$-C(=O)O-A$^4$ and $Y^1$ is CH, preferred are methyl(2-propynyl)succinate, methyl(1-methyl-2-propynyl)succinate, (1,1-dimethyl-2-propynyl)methyl succinate, ethyl(2-propynyl)succinate, (2-propynyl)(1-propyl) succinate, (2-propynyl)(2-propyl)succinate, (1-butyl)(2-propynyl)succinate, (2-methyl-2-propyl)(2-propynyl) succinate, methyl(2-propynyl) glutarate, methyl(1-methyl-2-propynyl) glutarate, (1,1-dimethyl-2-propynyl)methyl glutarate, ethyl(2-propynyl) glutarate, (2-propynyl)(1-propyl) glutarate, (2-propynyl)(2-propyl) glutarate, (1-butyl)(2-propynyl) glutarate, (2-methyl-2-propyl)(2-propynyl) glutarate, methyl(2-propynyl) adipate, methyl(1-methyl-2-propynyl) adipate, (1,1-dimethyl-2-propynyl)methyl adipate, ethyl(2-propynyl) adipate, (2-propynyl)(1-propyl) adipate, (2-propynyl)(2-propyl) adipate, (1-butyl)(2-propynyl) adipate, (2-methyl-2-propyl)(2-propynyl) adipate, methyl(2-propynyl) pimelate, ethyl(2-propynyl) pimelate, methyl(2- propynyl) suberate, ethyl(2-propynyl) suberate, 1-methyl 4-(2-propynyl) 2-methylsuccinate, 1-ethyl 4-(2-propynyl) 2-methylsuccinate, 1-methyl 4-(2-propynyl) 3-methylsuccinate, 1-ethyl 4-(2-propynyl) 3-methylsuccinate, 1-methyl 5-(2-propynyl) 2-methylglutarate, 1-ethyl 5-(2-propynyl) 2-methylglutarate, 1-methyl 5-(2-propynyl) 3-methylglutarate, 1-ethyl 5-(2-propynyl) 3-methylglutarate, 1-methyl 5-(2-propynyl) 4-methylglutarate, 1-ethyl 5-(2-propynyl) 4-methylglutarate, 1-methyl 6-(2-propynyl) 2-methyladipate, 1-ethyl 6-(2-propynyl) 2-methyladipate, 1-methyl 6-(2-propynyl) 5-methyladipate, 1-ethyl 6-(2-propynyl) 5-methyladipate.

Of the above-mentioned compounds, more preferred are dicarboxylic diesters in which the main chain is a linear alkylene group, such as methyl(2-propynyl)succinate, methyl (2-propynyl) glutarate, methyl(2-propynyl) adipate, etc., and dicarboxylic diesters in which the main chain is a branched alkylene group, such as 1-methyl 4-(2-propynyl) 2-methylsuccinate, 1-methyl 4-(2-propynyl) 3-methylsuccinate, 1-methyl 5-(2-propynyl) 2-methylglutarate, 1-methyl 5-(2-propynyl) 4-methylglutarate, 1-methyl 6-(2-propynyl) 2-methyladipate, 1-methyl 6-(2-propynyl) 5-methyladipate, etc., from the viewpoint of improving low-temperature cycle properties.

In case where $X^{31}$ is -$A^2$-C(=O)O-$A^4$ and $Y^1$ is N, preferred are (cyanomethyl)methyl succinate, (2-cyanoethyl) methyl succinate, (3-cyanopropyl)methyl succinate, (4-cyanobutyl)methyl succinate, (1,1-dimethylcyanomethyl) methyl succinate, (2-cyanoethyl)ethyl succinate, (1,1-dimethylcyanomethyl)ethyl succinate, (2-cyanoethyl)(1-propyl)succinate, (1,1-dimethylcyanomethyl)(1-propyl) succinate, (2-cyanoethyl)(2-propyl)succinate, (1,1-dimethylcyanoethyl)(2-propyl)succinate, (1-butyl)(2-cyanoethyl)succinate, (1-butyl)(1,1-dimethylcyanomethyl) succinate, (2-cyanoethyl)(2-methyl-2-propyl)succinate, (1,1-dimethylcyanomethyl)(2-methyl-2-propyl)succinate, (cyanomethyl)methyl glutarate, (2-cyanoethyl)methyl glutarate, (3-cyanopropyl)methyl succinate, (4-cyanobutyl)methyl glutarate, (1,1-dimethylcyanomethyl)methyl glutarate, (2-cyanoethyl)ethyl glutarate, (1,1-dimethylcyanomethyl) ethyl glutarate, (2-cyanoethyl)(1-propyl) glutarate, (1,1-dimethylcyanomethyl)(1-propyl) glutarate, (2-cyanoethyl)(2-propyl)succinate, (1,1-dimethylcyanomethyl)(2-propyl) glutarate, (1-butyl)(2-cyanoethyl) glutarate, (1-butyl)(1,1-dimethylcyanomethyl) glutarate, (2-cyanoethyl)(2-methyl-2-propyl) glutarate, (1,1-dimethylcyanomethyl)(2-methyl-2-propyl) glutarate, (cyanomethyl)methyl adipate, (2-cyanoethyl)methyl adipate, (3-cyanopropyl)methyl adipate, (4-cyanobutyl)methyl adipate, (1,1-dimethylcyanomethyl)methyl adipate, (2-cyanoethyl)ethyl adipate, (1,1-dimethylcyanomethyl)ethyl adipate, (2-cyanoethyl)(1-propyl) adipate, (1,1-dimethylcyanomethyl)(1-propyl) adipate, (2-cyanoethyl)(2-propyl) adipate, (1,1-dimethylcyanomethyl)(2-propyl) adipate, (1-butyl)(2-cyanoethyl) adipate, (1-butyl)(1,1-dimethylcyanomethyl) adipate, (2-cyanoethyl)(2-methyl-2-propyl) adipate, (1,1-dimethylcyanomethyl)(2-methyl-2-propyl) adipate, (2-cyanoethyl)methyl pimelate, (1,1-dimethylcyanomethyl)methyl pimelate, (2-cyanoethyl) ethyl pimelate, (1,1-dimethylcyanomethyl)ethyl pimelate, (2-cyanoethyl)methyl suberate, (1,1-dimethylcyanomethyl) methyl suberate, (2-cyanoethyl)ethyl suberate, (1,1-dimethylcyanomethyl)ethyl suberate, 1-(2-cyanoethyl) 4-methyl 2-methylsuccinate, 1-(1,1-dimethylcyanomethyl) 4-methyl 2-methylsuccinate, 1-(2-cyanoethyl) 4-ethyl 2-methylsuccinate, 1-(1,1-dimethylcyanomethyl) 4-ethyl 2-methylsuccinate, 1-(2-cyanoethyl) 4-methyl 3-methylsuccinate, 1-(1,1-dimethylcyanomethyl) 4-methyl 3-methylsuccinate, 1-(2-cyanoethyl) 4-ethyl 3-methylsuccinate, 1-(1,1-dimethylcyanomethyl) 4-ethyl 3-methylsuccinate, 1-(2-cyanoethyl) 5-methyl 2-methylglutarate, 1-(1,1-dimethylcyanomethyl) 5-methyl 2-methylglutarate, 1-(2-cyanoethyl) 5-ethyl 2-methylglutarate, 1-(1,1-dimethylcyanomethyl) 5-ethyl 2-methylglutarate, 1-(2-cyanoethyl) 5-methyl 3-methylglutarate, 1-(1,1-dimethylcyanomethyl) 5-methyl 3-methylglutarate, 1-(2-cyanoethyl) 5-ethyl 3-methylglutarate, 1-(1,1-dimethylcyanomethyl) 5-ethyl 3-methylglutarate, 1-(2-cyanoethyl) 5-methyl 4-methylglutarate, 1-(1,1-dimethylcyanomethyl) 5-methyl 4-methylglutarate, 1-(2-cyanoethyl) 5-ethyl 4-methylglutarate, 1-(1,1-dimethylcyanomethyl) 5-ethyl 4-methylglutarate, 1-(2-cyanoethyl) 6-methyl 2-methyladipate, 1-(1,1-dimethylcyanomethyl) 6-methyl 2-methyladipate, 1-(2-cyanoethyl) 6-ethyl 2-methyladipate, 1-(1,1-dimethylcyanomethyl) 6-ethyl 2-methyladipate, 1-(2-cyanoethyl) 6-methyl 5-methyladipate, 1-(1,1-dimethylcyanomethyl) 6-methyl 5-methyladipate, 1-(2-cyanoethyl) 6-ethyl 5-methyladipate, 1-(1,1-dimethylcyanomethyl) 6-ethyl 5-methyladipate.

Of the compounds represented by the general formula (III-I), preferred are dicarboxylic diesters in which the main chain is a linear alkylene group and dicarboxylic diesters in which the main chain is a branched alkyl group, from the viewpoint of improving low-temperature cycle properties, and concretely, more preferred are one or more selected from 2-propynyl 3-butynoate, 1-methyl-2-propynyl 3-butynoate, 1,1-dimethyl-2-propynyl 3-butynoate, 2-cyanoethyl 3-butynoate, 3-cyanopropyl 3-butynoate, 4-cyanobutyl 3-butynoate, 2-propynyl 3-cyanopropionate, 2-propynyl 4-cyanobutanoate, 2-propynyl 5-cyanovalerate, 1-methyl-2-propynyl 5-cyanovalerate, 1,1-dimethyl-2-propynyl 5-cyanovalerate, 2-propynyl 3-cyano-2-methylpropionate, 2-propynyl 3-cyano-3-methylpropionate, 2-cyanoethyl 3-cyanopropionate, 2-cyanoethyl 4-cyanobutanoate, 2-cyanoethyl 5-cyanovalerate, 2-cyanoethyl 3-cyano-2-methylpropionate, 2-cyanoethyl 3-cyano-3-methylpropionate, di(2-propynyl)succinate, di(2-propynyl) glutarate, di(2-propynyl) adipate, di(2-propynyl) pimelate, di(2-propynyl) 2-methylsuccinate, di(2-propynyl) 2-methylglutarate, di(2-propynyl) 3-methylglutarate, di(2-propynyl) 2-methyladipate, di(2-propynyl) 3-methyladipate, (2-cyanoethyl)(2-propynyl)succinate, (2-cyanoethyl)(1-methyl-2-propynyl)succinate, di(2-cyanoethyl)succinate, di(2-cyanoethyl) glutarate, di(2-cyanoethyl) adipate, di(2-cyanoethyl) 2-methylsuccinate, methyl(2-propynyl)succinate, (2-cyanoethyl)methyl succinate, and (2-cyanoethyl)ethyl succinate.

Of those, most preferred are one or more selected from 2-propynyl 3-butynoate, 2-cyanoethyl 3-butynoate, 2-propynyl 3-cyanopropionate, 2-propynyl 4-cyanobutanoate, 2-propynyl 5-cyanovalerate, 2-cyanoethyl 3-cyanopropionate, 2-cyanoethyl 4-cyanobutanoate, 2-cyanoethyl 5-cyanovalerate, di(2-propynyl)succinate, di(2-propynyl) glutarate, di(2-propynyl) adipate, di(2-propynyl) 2-methylsuccinate, (2-cyanoethyl)(2-propynyl)succinate, di(2-cyanoethyl)succinate, di(2-cyanoethyl) glutarate, di(2-cyanoethyl) adipate, di(2-cyanoethyl) 2-methylsuccinate, methyl(2-propynyl)succinate, (2-cyanoethyl)methyl succinate, and (2-cyanoethyl) ethyl succinate.

The content of the carboxylate represented by the general formula (III-I) to be contained in the nonaqueous electrolytic solution of the present invention is from 0.01 to 5% by mass therein. In case where the content is more than 5% by mass, a surface film may be formed excessively on an electrode to worsen low-temperature cycle properties; but when the content is less than 0.01% by mass, then the surface film formation would be insufficient, therefore failing in attaining the effect of improving low-temperature cycle properties. The content is preferably at least 0.05% by mass in the nonaqueous electrolytic solution, more preferably at least 0.5% by mass, even more preferably at least 1% by mass; and its upper limit is preferably at most 5% by mass, more preferably at most 3% by mass, even more preferably at most 2% by mass.

In the nonaqueous electrolytic solution of the present invention, the carboxylate represented by the general formula (III-I), as added thereto, may improve low-temperature cycle properties; however, when combined with a nonaqueous solvent, an electrolyte salt and further other additives to be mentioned below, the ester can exhibit a specific effect of synergistically improving low-temperature cycle properties. Though the reason is not always clear, it may be considered that a mixture surface film having a high ionic conductivity and comprising the constitutive elements of the nonaqueous solvent, electrolyte salt and other additives could be formed.

[The Fourth Nonaqueous Electrolytic Solution]

The fourth nonaqueous electrolytic solution of the present invention comprises an electrolyte salt dissolved in a nonaqueous solvent and contains a carboxylate represented by the following general formula (IV-I) in an amount of from 0.01 to 10% by mass of the nonaqueous electrolytic solution.

[Chemical Formula 19]

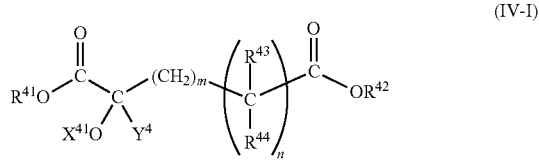

(IV-I)

(In the formula, $R^{41}$ and $R^{42}$ each independently represent an alkyl group having from 1 to 6 carbon atoms, an alkenyl group having from 2 to 7 carbon atoms, an alkynyl group having from 3 to 8 carbon atoms, or a cycloalkyl group having from 3 to 8 carbon atoms; $R^{43}$ represents a hydrogen atom, or an alkyl group having from 1 to 6 carbon atoms; $R^{44}$ represents a hydrogen atom, an alkyl group having from 1 to 6 carbon atoms, or $CH_2COOR^{45}$; $X^{41}$ represents an alkyl group having from 1 to 6 carbon atoms, a formyl group, an acyl group having from 2 to 7 carbon atoms, an alkoxycarbonyl group having from 2 to 7 carbon atoms, an alkanesulfonyl group having from 1 to 6 carbon atoms, an aryl group having from 6 to 12 carbon atoms, an alkylsilyl group having from 3 to 18 carbon atoms, a dialkylphosphoryl group having from 2 to 12 carbon atoms, an alkoxy(alkyl)phosphoryl group having from 2 to 12 carbon atoms, or a dialkoxyphosphoryl group having from 2 to 12 carbon atoms; $Y^4$ represents a hydrogen atom, —$CH_2COOR^{46}$ or an alkyl group having from 1 to 6 carbon atoms; $R^{45}$ and $R^{46}$ each independently represent an alkyl group having from 1 to 6 carbon atoms, an alkenyl group having from 2 to 7 carbon atoms, an alkynyl group having from 3 to 8 carbon atoms, a cycloalkyl group having from 3 to 8 carbon atoms; m indicates an integer of from 0 to 4; n indicates 0 or 1; at least one hydrogen atom on the carbon atoms of $R^{41}$, $R^{42}$, $R^{45}$ and $R^{46}$ may be substituted with a halogen atom, an alkoxy group having from 1 to 4 carbon atoms, or a nitrile group.)

Though not always clear, the reason why the fourth nonaqueous electrolytic solution can greatly improve low-temperature load characteristics after high-temperature charging storage may be considered as follows:

The carboxylate represented by the general formula (IV-I) and contained in the nonaqueous electrolytic solution of the present invention has at least two carboxylate moieties in the structure thereof, and therefore, on a negative electrode, the two carboxylate moieties contribute toward the reaction to form a decomposition product hardly soluble in the electrolytic solution, thereby improving charging storage properties at high temperatures. Further, it has been known that the carboxylate in the present invention is a compound having, as the linking group to link the two carboxylate moieties therein, a specific functional group quite differing from the carboxylate and therefore exhibits a specific effect of significantly improving low-temperature load characteristics after high-temperature charging storage.

The halogen atom with which the hydrogen atom on the carbon atom of the substituents $R^{41}$, $R^{42}$, $R^{45}$ and $R^{46}$ in the general formula (IV-I) includes a fluorine atom, a chlorine atom, a bromine atom and an iodine atom, but is preferably a fluorine atom or a chlorine atom, more preferably a fluorine atom.

The linear alkyl group having from 1 to 6 carbon atoms of the substituents $R^{41}$ and $R^{42}$ in the general formula (IV-I) is preferably a methyl group, an ethyl group, a propyl group, a butyl group, a pentyl group or a hexyl group; and the branched alkyl group thereof is preferably an isopropyl group, a sec-butyl group, a tert-butyl group or a tert-amyl group.

The linear alkenyl group having from 2 to 7 carbon atoms is preferably a vinyl group, a 2-propenyl group, a 2-butenyl group, a 3-butenyl group or a 4-butenyl group; the branched alkyl group is preferably a 2-methyl-2-propenyl group, a 2-methyl-2-butenyl group or a 3-methyl-2-butenyl group.

The linear alkynyl group having from 3 to 8 carbon atoms is preferably a 2-propynyl group, a 2-butynyl group, a 3-butynyl group, a 4-pentynyl group or a 5-hexynyl group; and the branched alkynyl group is preferably a 1-methyl-2-propynyl group, a 1-methyl-2-butynyl group or a 1,1-dimethyl-2-propynyl group.

The cycloalkyl group having from 3 to 8 carbon atoms is preferably a cyclopropyl group, a cyclobutyl group, a cyclopentyl group, a cyclohexyl group or a cycloheptyl group.

The group of $R^{41}$ or $R^{42}$ in which at least one hydrogen atom on the carbon atoms is substituted with a halogen atom, an alkoxy group having from 1 to 4 carbon atoms or a nitrile group is preferably a 2,2,2-trifluoroethyl group, a 2-methoxyethyl group, a 3-methoxypropyl group, a 2-ethoxyethyl group, a cyanomethyl group, a 2-cyanoethyl group or a 3-cyanopropyl group.

Of the above-mentioned substituents, preferred are an alkyl group having from 1 to 4 carbon atoms, an alkenyl group having from 2 to 5 carbon atoms, and an alkynyl group having from 3 to 5 carbon atoms.

Of those, more preferred for $R^{41}$ and $R^{42}$ are a methyl group, an ethyl group and a 2-propynyl group, and even more preferred are a methyl group and a 2-propynyl group.

$R^{43}$ is a hydrogen atom or an alkyl group having from 1 to 6 carbon atoms; and the alkyl group is preferably a methyl group, an ethyl group, a propyl group, a butyl group, a pentyl group or a hexyl group. Of those, more preferred is a hydrogen atom or a methyl group.

$R^{44}$ is a hydrogen atom, an alkyl group having from 1 to 6 carbon atoms, or $CH_2COOR^{45}$. The alkyl group is preferably a methyl group, an ethyl group, a propyl group, a butyl group, a pentyl group or a hexyl group. Of those, more preferred is a methyl group, an ethyl group or a propyl group, and even more preferred is a methyl group or an ethyl group.

$R^{45}$ in —$CH_2COOR^{45}$ has the same meaning as that of $R^{41}$ or $R^{42}$.

The substituent $X^{41}$ is a linear or branched alkyl group having from 1 to 6 carbon atoms, a formyl group, a linear or branched acyl group having from 2 to 7 carbon atoms, a linear or branched alkoxycarbonyl group having from 2 to 8 carbon atoms, a linear or branched alkanesulfonyl group having from 1 to 6 carbon atoms, a linear or branched alkylsilyl group having from 3 to 18 carbon atoms, a dialkylphosphoryl group having from 2 to 12 carbon atoms, an alkoxy(alkyl)phosphoryl group having from 2 to 12 carbon atoms, or a dialkoxyphosphoryl group having from 2 to 12 carbon atoms.

The alkyl group is preferably a methyl group, an ethyl group, a propyl group, a butyl group, a pentyl group or a hexyl group. Of those, preferred is a methyl group, an ethyl group or a propyl group, and more preferred is a methyl group or an ethyl group.

The acyl group is preferably an acetyl group, a propionyl group, a butyryl group, an isobutyryl group, a pivaloyl group, etc. Of those, more preferred are an acetyl group and a propionyl group; and even more preferred is an acetyl group.

The linear or branched alkoxycarbonyl group having from 2 to 8 carbon atoms of the substituent $X^{41}$ is preferably a methoxycarbonyl group, an ethoxycarbonyl group, a propoxycarbonyl group, an isopropoxycarbonyl group, a butoxycarbonyl group, etc. Of those, more preferred are a methoxycarbonyl group, and an ethoxycarbonyl group; and even more preferred is a methoxycarbonyl group.

The linear or branched alkanesulfonyl group having from 1 to 6 carbon atoms of the substituent $X^{41}$ is preferably a methanesulfonyl group, an ethanesulfonyl group, a propanesulfonyl group, a butanesulfonyl group, a pentanesulfonyl group, a hexanesulfonyl group, a trifluoromethanesulfonyl group, a 2,2,2-trifluoroethanesulfonyl group, a 2-propanesulfonyl group, a 2,2-dimethylethanesulfonyl group, etc. Of those, more preferred are a methanesulfonyl group, an ethanesulfonyl group and a trifluoromethanesulfonyl group; and even more preferred is a methanesulfonyl group.

The arylsulfonyl group having from 6 to 12 carbon atoms of the substituent $X^{41}$ is preferably a benzenesulfonyl group, a 4-methylbenzenesulfonyl group, a 4-methylbenzenesulfonyl group, a 2,4,6-trimethylbenzenesulfonyl group, a 4-fluorobenzenesulfonyl group, a 4-trifluorobenzenesulfonyl group, etc. Of those, more preferred are a benzenesulfonyl group, and a 4-methylbenzenesulfonyl group; and more preferred is a 4-methylbenzenesulfonyl group.

The linear or branched alkylsilyl group having from 3 to 18 carbon atoms of the substituent $X^{41}$ is preferably a trimethylsilyl group, a triethylsilyl group, a tripropylsilyl group, a tributylsilyl group, a tert-butyldimethylsilyl group, etc. Of those, more preferred are a trimethylsilyl group and a triethylsilyl group; and even more preferred is a trimethylsilyl group.

The dialkylphosphoryl group having from 2 to 12 carbon atoms of the substituent $X^{41}$ in the general formula (IV-I) is preferably a dimethylphosphoryl group, a diethylphosphoryl group, a dipropylphosphoryl group, a dibutylphosphoryl group, etc. Of those, more preferred are a dimethylphosphoryl group and a diethylphosphoryl group.

The alkoxy(alkyl)phosphoryl group having from 2 to 12 carbon atoms is preferably a methoxy(methyl)phosphoryl group, an ethoxy(ethyl)phosphoryl group, a propyl(propyloxy)phosphoryl group, a butoxy(butyl)phosphoryl group, an ethoxy(methyl)phosphoryl group, an ethyl(methoxy)phosphoryl group, etc. Of those, more preferred are a methoxy (methyl)phosphoryl group, and an ethoxy(ethyl)phosphoryl group.

The dialkoxyphosphoryl group having from 2 to 12 carbon atoms is preferably a dimethoxyphosphoryl group, a diethoxyphosphoryl group, a dipropoxyphosphoryl group, a dibutoxyphosphoryl group. Of those, more preferred are a dimethoxyphosphoryl group and a diethoxyphosphoryl group.

More preferred examples of the substituent $X^{41}$ in the general formula (IV-I) are those selected from an alkanesulfonyl group, an arylsulfonyl group, a dialkylphosphoryl group, an alkoxy(alkyl)phosphoryl group, a dialkoxyphosphoryl group, a formyl group, an acyl group, an alkoxycarbonyl group and an alkylsilyl group; more preferred are those selected from an alkanesulfonyl group, an arylsulfonyl group, a dialkylphosphoryl group, an alkoxy(alkyl)phosphoryl group, a dialkoxyphosphoryl group, a formyl group and an alkoxycarbonyl group; and even more preferred are those selected from an alkanesulfonyl group, an arylsulfonyl group, a dialkylphosphoryl group, an alkoxy(alkyl)phosphoryl group and a dialkoxyphosphoryl group.

In the general formula (IV-I), the substituent $Y^4$ is a hydrogen atom, an alkyl group having from 1 to 6 carbon atoms or —$CH_2COOR^{46}$.

The alkyl group is preferably a methyl group, an ethyl group, a propyl group, a butyl group, a pentyl group, or a hexyl group. Of those, more preferred are a methyl group, an ethyl group and a propyl group; and even more preferred are a methyl group and an ethyl group.

$R^{46}$ in —$CH_2COOR^{46}$ has the same meaning as that of $R^{41}$ or $R^{42}$.

More preferably, the substituent $Y^4$ in the general formula (IV-I) is a hydrogen atom or —$CH_2COOR^{46}$, even more preferably a hydrogen atom.

In the general formula (IV-I), m indicates an integer of from 0 to 4, but is preferably an integer of from 1 to 3, more preferably 1 or 2; and n indicates 0 or 1, but is preferably 0.

The compound of the general formula (IV-I) preferably has 2 or 3 carboxylate groups, more preferably 2 carboxylate groups.

Preferably, the compound has the above-mentioned substituents and the structure, as more effective for improving low-temperature properties after high-temperature charging storage.

Specific examples of the compound represented by the general formula (IV-I) are as follows:

(i) In case where m=1 and n=0 (as succinate type):

Preferably mentioned are dimethyl 2-methoxysuccinate, diethyl 2-methoxysuccinate, divinyl 2-methoxysuccinate, di(2-propenyl) 2-methoxysuccinate, di(2-propynyl) 2-methoxysuccinate, dimethyl 2-ethoxysuccinate, diethyl 2-ethoxysuccinate, divinyl 2-ethoxysuccinate, di(2-propenyl) 2-ethoxysuccinate, di(2-propynyl) 2-ethoxysuccinate, dimethyl 2-(formyloxy)succinate, diethyl 2-(formyloxy)succinate, divinyl 2-(formyloxy)succinate, di(2-propenyl) 2-(formyloxy)succinate, di(2-propynyl) 2-(formyloxy)succinate, di(2,2,2-trifluoroethyl) 2-(formyloxy)succinate, di(2-methoxyethyl) 2-(formyloxy)succinate, di(2-ethoxyethyl) 2-(formyloxy)succinate, di(cyanomethyl) 2-(formyloxy)succinate, di(2-cyanoethyl) 2-(formyloxy)succinate, di(3-cyanopropyl) 2-(formyloxy)succinate, dimethyl 2-(acetyloxy) succinate, diethyl 2-(acetyloxy)succinate, divinyl 2-(acetyloxy)succinate, di(2-propenyl) 2-(acetyloxy)succinate, di(2-propynyl) 2-(acetyloxy)succinate, dimethyl 2-(propionyloxy)succinate, diethyl 2-(propionyloxy)succinate, divinyl 2-(propionyloxy)succinate, di(2-propenyl) 2-(propionyloxy)succinate, di(2-propynyl) 2-(propionyloxy) succinate, dimethyl 2-(methoxycarbonyloxy)succinate, diethyl 2-(methoxycarbonyloxy)succinate, divinyl 2-(methoxycarbonyloxy)succinate, di(2-propenyl) 2-(methoxycarbonyloxy)succinate, di(2-propynyl) 2-(methoxycarbonyloxy)succinate, dimethyl 2-(ethoxycarbonyloxy)succinate, diethyl 2-(ethoxycarbonyloxy)succinate, divinyl 2-(ethoxycarbonyloxy)succinate, di(2-propenyl) 2-(methoxycarbonyloxy)succinate, di(2-propynyl) 2-(ethoxycarbonyloxy)succinate, dimethyl 2-(methanesulfonyloxy)succinate, diethyl 2-(methanesulfonyloxy)succinate, divinyl 2-(methanesulfonyloxy)succinate, di(2-propenyl) 2-(methanesulfonyloxy)succinate, di(2-propynyl) 2-(methanesulfonyloxy)succinate, di(2,2,2-trifluoroethyl) 2-(methanesulfonyloxy)succinate, di(2-methoxyethyl) 2-(methanesulfonyloxy)succinate, di(2-ethoxyethyl) 2-(methanesulfonyloxy)succinate, di(cyanomethyl) 2-(methanesulfonyloxy)succinate, di(2-cyanoethyl) 2-(methanesulfonyloxy)succinate, di(3-cyanopropyl) 2-(methanesulfonyloxy)succinate, dimethyl 2-(ethanesulfonyloxy)succinate, diethyl 2-(ethanesulfonyloxy)succinate, divinyl 2-(ethanesulfonyloxy)succinate, di(2-propenyl) 2-(ethanesulfonyloxy)succinate, di(2-propynyl) 2-(ethanesulfonyloxy)succinate, dimethyl 2-(benzenesulfonyloxy)succinate, di(2-propenyl) 2-(benzenesulfonyloxy)succinate, di(2-propynyl) 2-(benzenesulfonyloxy)succinate, dimethyl 2-(4-methylbenzenesulfonyloxy)succinate, di(2-propenyl) 2-(4-methylbenzenesulfonyloxy)succinate, di(2-propynyl) 2-(4-methylbenzenesulfonyloxy)succinate, dimethyl 2-(trimethylsilyloxy)succinate, diethyl 2-(trimethylsilyloxy)succinate, divinyl 2-(trimethylsilyloxy)succinate, di(2-propenyl) 2-(trimethylsilyloxy)succinate, di(2-propynyl) 2-(trimethylsilyloxy)succinate, dimethyl 2-(triethylsilyloxy)succinate, diethyl 2-(triethylsilyloxy)succinate, divinyl 2-(triethylsilyloxy)succinate, di(2-propenyl) 2-(triethylsilyloxy)succinate, di(2-propynyl) 2-(triethylsilyloxy)succinate, dimethyl 2-(dimethylphosphoryloxy)succinate, diethyl 2-(dimethylphosphoryloxy)succinate, divinyl 2-(dimethylphosphoryloxy)succinate, di(2-propenyl) 2-(dimethylphosphoryloxy)succinate, di(2-propynyl) 2-(dimethylphosphoryloxy)succinate, dimethyl 2-(diethylphosphoryloxy)succinate, diethyl 2-(diethylphosphoryloxy)succinate, divinyl 2-(diethylphosphoryloxy)succinate, di(2-propenyl) 2-(diethylphosphoryloxy)succinate, di(2-propynyl) 2-(diethylphosphoryloxy)succinate, dimethyl 2-[(methoxy)methylphosphoryloxy]succinate, diethyl 2-[(methoxy)methylphosphoryloxy]succinate, divinyl 2-[(methoxy)methylphosphoryloxy]succinate, di(2-propenyl) 2-[(methoxy)methylphosphoryloxy]succinate, di(2-propynyl) 2-[(methoxy)methylphosphoryloxy]succinate, dimethyl 2-[(ethoxy)ethylphosphoryloxy]succinate, diethyl 2-[(ethoxy)ethylphosphoryloxy]succinate, divinyl 2-[(ethoxy)ethylphosphoryloxy]succinate, di(2-propenyl) 2-[(ethoxy)ethylphosphoryloxy]succinate, di(2-propynyl) 2-[(ethoxy)ethylphosphoryloxy]succinate, dimethyl 2-(dimethoxyphosphoryloxy)succinate, diethyl 2-(dimethoxyphosphoryloxy)succinate, divinyl 2-(dimethoxyphosphoryloxy)succinate, di(2-propenyl) 2-(dimethoxyphosphoryloxy)succinate, di(2-propynyl) 2-(dimethoxyphosphoryloxy)succinate, di(2,2,2-trifluoroethyl) 2-(dimethoxyphosphoryloxy)succinate, di(2-methoxyethyl) 2-(dimethoxyphosphoryloxy)succinate, di(2-ethoxyethyl) 2-(dimethoxyphosphoryloxy)succinate, di(cyanomethyl) 2-(dimethoxyphosphoryloxy)succinate, di(2-cyanoethyl) 2-(dimethoxyphosphoryloxy)succinate, di(3-cyanopropyl) 2-(dimethoxyphosphoryloxy)succinate, dimethyl 2-(diethoxyphosphoryloxy)succinate, diethyl 2-(diethoxyphosphoryloxy)succinate, divinyl 2-(diethoxyphosphoryloxy)succinate, di(2-propenyl) 2-(diethoxyphosphoryloxy)succinate, di(2-propynyl) 2-(diethoxyphosphoryloxy)succinate, di(2,2,2-trifluoroethyl) 2-(diethoxyphosphoryloxy)succinate, di(2-methoxyethyl) 2-(diethoxyphosphoryloxy)succinate, di(2-ethoxyethyl) 2-(diethoxyphosphoryloxy)succinate, di(cyanomethyl) 2-(diethoxyphosphoryloxy)succinate, di(2-cyanoethyl) 2-(diethoxyphosphoryloxy)succinate, di(3-cyanopropyl) 2-(dimethoxyphosphoryloxy)succinate, di(3-cyanopropyl) 2-(diethoxyphosphoryloxy)succinate.

(ii) In case where m=1, n=0 and Y=methyl (as 2-methylsuccinate type):

Preferably mentioned are dimethyl 2-methoxy-2-methylsuccinate, di(2-propynyl) 2-methoxy-2-methylsuccinate, dimethyl 2-(formyloxy)-2-methylsuccinate, di(2-propynyl) 2-(formyloxy)-2-methylsuccinate, dimethyl 2-(acetyloxy)-2-methylsuccinate, di(2-propynyl) 2-(acetyloxy)-2-methylsuccinate, dimethyl 2-(methoxycarbonyloxy)-2-methylsuccinate, di(2-propynyl) 2-(methoxycarbonyloxy)-2-methylsuccinate, dimethyl 2-(methanesulfonyloxy)-2-methylsuccinate, di(2-propynyl) 2-(methanesulfonyloxy)-2-methylsuccinate, dimethyl 2-(benzenesulfonyloxy)-2-methylsuccinate, di(2-propynyl) 2-(benzenesulfonyloxy)-2-methylsuccinate, dimethyl 2-(4-methylbenzenesulfonyloxy)-2-methylsuccinate, di(2-propynyl) 2-(4-methylbenzenesulfonyloxy)-2-methylsuccinate, dimethyl 2-methyl-2-(trimethylsilyloxy)succinate, di(2-propynyl) 2-methyl-2-(trimethylsilyloxy)succinate, dimethyl 2-(dimethylphosphoryloxy)-2-methylsuccinate, di(2-propynyl) 2-(dimethylphosphoryloxy)-2-methylsuccinate, dimethyl 2-[(methoxy)methylphosphoryloxy]-2-methylsuccinate, di(2-propynyl) 2-[(methoxy)methylphosphoryloxy]-2-methylsuccinate, dimethyl 2-(dimethoxyphosphoryloxy)-2-methylsuccinate, di(2-propynyl) 2-(dimethoxyphosphoryloxy)-2-methylsuccinate, dimethyl 2-(diethoxyphosphoryloxy)-2-methylsuccinate, di(2-propynyl) 2-(diethoxyphosphoryloxy)-2-methylsuccinate.

(iii) In case where m=0 and n=0 (as malonate type):

Preferably mentioned are dimethyl 2-methoxymalonate, di(2-propynyl) 2-methoxymalonate, dimethyl 2-(formyloxy)malonate, di(2-propynyl) 2-(formyloxy)malonate, dimethyl 2-(acetyloxy)malonate, di(2-propynyl) 2-(acetyloxy)malonate, dimethyl 2-(methoxycarbonyloxy)malonate, di(2-propynyl) 2-(methoxycarbonyloxy)malonate, dimethyl 2-(methanesulfonyloxy)malonate, di(2-propynyl) 2-(methanesulfonyloxy)malonate, dimethyl 2-(benzenesulfonyloxy)malonate, di(2-propynyl) 2-(benzenesulfonyloxy)malonate, dimethyl 2-(4-methylbenzenesulfonyloxy)malonate, di(2-propynyl) 2-(4-methylbenzenesulfonyloxy)malonate, dimethyl 2-(trimethylsilyloxy)malonate, di(2-propynyl) 2-(trimethylsilyloxy)malonate, dimethyl 2-(dimethylphosphoryloxy)malonate, di(2-propynyl) 2-(dimethylphosphoryloxy)malonate, dimethyl 2-[(methoxy)methylphosphoryloxy]malonate, di(2-propynyl) 2-[(methoxy)methylphosphoryloxy]malonate, dimethyl 2-(dimethoxyphosphoryloxy)malonate, di(2-propynyl) 2-(dimethoxyphosphoryloxy)malonate, dimethyl 2-(diethoxyphosphoryloxy)malonate, di(2-propynyl) 2-(diethoxyphosphoryloxy)malonate.

(iv) In case where m=2 and n=0 (as glutarate type):

Preferably mentioned are dimethyl 2-methoxyglutarate, di(2-propynyl) 2-methoxyglutarate, dimethyl 2-(formyloxy)glutarate, di(2-propynyl) 2-(formyloxy)glutarate, dimethyl 2-(acetyloxy)glutarate, di(2-propynyl) 2-(acetyloxy)glutarate, dimethyl 2-(methoxycarbonyloxy)glutarate, (2-propynyl) 2-(methoxycarbonyloxy)glutarate, dimethyl 2-(methanesulfonyloxy)glutarate, di(2-propynyl) 2-(methanesulfonyloxy)glutarate, dimethyl 2-(benzenesulfonyloxy)glutarate, (2-propynyl) 2-(benzenesulfonyloxy)glutarate, dimethyl 2-(4-methylbenzenesulfonyloxy)glutarate, di(2-propynyl) 2-(4-methylbenzenesulfonyloxy) glutarate, dimethyl 2-(trimethylsilyloxy)glutarate, di(2-propynyl) 2-(trimethylsilyloxy)glutarate, dimethyl 2-(dimethylphosphoryloxy)glutarate, di(2-propynyl) 2-(dimethylphosphoryloxy)glutarate, dimethyl 2-[(methoxy)methylphosphoryloxy]glutarate, di(2-propynyl) 2-[(methoxy)methylphosphoryloxy]glutarate, dimethyl 2-(dimethoxyphosphoryloxy)glutarate, di(2-propynyl) 2-(dimethoxyphosphoryloxy)glutarate, dimethyl 2-(diethoxyphosphoryloxy)glutarate, di(2-propynyl) 2-(diethoxyphosphoryloxy)glutarate.

(v) In case where m=1, n=0 and Y=CH$_2$COOR$^{46}$ (as citrate type):

Preferably mentioned are trimethyl 2-methoxypropane-1,2,3-tricarboxylate, tri(2-propynyl) 2-methoxypropane-1,2,3-tricarboxylate, trimethyl 2-(formyloxy)propane-1,2,3-tricarboxylate, tri(2-propynyl) 2-(formyloxy)propane-1,2,3-tricarboxylate, trimethyl 2-(acetyloxy)propane-1,2,3-tricarboxylate, tri(2-propynyl) 2-(acetyloxy)propane-1,2,3-tricarboxylate, trimethyl 2-(methoxycarbonyloxy)propane-1,2,3-tricarboxylate, tri(2-propynyl) 2-(methoxycarbonyloxy)propane-1,2,3-tricarboxylate, trimethyl 2-(methanesulfonyloxy)propane-1,2,3-tricarboxylate, tri(2-propynyl) 2-(methanesulfonyloxy)propane-1,2,3-tricarboxylate, tri(2,2,2-trifluoroethyl) 2-(methanesulfonyloxy)propane-1,2,3-tricarboxylate, tri(2-methoxyethyl) 2-(methanesulfonyloxy)propane-1,2,3-tricarboxylate, tri(cyanomethyl) 2-(methanesulfonyloxy)propane-1,2,3-tricarboxylate, tri(2-cyanoethyl) 2-(methanesulfonyloxy)propane-1,2,3-tricarboxylate, trimethyl 2-(benzenesulfonyloxy)propane-1,2,3-tricarboxylate, tri(2-propynyl) 2-(benzenesulfonyloxy)propane-1,2,3-tricarboxylate, trimethyl 2-(4-methylbenzenesulfonyloxy)propane-1,2,3-tricarboxylate, tri(2-propynyl) 2-(4-methylbenzenesulfonyloxy)propane-1,2,3-tricarboxylate, trimethyl 2-(trimethylsilyloxy)propane-1,2,3-tricarboxylate, tri(2-propynyl) 2-(trimethylsilyloxy)propane-1,2,3-tricarboxylate, trimethyl 2-(dimethylphosphoryloxy)propane-1,2,3-tricarboxylate, tri(2-propynyl) 2-(dimethylphosphoryloxy)propane-1,2,3-tricarboxylate, trimethyl 2-[(methoxy)methylphosphoryloxy]propane-1,2,3-tricarboxylate, tri(2-propynyl) 2-[(methoxy)methylphosphoryloxy]propane-1,2,3-tricarboxylate, dimethyl 2-(dimethoxyphosphoryloxy)glutarate, tri(2-propynyl) 2-(dimethoxyphosphoryloxy)propane-1,2,3-tricarboxylate, trimethyl 2-(diethoxyphosphoryloxy)propane-1,2,3-tricarboxylate, tri(2-propynyl) 2-(diethoxyphosphoryloxy)propane-1,2,3-tricarboxylate.

(vi) In case where m=0, n=1 and R$^{44}$=CH$_2$COOR$^{45}$ (as isocitrate type):

Preferably mentioned are trimethyl 1-methoxypropane-1,2,3-tricarboxylate, tri(2-propynyl) 1-methoxypropane-1,2,3-tricarboxylate, trimethyl 1-(formyloxy)propane-1,2,3-tricarboxylate, tri(2-propynyl) 1-(formyloxy)propane-1,2,3-tricarboxylate, trimethyl 1-(acetyloxy)propane-1,2,3-tricarboxylate, tri(2-propynyl) 1-(acetyloxy)propane-1,2,3-tricarboxylate, trimethyl 1-(methoxycarbonyloxy)propane-1,2,3-tricarboxylate, tri(2-propynyl) 1-(methoxycarbonyloxy)propane-1,2,3-tricarboxylate, trimethyl 1-(methanesulfonyloxy)propane-1,2,3-tricarboxylate, tri(2-propynyl) 1-(methanesulfonyloxy)propane-1,2,3-tricarboxylate, trimethyl 1-(benzenesulfonyloxy)propane-1,2,3-tricarboxylate, tri(2-propynyl) 1-(benzenesulfonyloxy)propane-1,2,3-tricarboxylate, trimethyl 1-(4-methylbenzenesulfonyloxy)propane-1,2,3-tricarboxylate, tri(2-propynyl) 1-(4-methylbenzenesulfonyloxy)propane-1,2,3-tricarboxylate, tri(2,2,2-trifluoroethyl) 1-(methanesulfonyloxy)propane-1,2,3-tricarboxylate, tri(2-methoxyethyl) 1-(methanesulfonyloxy)propane-1,2,3-tricarboxylate, tri(cyanomethyl) 1-(methanesulfonyloxy)propane-1,2,3-tricarboxylate, tri(2-cyanoethyl) 1-(methanesulfonyloxy)propane-1,2,3-tricarboxylate, trimethyl 1-(trimethylsilyloxy)propane-1,2,3-tricarboxylate, tri(2-propynyl) 1-(trimethylsilyloxy)propane-1,2,3-tricarboxylate, trimethyl 1-(dimethylphosphoryloxy)propane-1,2,3-tricarboxylate, tri(2-propynyl) 1-(dimethylphosphoryloxy)propane-1,2,3-tricarboxylate, trimethyl 1-[(methoxy)methylphosphoryloxy]propane-1,2,3-tricarboxylate, tri(2-propynyl) 1-[(methoxy)methylphosphoryloxy]propane-1,2,3-tricarboxylate, trimethyl 1-(dimethoxyphosphoryloxy)propane-1,2,3-tricarboxylate, tri(2-propynyl) 1-(dimethoxyphosphoryloxy)propane-1,2,3-tricarboxylate, trimethyl 1-(diethoxyphosphoryloxy)propane-1,2,3-tricarboxylate, tri(2-propynyl) 1-(diethoxyphosphoryloxy)propane-1,2,3-tricarboxylate.

Of the above-mentioned compounds, more preferred from the viewpoint of improving low-temperature load characteristics after high-temperature charging storage are succinates such as dimethyl 2-(formyloxy)succinate, diethyl 2-(formyloxy)succinate, divinyl 2-(formyloxy)succinate, di(2-propenyl) 2-(formyloxy)succinate, di(2-propynyl) 2-(formyloxy)succinate, dimethyl 2-(methanesulfonyloxy)succinate, diethyl 2-(methanesulfonyloxy)succinate, divinyl 2-(methanesulfonyloxy)succinate, di(2-propenyl) 2-(methanesulfonyloxy)succinate, di(2-propynyl) 2-(methanesulfonyloxy)succinate, dimethyl 2-(ethanesulfonyloxy)succinate, diethyl 2-(ethanesulfonyloxy)succinate, divinyl 2-(ethanesulfonyloxy)succinate, di(2-propenyl) 2-(ethanesulfonyloxy)succinate, di(2-propynyl) 2-(ethanesulfonyloxy)succinate, dimethyl 2-(benzenesulfonyloxy)succinate, di(2-propynyl) 2-(benzenesulfonyloxy)succinate, dimethyl 2-(4-methylbenzenesulfonyloxy)succinate, di(2-propynyl) 2-(4-methylbenzenesulfonyloxy)succinate, dimethyl 2-(dimethylphosphoryloxy)succinate, diethyl 2-(dimethylphosphoryloxy)succinate, divinyl 2-(dimethylphosphoryloxy)succinate, di(2-propenyl) 2-(dimethylphosphoryloxy)succinate, di(2-propynyl) 2-(dimethylphosphoryloxy)succinate, dimethyl 2-(diethylphosphoryloxy)succinate, diethyl 2-(diethylphosphoryloxy)succinate, divinyl 2-(diethylphosphoryloxy)succinate, di(2-propenyl) 2-(diethylphosphoryloxy)succinate, di(2-propynyl) 2-(diethylphosphoryloxy)succinate, dimethyl 2-[(methoxy)methylphosphoryloxy]succinate, diethyl 2-[(methoxy)methylphosphoryloxy]succinate, divinyl 2-[(methoxy)methylphosphoryloxy]succinate, di(2-propenyl) 2-[(methoxy)methylphosphoryloxy]succinate, di(2-propynyl) 2-[(methoxy)methylphosphoryloxy]succinate, dimethyl 2-[(ethoxy)ethylphosphoryloxy]succinate, diethyl 2-[(ethoxy)ethylphosphoryloxy]succinate, divinyl 2-[(ethoxy)ethylphosphoryloxy]succinate, di(2-propenyl) 2-[(ethoxy)ethylphosphoryloxy]succinate, di(2-propynyl) 2-[(ethoxy)ethylphosphoryloxy]succinate, dimethyl 2-(dimethoxyphosphoryloxy)succinate, diethyl 2-(dimethoxyphosphoryloxy)succinate, divinyl 2-(dimethoxyphosphoryloxy)succinate, di(2-propenyl) 2-(dimethoxyphosphoryloxy)succinate, di(2-propynyl) 2-(dimethoxyphosphoryloxy)succinate, dimethyl 2-(diethoxyphosphoryloxy)succinate, diethyl 2-(diethoxyphosphoryloxy)succinate, divinyl 2-(diethoxyphosphoryloxy)succinate, di(2-propenyl) 2-(diethoxyphosphoryloxy)succinate, di(2-propynyl) 2-(diethoxyphosphoryloxy)succinate, etc.;

2-methylsuccinates such as dimethyl 2-(formyloxy)-2-methylsuccinate, di(2-propynyl) 2-(formyloxy)-2-methylsuccinate, dimethyl 2-(methanesulfonyloxy)-2-methylsuccinate, di(2-propynyl) 2-(methanesulfonyloxy)-2-methylsuccinate, dimethyl 2-(benzenesulfonyloxy)-2-methylsuccinate, di(2-propynyl) 2-(benzenesulfonyloxy)-2-methylsuccinate, dimethyl 2-(4-methylbenzenesulfonyloxy)-2-methylsuccinate, di(2-propynyl) 2-(4-methylbenzenesulfonyloxy)-2-methylsuccinate, dimethyl 2-(dimethoxyphosphoryloxy)-2-methylsuccinate, di(2-propynyl) 2-(dimethoxyphosphoryloxy)-2-methylsuccinate, dimethyl 2-(diethoxyphosphoryloxy)-2-methylsuccinate, di(2-propynyl) 2-(diethoxyphosphoryloxy)-2-methylsuccinate, etc.;

malonates such as dimethyl 2-(formyloxy)malonate, di(2-propynyl) 2-(formyloxy)malonate, dimethyl 2-(methanesulfonyloxy)malonate, di(2-propynyl) 2-(methanesulfonyloxy)malonate, dimethyl 2-(benzenesulfonyloxy)malonate, di(2-propynyl) 2-(benzenesulfonyloxy)malonate, dimethyl 2-(4-methylbenzenesulfonyloxy)malonate, di(2-propynyl) 2-(4-methylbenzenesulfonyloxy)malonate, dimethyl 2-(dimethoxyphosphoryloxy)malonate, di(2-propynyl) 2-(dimethoxyphosphoryloxy)malonate, dimethyl 2-(diethoxyphosphoryloxy)malonate, di(2-propynyl) 2-(diethoxyphosphoryloxy)malonate, etc.;

glutarates such as dimethyl 2-(formyloxy)glutarate, di(2-propynyl) 2-(formyloxy)glutarate, dimethyl 2-(methanesulfonyloxy)glutarate, di(2-propynyl) 2-(methanesulfonyloxy)glutarate, dimethyl 2-(benzenesulfonyloxy)glutarate, di(2-propynyl) 2-(benzenesulfonyloxy)glutarate, dimethyl 2-(4-methylbenzenesulfonyloxy)glutarate, di(2-propynyl) 2-(4-methylbenzenesulfonyloxy)glutarate, dimethyl 2-(dimethoxyphosphoryloxy)glutarate, di(2-propynyl) 2-(dimethoxyphosphoryloxy)glutarate, dimethyl 2-(diethoxyphosphoryloxy)glutarate, di(2-propynyl) 2-(diethoxyphosphoryloxy)glutarate, etc.;

tricarboxylates such as trimethyl 2-(formyloxy)propane-1,2,3-tricarboxylate, tri(2-propynyl) 2-(formyloxy)propane-1,2,3-tricarboxylate, trimethyl 2-(methanesulfonyloxy)propane-1,2,3-tricarboxylate, tri(2-propynyl) 2-(methanesulfonyloxy)propane-1,2,3-tricarboxylate, trimethyl 2-(benzenesulfonyloxy)propane-1,2,3-tricarboxylate, tri(2-propynyl) 2-(benzenesulfonyloxy)propane-1,2,3-tricarboxylate, trimethyl 2-(4-methylbenzenesulfonyloxy)propane-1,2,3-tricarboxylate, tri(2-propynyl) 2-(4-methylbenzenesulfonyloxy)propane-1,2,3-tricarboxylate, trimethyl 2-(dimethoxyphosphoryloxy)-1,2,3-tricarboxylate, tri(2-propynyl) 2-(dimethoxyphosphoryloxy)propane-1,2,3-tricarboxylate, dimethyl 2-(diethoxyphosphoryloxy)glutarate, tri(2-propynyl) 2-(diethoxyphosphoryloxy)propane-1,2,3-tricarboxylate, trimethyl 1-(formyloxy)propane-1,2,3-tricarboxylate, tri(2-propynyl) 1-(formyloxy)propane-1,2,3-tricarboxylate, trimethyl 1-(methanesulfonyloxy)propane-1,2,3-tricarboxylate, tri(2-propynyl) 1-(methanesulfonyloxy)propane-1,2,3-tricarboxylate, trimethyl 1-(benzenesulfonyloxy)propane-1,2,3-tricarboxylate, tri(2-propynyl) 1-(benzenesulfonyloxy)propane-1,2,3-tricarboxylate, trimethyl 1-(4-methylbenzenesulfonyloxy)propane-1,2,3-tricarboxylate, tri(2-propynyl) 1-(4-methylbenzenesulfonyloxy)propane-1,2,3-tricarboxylate, trimethyl 1-(dimethoxyphosphoryloxy) propane-1,2,3-tricarboxylate, tri(2-propynyl) 1-(dimethoxyphosphoryloxy) propane-1,2,3-tricarboxylate, trimethyl 1-(diethoxyphosphoryloxy)propane-1,2,3-tricarboxylate, tri(2-propynyl) 1-(diethoxyphosphoryloxy)propane-1,2,3-tricarboxylate, etc.

Of the specific compounds represented by the general formula (IV-I), more preferred are one or more selected from dimethyl 2-(methanesulfonyloxy)succinate, diethyl 2-(methanesulfonyloxy)succinate, di(2-propenyl) 2-(methanesulfonyloxy)succinate, di(2-propynyl) 2-(methanesulfonyloxy) succinate, dimethyl 2-(benzenesulfonyloxy)succinate, di(2-propynyl) 2-(benzenesulfonyloxy)succinate, dimethyl 2-(4-methylbenzenesulfonyloxy)succinate, di(2-propynyl) 2-(4-methylbenzenesulfonyloxy)succinate, dimethyl 2-(methanesulfonyloxy)-2-methylsuccinate, di(2-propynyl) 2-(methanesulfonyloxy)-2-methylsuccinate, trimethyl 2-(methanesulfonyloxy)propane-1,2,3-tricarboxylate, tri(2-propynyl) 2-(methanesulfonyloxy)propane-1,2,3-tricarboxylate, trimethyl 1-(methanesulfonyloxy)propane-1,2,3-tricarboxylate, tri(2-propynyl) 1-(methanesulfonyloxy)propane-1,2,3-tricarboxylate, dimethyl 2-(formyloxy)succinate, di(2-propynyl) 2-(formyloxy)succinate, dimethyl 2-(dimethoxyphosphoryloxy)succinate, di(2-propynyl) 2-(dimethoxyphosphoryloxy)succinate, dimethyl 2-(diethoxyphosphoryloxy)succinate, di(2-propynyl) 2-(diethoxyphosphoryloxy)succinate, dimethyl 2-(trimethylsilyloxy)succinate, di(2-propynyl) 2-(trimethylsilyloxy)succinate, dimethyl 2-methoxysuccinate, and di(2-propynyl) 2-methoxysuccinate.

Of those, even more preferred are one or more selected from dimethyl 2-(methanesulfonyloxy)succinate, di(2-propenyl) 2-(methanesulfonyloxy)succinate, di(2-propynyl) 2-(methanesulfonyloxy)succinate, dimethyl 2-(4-methylbenzenesulfonyloxy)succinate, di(2-propynyl) 2-(4-methylbenzenesulfonyloxy)succinate, trimethyl 2-(methanesulfonyloxy)propane-1,2,3-tricarboxylate, tri(2-propynyl) 2-(methanesulfonyloxy)propane-1,2,3-tricarboxylate, trimethyl 1-(methanesulfonyloxy)propane-1,2,3-tricarboxylate, tri(2-propynyl) 1-(methanesulfonyloxy)propane-1,2,3-tricarboxylate, dimethyl 2-(formyloxy)succinate, di(2-propynyl) 2-(formyloxy)succinate, dimethyl 2-(dimethoxyphosphoryloxy)succinate, di(2-propynyl) 2-(dimethoxyphosphoryloxy)succinate, dimethyl 2-(trimethylsilyloxy)succinate, di(2-propynyl) 2-(trimethylsilyloxy)succinate, dimethyl 2-methoxysuccinate, and di(2-propynyl) 2-methoxysuccinate.

The compound represented by the general formula (IV-I) is favorably used for a nonaqueous electrolytic solution or a polymer electrolyte as an additive to lithium batteries.

The content of the carboxylate represented by the general formula (IV-I) to be contained in the nonaqueous electrolytic solution of the present invention is from 0.01 to 10% by mass therein. In case where the content is more than 10% by mass, a surface film may be formed excessively on an electrode to worsen low-temperature load characteristics after high-temperature charging storage; but when the content is less than 0.01% by mass, then the surface film formation would be insufficient, therefore failing in attaining the effect of improving low-temperature load characteristics after high-temperature charging storage. The content is preferably at least 0.05% by mass in the nonaqueous electrolytic solution, more preferably at least 0.5% by mass, even more preferably at least 1% by mass; and its upper limit is preferably at most 10% by mass, more preferably at most 5% by mass, even more preferably at most 2% by mass.

In the nonaqueous electrolytic solution of the present invention, the carboxylate represented by the general formula (IV-I), as added thereto, may improve low-temperature load characteristics after high-temperature charging storage; however, when combined with a nonaqueous solvent, an electrolyte salt and further other additives to be mentioned below, the ester can exhibit a specific effect of synergistically improving low-temperature load characteristics after high-temperature charging storage. Though the reason is not always clear, it may be considered that a mixture surface film having a high ionic conductivity and comprising the constitutive elements of the nonaqueous solvent, electrolyte salt and other additives could be formed.

[Nonaqueous Solvent]

The nonaqueous solvent for use in the nonaqueous electrolytic solution of the present invention includes cyclic carbonates, linear carbonates, linear esters, ethers, amides, phosphates, sulfones, lactones, nitriles, carboxylic acid anhydrides, aromatic compounds, S=O bond-containing compounds, etc.

The cyclic carbonates include ethylene carbonate (EC), propylene carbonate (PC), butylene carbonate (BC), 4-fluoro-1,3-dioxolan-2-one (FEC), trans or cis-4,5-difluoro-1,3-dioxolan-2-one (hereinafter the two are collectively called "DFEC"), vinylene carbonate (VC), vinylethylene carbonate (VEC), etc. Of those, preferred is use of at least one cyclic carbonate having a carbon-carbon double bond or a fluorine, as markedly enhancing the effect of improving electrochemical characteristics in a broad temperature range; and more preferred is use of both a cyclic carbonate having a carbon-carbon double bond and a cyclic carbonate having a fluorine. As the cyclic carbonate having a carbon-carbon double bond, preferred are VC and VEC; and as the cyclic carbonate having a fluorine, preferred are FEC and DFEC.

Use of a cyclic carbonate of ethylene carbonate having a methyl group at the 4-position and/or a cyclic carbonate of ethylene carbonate having a fluorine atom at the 4-position is more preferred as enhancing the effect of improving electrochemical characteristics in a broad temperature range.

The cyclic carbonate of ethylene carbonate having a methyl group at the 4-position is preferably propylene carbonate (PC), 1,2-butylene carbonate or 2,3-butylene carbonate, and more preferably propylene carbonate (PC).

The cyclic carbonate of ethylene carbonate having a fluorine atom at the 4-position is preferably a 4-fluoro-1,3-dioxolan-2-one (FEC), or trans or cis-4,5-difluoro-1,3-dioxolan-2-one, and more preferably 4-fluoro-1,3-dioxolan-2-one (FEC).

Use of both the cyclic carbonate of ethylene carbonate having a methyl group at the 4-position and the cyclic carbonate of ethylene carbonate having a fluorine atom at the 4-position is even more preferred as enhancing the effect of improving electrochemical characteristics in a broad temperature range.

Preferably, the cyclic carbonate of ethylene carbonate having a methyl group at the 4-position and/or the cyclic carbonate of ethylene carbonate having a fluorine atom at the 4-position is in an amount of from 1 to 30% by volume relative to the total volume of the nonaqueous solvent, as further enhancing the effect of improving electrochemical characteristics in a broad temperature range, more preferably in an amount of from 5 to 30% by volume, even more preferably in an amount of from 10 to 30% by volume, still more preferably in an amount of from 15 to 30% by volume.

One kind of those solvents may be used, but using two or more different kinds as combined is preferred as further enhancing the effect of improving electrochemical characteristics in a broad temperature range. Even more preferably, three or more different kinds are combined. Preferred combinations of the cyclic carbonates include EC and PC; EC and VC; PC and VC; FEC and VC; FEC and EC; FEC and PC; FEC and DFEC; DFEC and EC; DFEC and PC; DFEC and VC; DFEC and VEC; EC and PC and VC; EC and FEC and PC; EC and FEC and VC; EC and VC and VEC; FEC and PC and VC; DFEC and EC and VC; DFEC and PC and VC; FEC and EC and PC and VC; DFEC and EC and PC and VC, etc. Of those combinations, more preferred combinations are EC and VC; FEC and PC; DFEC and PC; EC and FEC and PC; EC and FEC and VC; and EC and VC and VEC, etc.

Not specifically defined, the content of the cyclic carbonate is preferably within a range of from 10 to 40% by volume relative to the total volume of the nonaqueous solvent. When the content is less than 10% by volume, then the electric conductivity of the nonaqueous electrolytic solution may lower, and electrochemical characteristics in a broad temperature range may worsen; but when more than 40% by volume, then the effect of improving electrochemical characteristics in a broad temperature range may lower since the viscosity of the nonaqueous electrolytic solution may increase. Consequently, the content preferably falls within the above-mentioned range.

The linear carbonates include asymmetric linear carbonates such as methyl ethyl carbonate (MEC), methyl propyl carbonate (MPC), methyl isopropyl carbonate (MIPC), methyl butyl carbonate, ethyl propyl carbonate, etc.; symmetric linear carbonates such as dimethyl carbonate (DMC), diethyl carbonate (DEC), dipropyl carbonate, dibutyl carbonate, etc.

Of those, the solvent preferably contains a linear carbonate having a methyl group, and more preferably contains at least one of DMC, MEC, MPC and MIPC, even more preferably at least one of DMC and MEC.

Also preferably, the solvent contains an asymmetric linear carbonate as the effect of improving electrochemical characteristics in a broad temperature range may be enhanced more, and more preferably the solvent contains both an asymmetric linear carbonate and a symmetric linear carbonate. Preferably, the proportion of the asymmetric linear carbonate in the linear carbonate is at least 50% by volume. As the asymmetric linear carbonate, preferred is one having a methyl group, and most preferred is MEC.

Although one kind of those solvents may be used, two or more kinds of them are preferably used in combination as more effective for improving electrochemical characteristics in a broad temperature range.

Not specifically defined, the content of the linear carbonate is preferably within a range of from 60 to 90% by volume relative to the total volume of the nonaqueous solvent. When the content is less than 60% by volume, then the viscosity of the nonaqueous electrolytic solution may increase to worsen electrochemical characteristics in a broad temperature range, but when more than 90% by volume, then the electric conductivity of the nonaqueous electrolytic solution may lower also to worsen electrochemical characteristics in a broad temperature range. Accordingly, the above range is preferred.

The linear esters include methyl propionate, ethyl propionate, methyl acetate, ethyl acetate, methyl pivalate, butyl pivalate, hexyl pivalate, octyl pivalate, dimethyl oxalate, ethyl methyl oxalate, diethyl oxalate, etc. The ethers include tetrahydrofuran, 2-methyltetrahydrofuran, 1,3-dioxane, 1,4-dioxane, 1,2-dimethoxyethane, 1,2-diethoxyethane, 1,2-dibutoxyethane, etc.

The amides include dimethylformamide, etc.; the phosphates include trimethyl phosphate, tributyl phosphate, trioctyl phosphate, etc.; the sulfones include sulfolane, etc.; the lactones include γ-butyrolactone, γ-valerolactone, α-angelicalactone, etc.; the nitriles include acetonitrile, propionitrile, succinonitrile, glutaronitrile, adiponitrile, etc.

The carboxylic anhydrides include linear carboxylic anhydrides such as acetic anhydride, propionic anhydride, etc.; cyclic carboxylic anhydrides such as succinic anhydride, maleic anhydride, glutaric anhydride, itaconic anhydride, etc.

The aromatic compounds include aromatic compounds each having a branched alkyl group, such as cyclohexylbenzene, fluorocyclohexylbenzene compounds (including 1-fluoro-2-cyclohexylbenzene, 1-fluoro-3-cyclohexylbenzene, and 1-fluoro-4-cyclohexylbenzene), tert-butylbenzene, tert-amylbenzene, an 1-fluoro-4-tert-butylbenzene, and aromatic compounds such as biphenyl, terphenyls (o-, m-, and p-form), diphenyl ether, fluorobenzene, difluorobenzene (o-, m-, and p-form), 2,4-difluoroanisole, and partially hydrogenated terphenyls (including 1,2-dicyclohexylbenzene, 2-phenylbicyclohexyl, 1,2-diphenylcyclohexane, and o-cyclohexylbiphenyl), etc.

The S=O bond-containing compounds include sultone compounds such as 1,3-propanesultone, 1,4-butanesultone, etc.; cyclic sulfite compounds such as ethylene sulfite, hexahydrobenzo[1,3,2]dioxathiolan-2-oxide (also referred to as 1,2-cyclohexanediol cyclic sulfite), 5-vinyl-hexahydro-1,3,2-benzodioxathiol-2-oxide, etc.; sulfonic acid ester compounds such as 1,2-ethanediol dimethanesulfonate, 1,2-propanediol dimethanesulfonate, 1,3-propanediol dimethanesulfonate, 1,4-butanediol dimethanesulfonate, 2-propynyl methanesulfonate, etc.; and vinyl sulfone compounds such as divinyl sulfone, 1,2-bis(vinylsulfonyl)ethane, bis(2-vinylsulfonylethyl)ether, etc.

In general, the S=O bond-containing compound may lower low-temperature cycle properties; however, when combined with the hydroxy acid derivative compound of the present invention, the compound is favorable as improving electrochemical characteristics in a broad temperature range. Above all, preferred are cyclic structure-having sultone compounds or cyclic sulfite compounds; and more preferred is at least one selected from 1,3-propanesultone, 1,4-butanesultone, ethylene sulfite, 5-vinyl-hexahydro-1,3,2-benzodioxathiol-2-oxide.

When the content of the S=O bond-containing compound is more than 10% by mass, then it may worsen electrochemical characteristics in a broad temperature range; and when less than 0.01% by mass, then it could not sufficiently attain the effect of improving electrochemical characteristics in a broad temperature range. Accordingly, the lower limit of the content of the S=O bond-containing compound is preferably at least 0.01% by mass relative to the mass of the nonaqueous electrolytic solution, more preferably at least 0.1% by mass, even more preferably at least 0.5% by mass. The upper limit of the content is preferably at most 10% by mass, more preferably at most 5% by mass, even more preferably at most 3% by mass.

In general, the above-mentioned nonaqueous solvents are combined and used as a mixture thereof for attaining suitable physical properties. The combination includes, for example, a combination of a cyclic carbonate and a linear carbonate, a combination of a cyclic carbonate, a linear carbonate and a lactone, a combination of a cyclic carbonate, a linear carbonate and an ether, a combination of a cyclic carbonate, a linear carbonate and a linear ester, a combination of a cyclic carbonate, a linear carbonate and a nitrile, a combination of a cyclic carbonate, a linear carbonate and an S=O bond-containing compound, etc.

Of those, preferred is use of a nonaqueous solvent of a combination of at least a cyclic carbonate and a linear carbonate, as enhancing electrochemical characteristics in a broad temperature range. In this, the proportion of the cyclic carbonate and the linear carbonate is not specifically defined, but preferably, the ratio (by volume) of cyclic carbonate/linear carbonate is from 10/90 to 40/60, more preferably from 15/85 to 35/65, even more preferably from 20/80 to 30/70.

[Electrolyte Salt]

As the electrolyte salt for use in the present invention, preferably mentioned are the following lithium salts and onium salts.

(Lithium Salt)

The electrolyte salt for use in the present invention includes lithium salts such as $LiPF_6$, $LiPO_2F_2$, $LiBF_4$, $LiClO_4$, etc.; linear alkyl group-having lithium salts such as $LiN(SO_2CF_3)_2$, $LiN(SO_2C_2F_5)_2$, $LiCF_3SO_3$, $LiC(SO_2CF_3)_3$, $LiPF_4(CF_3)_2$, $LiPF_3(C_2F_5)_3$, $LiPF_3(CF_3)_3$, $LiPF_3$ (iso-$C_3F_7$)$_3$/$LiPF_5$(iso-$C_3F_7$), etc.; cyclic alkylene chain-having lithium salts such as $(CF_2)_2(SO_2)_2NLi$, $(CF_2)_3(SO_2)_2NLi$, etc.; and lithium salts with an oxalate complex as the anion therein, such as lithium bis[oxalate-O,O']borate, lithium difluoro[oxalate-O,O']borate, etc. Of those, especially preferred electrolyte salts are $LiPF_6$, $LiBF_4$, $LiN(SO_2CF_3)_2$ and $LiN(SO_2C_2F_5)_2$; and at least one selected from $LiPF_6$, $LiBF_4$ and $LiN(SO_2CF_3)_2$ is a most preferred electrolyte salt.

(Onium Salt)

Preferred examples of the onium salt are various salts of a combination of an onium cation and an anion mentioned below.

Preferred examples of the onium cation include a tetramethylammonium cation, an ethyltrimethylammonium cation, a diethyldimethylammonium cation, a triethylmethylammonium cation, a tetraethylammonium cation, an N,N-dimethylpyrrolidinium cation, an N-ethyl-N-methylpyrrolidinium cation, an N,N-diethylpyrrolidinium cation, a spiro-(N,N')-bipyrrolidinium cation, an N,N'-dimethylimidazolinium cation, an N-ethyl-N'-methylimidazolinium cation, an N,N'-diethylimidazolinium cation, an N,N'-dimethylimidazolinium cation, an N-ethyl-N'-methylimidazolinium cation, an N,N'-diethylimidazolinium cation, etc.

Preferred examples of the anion include a $PF_6$ anion, a $BF_4$ anion, a $ClO_4$ anion, an $AsF_6$ anion, a $CF_3SO_3$ anion, an $N(CF_3SO_2)_2$ anion, an $N(C_2F_5SO_2)_2$ anion, etc.

One or more of these electrolyte salts may be used here either singly or as combined.

A preferred combination of these electrolyte salts comprises $LiPF_6$ and contains a lithium salt having a nitrogen atom or a boron atom. The lithium salt having a nitrogen atom or a boron atom is preferably at least one selected from $LiBF_4$, $LiN(SO_2CF_3)_2$ and $LiN(SO_2C_2F_5)_2$. Preferred are a combination of $LiPF_6$ and $LiBF_4$, a combination of $LiPF_6$ and $LiN(SO_2CF_3)_2$, a combination of $LiPF_6$ and $LiN(SO_2C_2F_5)_2$, etc. Regarding the ratio (by mol) of $LiPF_6$/[$LiBF_4$ or $LiN(SO_2CF_3)_2$ or $LiN(SO_2C_2F_5)_2$], when the ratio of $LiPF_6$ is lower than 70/30, and when the ratio of $LiPF_6$ is higher than 99/1, electrochemical characteristics in a broad temperature range may worsen. Accordingly, the ratio (by mol) of $LiPF_6$/[$LiBF_4$ or $LiN(SO_2CF_3)_2$ or $LiN(SO_2C_2F_5)_2$] is preferably within a range of from 70/30 to 99/1, more preferably within a range of from 80/20 to 98/2. When the electrolyte salts are used as the combination thereof falling within the above-mentioned range, then the effect of improving electrochemical characteristics in a broad temperature range can be further enhanced.

The electrolyte salts can each be mixed at an arbitrary ratio. However, when a ratio (by mol) of the other electrolyte salts except $LiBF_4$, $LiN(SO_2CF_3)_2$ and $LiN(SO_2C_2F_5)_2$ to all the electrolyte salts in the case where $LiPF_5$ is used in combination with those ingredients is less than 0.01%, the effect of improving electrochemical characteristics in a broad temperature range may be poor; and when the ratio exceeds 45%, electrochemical characteristics in a broad temperature range may worsen. Therefore, the ratio (by mol) is preferably from 0.01 to 45%, more preferably from 0.03 to 20%, still more preferably from 0.05 to 10%, and most preferably from 0.05 to 5%.

The lower limit of the concentration of all these electrolyte salts as dissolved in the solution is generally preferably at least 0.3 M relative to the above-mentioned nonaqueous solvent, more preferably at least 0.5 M, even more preferably at least 0.7 M. The upper limit of the concentration is preferably at most 2.5 M, more preferably at most 2.0 M, even more preferably at most 1.5 M.

As the electrolyte for electric double layer capacitors (condensers), usable are known quaternary ammonium salts such as tetraethylammonium tetrafluoroborate, triethylmethylammonium tetrafluoroborate, tetraethylammonium hexafluorophosphate, etc.

[Production of Nonaqueous Electrolytic Solution]

The nonaqueous electrolytic solution of the present invention can be prepared, for example, by: mixing the nonaqueous solvents; adding the electrolyte salt to the mixture; and adding at least one compound selected from the above-mentioned general formula (I) in an amount of from 0.01 to 10% by mass relative to the mass of the nonaqueous electrolytic solution.

In this case, the nonaqueous solvent to be used, and the compound to be added to the electrolytic solution are preferably previously purified within a range not significantly detracting from the producibility, in which, therefore, the impurity content is preferably as low as possible.

The nonaqueous electrolytic solution of the present invention may be used for the first to fourth electrochemical elements mentioned below, in which not only a liquid one but also a gelled one can be used as the nonaqueous electrolyte. Further, the nonaqueous electrolytic solution of the present invention can also be used for solid polymer electrolytes. Above all, the solution is preferably used for the first electrochemical element using a lithium salt as the electrolyte salt (that is, for lithium batteries) or for the fourth electrochemical element (that is, for lithium ion capacitors), more preferably for lithium batteries, and most preferably for lithium secondary batteries.

[The First Electrochemical Element (Lithium Battery)]

The lithium battery of the present invention collectively means a lithium primary battery and a lithium secondary battery, comprising a positive electrode, a negative electrode and the nonaqueous electrolytic solution of an electrolyte salt dissolved in a nonaqueous solvent, and is characterized in that the nonaqueous electrolytic solution contains the carboxylate represented by the above-mentioned general formula (I) in an amount of from 0.01 to 10% by mass relative to the mass of the nonaqueous electrolytic solution.

In the lithium battery of the present invention, the other constitutive components such as the positive electrode and the negative electrode except for the nonaqueous electrolytic solution can be used with no particular limitation.

For example, as the positive electrode active material for lithium secondary batteries, usable is a complex metal oxide with lithium that contains cobalt, manganese and nickel. One kind of these positive electrode active materials can be used alone, or two or more kinds of them can be used in combination.

The complex metal oxide includes, for example, $LiCoO_2$, $LiMn_2O_4$, $LiNiO_2$, $LiCo_{1-x}Ni_xO_2$ (0.01<x<1), $LiCo_{1/3}Ni_{1/3}Mn_{1/3}O_2$, $LiNi_{1/2}Mn_{3/2}O_4$, $LiCo_{0.98}Mg_{0.02}O_2$, etc. Combinations of $LiCoO_2$ and $LiMn_2O_4$; $LiCoO_2$ and $LiNiO_2$; $LiMn_2O_4$ and $LiNiO_2$ are acceptable herein.

For enhancing the safety of the battery in overcharging or enhancing cycle properties, or for enabling the use thereof at a charging potential of 4.3 V or more, a part of the lithium complex oxide may be substituted with any other element. For example, a part of cobalt, manganese and nickel may be substituted with at least one element of Sn, Mg, Fe, Ti, Al, Zr, Cr, V, Ga, Zn, Cu, Bi, Mo, La, etc.; or O may be partly substituted with S or F; or the oxide may be coated with a compound containing such other element.

Of those, preferred are lithium complex metal oxides such as $LiCoO_2$, $LiMn_2O_4$, and $LiNiO_2$, with which the positive electrode charging potential in a fully-charged state may be used at 4.3 V or more based on Li. More preferred are lithium complex oxides usable at 4.4 V or more, such as $LiCO_{1-x}M_xO_2$ (where M represents at least one element of Sn, Mg, Fe, Ti, Al, Zr, Cr, V, Ga, Zn, and Cu; $0.001 \leq x \leq 0.05$), $LiCo_{1/3}Ni_{1/3}Mn_{1/3}O_2$, and $LiNi_{1/2}Mn_{3/2}O_4$.

When a lithium complex metal oxide capable of being used at a higher charged voltage is used, the effect of improving electrochemical characteristics in a broad temperature range may often worsen owing to the reaction with the electrolytic solution during charging. Of the lithium secondary battery according to the present invention, however, the electrochemical characteristics can be prevented from worsening.

Further, as the positive electrode active material, also usable are lithium-containing olivine-type phosphates. Specific examples thereof include $LiFePO_4$, $LiCoPO_4$, $LiNiPO_4$, $LiMnPO_4$, etc.

The lithium-containing olivine-type phosphates may be partly substituted with any other element. For example, a part of iron, cobalt, nickel, and manganese therein may be substituted with at least one element selected from Co, Mn, Ni, Mg, Al, B, Ti, V, Nb, Cu, Zn, Mo, Ca, Sr, W, and Zr; or the phosphates may be coated with a compound containing any of these other elements or with a carbon material. Among these, preferred are those containing at least iron or manganese, and more preferred are $LiFePO_4$ and $LiMnPO_4$.

Further, the lithium-containing olivine-type phosphate may be combined with, for example, the above-mentioned positive electrode active materials.

In case where an element Ni is contained in the positive electrode, impurities such as LiOH in the positive electrode active material may increase so that the decomposition of the electrolytic solution may be promoted. In such a case, the nonaqueous electrolytic solution of the present invention is preferably used, since the effect thereof of improving electrochemical characteristics in a broad temperature range can be more remarkable. In particular, when the Ni atom concentration in the positive electrode active material is from 5 to 25 atomic %, the advantage of the nonaqueous electrolytic solution of the present invention is more remarkable, and even more preferably, the Ni atom concentration is from 8 to 21 atomic %.

Not specifically defined, the electroconductive agent of the positive electrode may be any electron-conductive material not undergoing chemical change. For example, it includes graphites such as natural graphite (flaky graphite, etc.), artificial graphite, etc.; carbon blacks such as acetylene black, Ketjen black, channel black, furnace black, lamp black, thermal black, etc. Graphites and carbon blacks may be combined suitably. The amount of the electroconductive agent to be added to the positive electrode mixture is preferably from 1 to 10% by mass, more preferably from 2 to 5% by mass.

The positive electrode may be formed by mixing the above-mentioned positive electrode active material with an electroconductive agent such as acetylene black, carbon black or the like, and with a binder such as polytetrafluoroethylene (PTFE), polyvinylidene fluoride (PVDF), styrene/butadiene copolymer (SBR), acrylonitrile/butadiene copolymer (NBR), carboxymethyl cellulose (CMC), ethylene/propylene/diene terpolymer or the like, then adding thereto a high-boiling point solvent such as 1-methyl-2-pyrrolidone or the like, and kneading them to give a positive electrode mixture, thereafter applying the positive electrode mixture onto an aluminium foil or a stainless lath plate or the like serving as a collector, and drying and shaping it under pressure, and then heat-treating it in vacuum at a temperature of from 50° C. to 250° C. or so for about 2 hours.

The density of the part except the collector of the positive electrode may be generally at least 1.5 g/cm$^3$, and for further increasing the capacity of the battery, the density is preferably at least 2 g/cm$^3$, more preferably at least 3 g/cm$^3$, even more preferably at least 3.6 g/cm$^3$. The upper limit is preferably at most 4 g/cm$^3$.

For the positive electrode for lithium primary batteries, there are mentioned oxides or chalcogen compounds of one or more metal elements such as $CuO$, $Cu_2O$, $Ag_2O$, $Ag_2CrO_4$, $CuS$, $CuSO_4$, $TiO_2$, $TiS_2$, $SiO_2$, $SnO$, $V_2O_5$, $V_6O_{12}$, $VO_N$, $Nb_2O_5$, $Bi_2O_3$, $Bi_2Pb_2O_5$, $Sb_2O_3$, $CrO_3$, $Cr_2O_3$, $MoO_3$, $WO_3$, $SeO_2$, $MnO_2$, $Mn_2O_3$, $Fe_2O_3$, $FeO$, $Fe_3O_4$, $Ni_2O_3$, $NiO$, $CoO_3$, $CoO$, etc.; sulfur compounds such as $SO_2$, $SOCl_2$, etc.; carbon fluorides (fluorographite) represented by a general formula $(CF_x)_n$, etc. Of those, preferred are $MnO_2$, $V_2O_5$, fluorographite, etc.

As the negative electrode active material for lithium secondary batteries, usable are one or more of lithium metal, lithium alloys, carbon materials (graphites such as artificial graphite, natural graphite, etc.) capable of absorbing and releasing lithium, tin, tin compounds, silicon, silicon compounds and the like, either singly or as combined.

Of those, preferred is use of high-crystalline carbon materials such as artificial graphite, natural graphite and the like, in view of the ability thereof to absorb and release lithium ions, and more preferred is use of a carbon material having a graphite-type crystal structure where the lattice (002) spacing ($d_{002}$) is at most 0.340 nm (nanometers), especially from 0.335 to 0.337 nm.

When artificial graphite particles having a bulky structure where plural flattened graphite fine particles aggregate or bond together non-parallel to each other, or graphite particles produced through treatment of spheronization comprising repeatedly imparting mechanical action such as compression force, friction force, shear force or the like to, for example, flaky natural graphite particles are used, and when the ratio of the peak intensity I (110) of the (110) plane of the graphite crystal obtained in X-ray diffractiometry of a negative electrode sheet as formed by pressing so that the density of the part except the collector of the negative electrode could be 1.5 g/cm$^3$, to the peak intensity I (004) of the (004) plane thereof, I(110)/I(004) is at least 0.01, then the Li ion absorption and release sites would be clogged through decomposition of the electrolytic solution in high-temperature cycles so that electrochemical characteristics in a broad temperature range would worsen; however, when the electrolytic solution of the present invention is used, the above-mentioned effect can be remarkably enhanced, and therefore use of the electrolytic solution of the present invention is favorable in this point. More preferably, the ratio is at least 0.05, even more preferably at least 0.1. On the other hand, when too much processed, the crystallinity may worsen and the discharge capacity of batteries may lower; and therefore, the upper limit is at most 0.5, more preferably at most 0.3.

When a high-crystalline carbon material is used, it may readily react with a nonaqueous electrolytic solution in charging to thereby worsen electrochemical characteristics in a broad temperature range; however, in the lithium secondary battery of the present invention, the reaction of the material with the nonaqueous electrolytic solution can be prevented. In addition, when the high-crystalline carbon material is coated with a low-crystalline carbon material, it is favorable as bettering electrochemical characteristics in a broad temperature range.

The metal compound capable of absorbing and releasing lithium, serving as a negative electrode active material, includes compounds containing at least one metal element of Si, Ge, Sn, Pb, P, Sb, Bi, Al, Ga, In, Ti, Mn, Fe, Co, Ni, Cu, Zn, Ag, Mg, Sr, Ba, etc. These metal compounds may have any morphology of simple substances, alloys, oxides, nitrides, sulfides, borides, alloys with lithium or the like; but preferred are any of simple substances, alloys, oxides and alloys with lithium, as capable of increasing the capacity of batteries. Above all, more preferred are those containing at least one element selected from Si, Ge and Sn, and even more preferred are those containing at least one element selected from Si and Sn, as capable of increasing the capacity of batteries.

The negative electrode may be formed, using the same electroconductive agent, binder and high-boiling point solvent as in the formation of the above-mentioned positive electrode. These are mixed and kneaded to give a negative electrode mixture, then the negative electrode mixture is applied onto a copper foil or the like serving as a collector, then dried and shaped under pressure, and thereafter heat-treated in vacuum at a temperature of from 50° C. to 250° C. or so for about 2 hours.

In case where graphite is used as the negative electrode active material, the density of the part except the collector of the negative electrode may be generally at least 1.4 g/cm$^3$, and for further increasing the capacity of batteries, the density is preferably at least 1.6 g/cm$^3$, more preferably at least 1.7 g/cm$^3$. The upper limit is preferably at most 2 g/cm$^3$.

As the negative electrode active material for lithium primary batteries, usable are lithium metal or lithium alloys.

The structure of the lithium battery is not specifically defined. The battery may be a coin-shaped battery, a cylindrical battery, a square-shaped battery, or a laminate-type battery, each having a single-layered or multi-layered separator.

For the separator for the battery, usable is a single-layer or laminate porous film of polyolefin such as polypropylene, polyethylene or the like, as well as a woven fabric, a nonwoven fabric, etc.

The lithium secondary battery of the present invention has excellent cycle properties for a long period of time even when the final charging voltage is 4.2 V or more, especially 4.3 v or more, and further, the characteristics of the battery are still good even at 4.4 V or more. The discharging final voltage could be 2.5 V or more, further 2.8 V or more. The current value is not specifically defined. In general, the battery is used at a constant current discharge of from 0.1 to 3 C. The lithium secondary battery of the present invention can be charged/discharged at −40 to 100° C., preferably at 0 to 80° C.

In the present invention, as a countermeasure against the increase in the internal pressure of the lithium secondary battery, there may be employed a method of providing a safety valve in the battery cap or a method of forming a cutout in the battery component such as the battery can, the gasket or the like. In addition, as a safety countermeasure against overcharging, a current breaker capable of detecting the internal pressure of the battery to cut off the current may be provided in the battery cap.

[The Second Electrochemical Element (Electric Double-Layer Capacitor)]

This is an electrochemical element that stores energy by utilizing the electric double layer capacitance in the interface between the electrolytic solution and the electrode therein.

One example of the present invention is an electric double layer capacitor. The most typical electrode active material to be used in the electrochemical element is active carbon. The double layer capacitance increases almost in proportion to the surface area.

[The Third Electrochemical Element]

This is an electrochemical element that stores energy by utilizing the doping/dedoping reaction of the electrode therein. As the electrode active material for use in the electrochemical element, there may be mentioned metal oxides such as ruthenium oxide, iridium oxide, tungsten oxide, molybdenum oxide, copper oxide, etc.; n-conjugated polymers such as polyacene, polythiophene derivatives, etc. The capacitor that uses the electrode active material of the type enables energy storage along with the doping/dedoping reaction at the electrode therein.

[The Fourth Electrochemical Element (Lithium Ion Capacitor)]

This is an electrochemical element that stores energy by utilizing the lithium ion intercalation into the carbon material such as graphite or the like of the negative electrode therein. This may be referred to as a lithium ion capacitor (LIC). As the positive electrode, for example, there may be mentioned one that utilizes the electric double layer between the active carbon electrode and the electrolytic solution therein, or one that utilizes the doping/dedoping reaction of the n-conjugated polymer electrode therein. The electrolytic solution contains at least a lithium salt such as $LiPF_6$ or the like.

[The Second Compound]

The novel second compound of the present invention, hydroxy acid derivative compound is represented by the following general formula (II-III):

[Chemical Formula 20]

(II-III)

(In the formula, $X^{22}$ represents $-CR^{27}R^{28}-(CH_2)_n-$, or represents the following general formula (II-IV).)

[Chemical Formula 21]

(II-IV)

(In the formula, $R^{25}$ represents an alkylsilyl group having from 3 to 12 carbon atoms, an alkyl group having from 1 to 6 carbon atoms, an alkenyl group having from 2 to 6 carbon atoms, an alkynyl group having from 3 to 6 carbon atoms, an alkanesulfonyl group having from 1 to 6 carbon atoms, an acyl group having from 2 to 6 carbon atoms, an alkoxycarbonyl group having from 2 to 6 carbon atoms, an alkenyloxycarbonyl group having from 3 to 7 carbon atoms, an alkynyloxycarbonyl group having from 4 to 7 carbon atoms, a formyl group, a dialkylphosphoryl group having from 2 to 16 carbon atoms, an alkyl(alkoxy)phosphoryl group having from 2 to 16 carbon atoms, or a dialkoxyphosphoryl group having from 2 to 16 carbon atoms; when $R^{25}$ is an alkylsilyl group, then $R^{26}$ is an alkenyl group having from 2 to 6 carbon atoms, or an alkynyl group having from 3 to 6 carbon atoms; when $R^{25}$ is an alkenyl group having from 2 to 6 carbon atoms, an alkynyl group having from 3 to 6 carbon atoms, an alkanesulfonyl group having from 1 to 6 carbon atoms, an alkoxycarbonyl group having from 2 to 6 carbon atoms, an alkenyloxycarbonyl group having from 3 to 7 carbon atoms, an alkynyloxycarbonyl group having from 4 to 7 carbon atoms, a formyl group, a dialkylphosphoryl group having from 2 to 16 carbon atoms, an alkyl(alkoxy)phosphoryl group having from 2 to 16 carbon atoms, or a dialkoxyphosphoryl group having from 2 to 16 carbon atoms, then $R^{26}$ is an alkylsilyl group having from 3 to 12 carbon atoms; $R^{27}$ and $R^{28}$ each represent a hydrogen atom or an alkyl group having from 1 to 6 carbon atoms; n indicates an integer of from 0 to 3; at least one hydrogen atom on the carbon atoms of $R^{26}$ may be substituted with a halogen atom, an alkoxy group having from 1 to 4 carbon atoms, or a nitrile group; provided that when $R^{25}$ is an alkenyl group, then n=0, and when $R^{26}$ is an alkenyl group, then $R^{25}$ is a trimethylsilyl group.)

In the general formula (II-III), the linear or branched alkenyl group having from 2 to 6 carbon atoms or the linear or branched alkynyl group having from 3 to 6 carbon atoms for the substituent $R^{26}$ is described in the above-mentioned general formula (II-I), and in this section, therefore, the description is omitted for evading duplicate information. In this case, the substituent $R^{22}$ in the general formula (II-I) is read as the substituent $R^{26}$ in the general formula (II-III).

Similarly, the substituents $R^{21}$, $R^{23}$ and $R^{24}$ in the above-mentioned general formula (II-I) each are read as the substituents $R^{25}$, $R^{27}$ and $R^{28}$ in the general formula (II-III).

(Trialkylsilyloxycarboxylate Compound)

The production method for the trialkylsilyloxycarboxylate compound is not specifically defined. For example, the compound can be produced by reacting a hydroxycarboxylate and a trialkylsilyl halide for etherification in the presence or absence of a solvent and in the presence of a base.

The starting compound, hydroxycarboxylate can be produced according to existing known methods. For example, employable here is the method described in Advanced Organic Chemistry, 4th Ed., Jerry March, John Wiley & Sons, pp. 393-400.

The amount of the trialkylsilyl halide to be used in the above-mentioned method is preferably from 0.9 to 10 mols relative to 1 mol of the hydroxycarboxylate, more preferably from 1 to 3 mols, even more preferably from 1 to 1.5 mols.

The usable trialkylsilyl halide includes trimethylsilyl chloride, triethylsilyl chloride, tert-butyldimethylsilyl chloride, trimethylsilyl bromide, triethylsilyl bromide, etc. Of those, industrially preferred are inexpensive trialkylsilyl chlorides such as trimethylsilyl chloride, triethylsilyl chloride, etc.

Not specifically defined, the solvent may be any one inert to the reaction. The usable solvent includes aliphatic hydrocarbons, halogenohydrocarbons, aromatic hydrocarbons, halogenoaromatic hydrocarbons, ethers, nitriles, sulfoxides, nitro compounds, etc., as well as amides such as N,N-dimethylformamide, etc.; esters such as ethyl acetate, dimethyl carbonate, etc.; and their mixtures. Of those, especially preferred are aromatic hydrocarbons such as toluene, xylene, etc.

The amount of the solvent to be used is preferably from 0 to 30 parts by mass relative to 1 part by mass of the hydroxycarboxylate, more preferably from 1 to 15 parts by mass.

As the base, usable is any of inorganic bases and organic bases. The usable base includes inorganic bases and organic bases.

The amount of the base to be used is preferably from 0.8 to 5 mols relative to 1 mol of the hydroxycarboxylate, from the viewpoint of preventing side products, more preferably from 1 to 3 mols, even more preferably from 1 to 1.5 mols.

In the above-mentioned reaction, the lower limit of the reaction temperature is preferably −20° C. or higher, and more preferably −10° C. or higher so as not to lower the reactivity. From the viewpoint of preventing side reaction and decomposition of product, the upper limit of the reaction temperature is preferably 80° C. or lower, more preferably 60° C. or lower.

The reaction time may be suitably changed depending on the reaction temperature and scale; however, when the reaction time is too short, then unreacted matters may remain; but on the contrary, when the reaction time is too long, the product may decompose or side reaction may occur. Accordingly, the time is preferably from 0.1 to 12 hours, more preferably from 0.2 to 6 hours.

[The Third Compound]

The novel third compound, carboxylate of the present invention is represented by the following general formula (III-II):

[Chemical Formula 22]

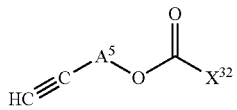

(III-II)

(In the formula, $X^{32}$ represents $-A^6-C\equiv N$ or $A^7-C(=O)O-A^8-C\equiv N$; $A^5$, $A^7$ and $A^8$ each independently represent an alkylene group having from 1 to 6 carbon atoms; $A^6$ represents an alkylene group having from 2 to 6 carbon atoms.)

In the general formula (III-II), concretely, the linear or branched alkylene group having from 1 to 6 carbon atoms represented by $A^5$, $A^7$ and $A^8$ preferably includes a methylene group, an ethylene group, a trimethylene group, a tetramethylene group, a pentamethylene group, a hexamethylene group, an ethane-1,1-diyl group, a propane-2,2-diyl group, a propane-1,2-diyl group, a butane-1,3-diyl group, a pentane-1,4-diyl group, a hexane-1,5-diyl group, a 2-methylpropane-1,3-diyl group, a 2,2-dimethylpropane-1,3-diyl group, etc. Concretely, the linear or branched alkylene group having from 2 to 6 carbon atoms represented by $A^6$ preferably includes an ethylene group, a trimethylene group, a tetramethylene group, a pentamethylene group, a hexamethylene group, a propane-1,2-diyl group, a butane-1,3-diyl group, a pentane-1,4-diyl group, a hexane-1,5-diyl group, a 2-methylpropane-1,3-diyl group, a 2,2-dimethylpropane-1,3-diyl group, etc. However, the bonding position (that is, the bonding order) of the above-mentioned groups in the general formula (III-II) is not specifically defined.

Of those, the linear alkylene group of $A^6$ and $A^7$ is more preferably an alkylene group having from 2 to 6 carbon atoms such as an ethylene group, a trimethylene group, a tetramethylene group, a pentamethylene group or a hexamethylene group, even more preferably an ethylene group, a trimethylene group or a tetramethylene group from the viewpoint of improving low-temperature cycle properties. The branched alkylene group is more preferably an alkylene group having from 3 to 5 carbon atoms, such as a propane-1,2-diyl group, a butane-1,3-diyl group, a pentane-1,4-diyl group, a 2-methylpropane-1,2-diyl group or a 2,2-dimethylpropane-1,3-diyl group, and even more preferably a propane-1,2-diyl group or a butane-1,3-diyl group.

The compound represented by the general formula (III-II) includes the compound represented by the following general formula (III-IV):

[Chemical Formula 23]

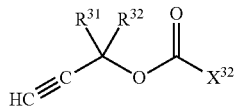

(III-IV)

In the general formula (III-IV), $R^{31}$ and $R^{32}$ each independently represent an alkyl group having from 1 to 4 carbon atoms, or a hydrogen atom; $X^{32}$ represents $-R^4-C\equiv N$, $R^4$ represents a linear or branched alkylene group having from 2 to 6 carbon atoms. Specific examples and preferred examples of the groups in the general formula (III-IV) are the same as those described in the general formula (III-III). In this, specific examples and preferred examples of the substituents in the compound represented by the general formula (III-IV) are the same as those in the description relating to the general formula (III-III) in which $X''$ is replaced by $X^2$.

The production method for the carboxylate compound represented by the general formula (III-IV) is not specifically defined. For example, the compound can be produced by reacting a methyl cyanocarboxylate and an alcohol for interesterification in the presence or absence of a solvent and in the presence of a catalyst.

The starting compound, methyl cyanocarboxylate can be produced according to existing known methods. For example, herein employable is the method described in Precision Organic Synthesis [Experiment Manual] Nanko-do, p. 133.

The amount of the alcohol to be used in the above-mentioned method is preferably from 0.8 to 10 mols relative to 1 mol of the methyl cyanocarboxylate, more preferably from 0.9 to 5 mols, even more preferably from 1 to 3 mols.

The usable alcohol includes propargyl alcohol, 1-methylpropargyl alcohol, 1,1-dimethylpropargyl alcohol, etc.

Not specifically defined, the solvent may be any one inert to the reaction. The usable solvent includes aliphatic hydrocarbons, halogenohydrocarbons, aromatic hydrocarbons, halogenoaromatic hydrocarbons, ethers, nitriles, sulfoxides, nitro compounds, etc., as well as amides such as N,N-dimethylformamide, etc., and their mixtures. Of those, especially preferred are aromatic hydrocarbons such as toluene, xylene, etc.

The amount of the solvent to be used is preferably from 0 to 30 parts by mass relative to 1 part by mass of the methyl cyanocarboxylate, more preferably from 1 to 15 parts by mass.

The acid catalyst includes mineral acids such as sulfuric acid, hydrochloric acid, etc.; arylsulfonic acids such as benzenesulfonic acid, paratoluenesulfonic acid, etc.; Lewis acids such as titanium tetraisopropoxide, etc. Of those, especially preferred is titanium tetraisopropoxide.

The amount of the acid catalyst to be used is preferably from 0.001 to 1 mol relative to 1 mol of the methyl cyanocarboxylate from the viewpoint of preventing side products, more preferably from 0.005 to 0.5 mols, even more preferably from 0.01 to 0.1 mols.

In the above-mentioned reaction, the lower limit of the reaction temperature is preferably 50° C. or higher, and more preferably 80° C. or higher so as not to lower the reactivity. From the viewpoint of preventing side reaction and decomposition of product, the upper limit of the reaction temperature is preferably 180° C. or lower, more preferably 150° C. or lower.

The reaction time may be suitably changed depending on the reaction temperature and scale; however, when the reaction time is too short, then unreacted matters may remain; but on the contrary, when the reaction time is too long, the product may decompose or side reaction may occur. Accordingly, the time is preferably from 0.1 to 24 hours, more preferably from 1 to 12 hours.

The carboxylate compound represented by the general formula (III-II) can also be produced according to the method mentioned below.

Regarding the production method for the carboxylate, for example, employable is the method described in Journal of Organic Chemistry, Vol. 72, No. 6, pp. 1962-1979, 2007, in which a carboxylic acid compound is reacted with an alcohol compound in a solvent in the presence of a dehydrating condensing agent. The starting compound, carboxylic acid compound can be produced according to existing known methods, for which, for example, employable is the method described in Journal of Medicinal Chemistry, Vol. 35, No. 18, pp. 3364-3369, 1992.

[The Fourth Compound]

The novel fourth compound, carboxylate of the present invention is represented by the following general formula (IV-II):

[Chemical Formula 24]

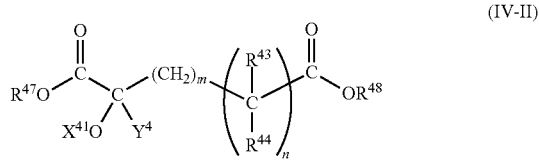

(IV-II)

(In the formula, $R^{47}$ and $R^{48}$ each independently represent an alkynyl group having from 3 to 8 carbon atoms; $R^{43}$, $R^{44}$, $X^{41}$, $Y^4$, m and n have the same meanings as above.)

Specific examples and preferred examples of the groups in the general formula (IV-II) are the same as those in the general formula (IV-I) described hereinabove. However, the specific examples and the preferred examples of the substituents and the compound represented by the general formula (IV-II) are the same as those in the general formula (IV-I) in which $R^{41}$ is replaced by $R^{47}$ and $R^{42}$ is by $R^{48}$.

The carboxylate compound represented by the general formula (IV-II) can be produced according to the method mentioned below; however, the present invention is not limited to the production method. The starting compound, hydroxycarboxylate can be produced according to existing known methods. For example, applicable thereto is the method described in Macromolecules, Vol. 36, No. 18, pp. 6939-6941, 2003.

(a) As the method for producing an alkyloxycarboxylate compound, there may be mentioned a method of reacting a hydroxycarboxylate with an alkyl halide or an alkyl sulfonate in a solvent or without a solvent in the presence of a base.

(b) As the method for producing a formyloxycarboxylate compound, there may be mentioned a method of reacting a hydroxycarboxylate with formic acid in a solvent or without solvent in the presence of a condensing agent.

(c) As the method for producing an acyloxycarboxylate compound, there may be mentioned a method of reacting a hydroxycarboxylate with an alkylcarboxylic acid halide or an alkylcarboxylic acid anhydride for esterification in a solvent or without a solvent in the presence of a base.

(d) As the method for producing an alkoxycarbonyloxycarboxylate compound, there may be mentioned a method of reacting a hydroxycarboxylate with an alkyl haloformate in a solvent or without a solvent in the presence of a base.

(e) As the method for producing an alkanesulfonyloxycarboxylate compound, there may be mentioned a method of reacting a hydroxycarboxylate with an alkanesulfonyl halide or an alkanesulfonic acid anhydride in a solvent or without a solvent in the presence of a base.

(f) As the method for producing an alkylsilyloxycarboxylate compound, there may be mentioned a method of reacting a hydroxycarboxylate with an alkylsilyl halide in a solvent or without a solvent in the presence of a base.

(g) As the method for producing a dialkylphosphoryloxycarboxylate compound, there may be mentioned a method of reacting a hydroxycarboxylate with a dialkylphosphoryl halide in a solvent or without a solvent in the presence of a base.

(h) As the method for producing an alkoxy(alkyl)phosphoryloxycarboxylate compound, there may be mentioned a method of reacting a hydroxycarboxylate with an alkoxy(alkyl)phosphoryl halide in a solvent or without a solvent in the presence of a base.

(i) As the method for producing a dialkoxyphosphoryloxycarboxylate compound, there may be mentioned a method of reacting a hydroxycarboxylate with a dialkoxyphosphoryl halide in a solvent or without a solvent in the presence of a base.

In the above (e) for producing an alkanesulfonyloxycarboxylate compound, the amount to be used of the alkanesulfonyl halide or the alkanesulfonic acid anhydride to be reacted with the hydroxycarboxylate is preferably from 0.9 to 10 mols per mol of the hydroxycarboxylate, more preferably from 1 to 3 mols, most preferably from 1 to 1.5 mols.

The alkanesulfonyl halide to be used includes methanesulfonyl chloride, ethanesulfonyl chloride, trifluoromethanesulfonyl chloride, methanesulfonyl bromide, ethanesulfonyl bromide, trifluoromethanesulfonyl bromide, etc.; the alkanesulfonic acid anhydride includes methanesulfonic acid anhydride, ethanesulfonic acid anhydride, trifluoromethanesulfonic acid anhydride, etc. Preferred for industrial use are inexpensive methanesulfonyl chloride, ethanesulfonyl chloride and trifluoromethanesulfonic acid anhydride.

Not specifically defined, the solvent to be used for the synthesis may be any one inert to the reaction, including aliphatic hydrocarbons such as hexane, heptane, etc.; halogenohydrocarbons such as dichloroethane, dichloropropane, etc.; aromatic hydrocarbons such as toluene, xylene, etc.; halogenoaromatic hydrocarbons such as chlorobenzene, fluorobenzene, etc.; ethers such as diethyl ether, etc.; nitriles such as acetonitrile, propionitrile, etc.; amides such as N,N-dimethylformamide, N,N-dimethylacetamide, etc.; sulfoxides such as dimethyl sulfoxide, etc.; nitroalkanes such as nitromethane, nitroethane, etc.; esters such as ethyl acetate, dimethyl carbonate, etc.; and their mixtures. Especially preferred are toluene, xylene, ethyl acetate. The amount of the solvent to be used is preferably from 0 to 30 parts by mass relative to 1 part by mass of the hydroxycarboxylate, more preferably from 1 to 15 parts by mass.

The base to be used for the synthesis may be any of an inorganic base and an organic base. These may be used either singly or as combined. The usable inorganic base includes potassium carbonate, sodium carbonate, calcium hydroxide, and calcium oxide. The usable organic base includes linear or branched aliphatic tertiary amines, unsubstituted or substituted imidazoles, pyridines, pyrimidines. Especially preferred are trialkylamines such as trimethylamine, triethylamine, tripropylamine, tributylamine, ethyldiisopropylamine, etc.; pyridines such as pyridine, N,N-dimethylaminopyridine, etc. The amount of the base to be used is preferably from 0.8 to 5 mols relative to 1 mol of the hydroxycarboxylate, more preferably from 1 to 3 mols, and even more preferably from 1 to 1.5 mols as preventing the formation of side products.

In the reaction of the alkanesulfonyl halide or the alkanesulfonic acid anhydride with the hydroxycarboxylate, the lower limit of the reaction temperature is preferably −20° C. or higher, and more preferably −10° C. or higher so as not to lower the reactivity. The upper limit of the reaction temperature is preferably 80° C. or lower, and more preferably 60° C. or lower since side reaction and decomposition of the product may be easily prevented. The reaction time depends on the reaction temperature and the scale. In case where the reaction time is too short, unreacted matters may remain; but on the contrary, when the reaction time is too long, the product may decompose and side reaction may occur. Preferably, the time is from 0.1 to 12 hours, more preferably from 0.2 to 6 hours.

EXAMPLES

Synthesis Examples of novel compounds of the present invention, and Examples of electrolytic solution using the compound and others are shown below. However, the present invention is not limited to these Examples.

Examples I-1 to I-15, Comparative Examples I-1 to I-2

(1) Production of Lithium Ion Secondary Battery

94% by mass of $LiCoO_2$ (positive electrode active material) and 3% by mass of acetylene black (electroconductive agent) were mixed, and added to and mixed in a solution previously prepared by dissolving 3% by mass of polyvinylidene fluoride (binder) in 1-methyl-2-pyrrolidone, thereby preparing a positive electrode mixture paste. The positive electrode mixture paste was applied on one surface of an aluminium foil (collector), then dried, processed under pressure and blanked into a predetermined size, thereby producing a positive electrode sheet. The density of the part of the positive electrode except the collector was 3.6 g/cm$^3$. On the other hand, 95% by mass of artificial graphite ($d_{002}$=0.335 nm, negative electrode active material) coated with low-crystalline carbon was added to and mixed in a solution previously prepared by dissolving 5% by mass of polyvinylidene fluoride (binder) in 1-methyl-2-pyrrolidone, thereby preparing a negative electrode mixture paste. The negative electrode mixture paste was applied onto one surface of a copper foil (collector), dried, processed under pressure and blanked into a predetermined size, thereby producing a negative electrode sheet. The density of the part of the negative electrode except the collector was 1.7 g/cm$^3$. The positive electrode sheet, a porous polyethylene film separator and the negative electrode sheet were laminated in that order, and a nonaqueous electrolytic solution having the composition shown in Table 1 was added thereto to construct a 2032-type coin battery.

(2) Evaluation of Low-Temperature Cycle Properties

In a thermostatic chamber kept at 25° C., the battery fabricated according to the above-mentioned method was charged up to 4.2 V (charging final voltage) with a constant current of 1 C, then charged for 2.5 hours under a constant voltage of 4.2 V, and thereafter discharged under a constant current of 1 C to a discharge voltage of 3.0 V (discharging final voltage). Next, in a thermostatic chamber at 0° C., this was charged up to 4.2 V with a constant current of 1 C, then charged for 2.5 hours under a constant voltage of 4.2 V, and thereafter discharged under a constant current of 1 C to a discharge voltage of 3.0 V. The cycle was repeated up to 50 cycles. According to the formula mentioned below, the discharge capacity retention rate (%) after 50 cycles at 0° C. was calculated. The results are shown in Table 1.

0° C. Discharge Capacity Retention Rate after 50 cycles(%)=[(discharge capacity at 0° C. at 50th cycle/discharge capacity at 0° C. at 1st cycle)× 100.

(3) Evaluation of High-Temperature Cycle Properties

In a thermostatic chamber kept at 60° C., the battery fabricated according to the above-mentioned method was charged up to 4.2 V (charging final voltage) with a constant current of 1 C, then charged for 2.5 hours under a constant voltage of 4.2 V, and thereafter discharged under a constant current of 1 C to a discharge voltage of 3.0 V (discharging final voltage). The cycle was repeated up to 100 cycles. According to the formula mentioned below, the discharge capacity retention rate (%) after 100 cycles at 60° C. was calculated. The results are shown in Table 1.

60° C. Discharge Capacity Retention Rate after 100 cycles (%)=[(discharge capacity at 60° C. at 100th cycle/discharge capacity at 60° C. at 1st cycle)×100.

The condition in producing the batteries and the battery characteristics are shown in Table 1.

TABLE 1

| | Composition of Electrolyte Salt Composition of Nonaqueous Electrolytic Solution (ratio by volume of solvents) | Compound | Amount Added (content in nonaqueous electrolytic solution) (wt %) | 0° C. Discharge Capacity Retention Rate after 50 cycles (%) | 60° C. Discharge Capacity Retention Rate after 100 cycles (%) |
|---|---|---|---|---|---|
| Example I-1 | 1M LiPF$_6$ EC/FEC/MEC(28/2/70) | 2-propynyl (R)-2-(methanesulfonyloxy)propionate | 0.1 | 73 | 75 |
| Example I-2 | 1M LiPF$_6$ EC/FEC/MEC(28/2/70) | 2-propynyl (R)-2-(methanesulfonyloxy)propionate | 1 | 80 | 86 |
| Example I-3 | 1M LiPF$_6$ EC/FEC/MEC(28/2/70) | 2-propynyl (R)-2-(methanesulfonyloxy)propionate | 3 | 79 | 85 |
| Example I-4 | 1M LiPF$_6$ EC/FEC/MEC(28/2/70) | 2-propynyl (R)-2-(methanesulfonyloxy)propionate | 1 | 80 | 86 |
| Example I-5 | 1M LiPF$_6$ EC/MEC(3/7) | 2-propynyl (R)-2-(methanesulfonyloxy)propionate | 1 | 77 | 82 |
| Example I-6 | 1M LiPF$_6$ EC/FEC/MEC(28/2/70) | methyl (R)-2-(methanesulfonyloxy)propionate | 1 | 76 | 80 |

TABLE 1-continued

| | Composition of Electrolyte Salt Composition of Nonaqueous Electrolytic Solution (ratio by volume of solvents) | Compound | Amount Added (content in nonaqueous electrolytic solution) (wt %) | 0° C. Discharge Capacity Retention Rate after 50 cycles (%) | 60° C. Discharge Capacity Retention Rate after 100 cycles (%) |
|---|---|---|---|---|---|
| Example I-7 | 1M LiPF$_6$ EC/VC/FEC/MEC/DMC (28/1/1/40/30) | 2-propynyl (R)-2-(methanesulfonyloxy)propionate | 1 | 82 | 87 |
| Example I-8 | 0.9M LiPF$_6$ + 0.1M LiBF$_4$ EC/FEC/MEC(28/2/70) + 1 wt % ethylene sulfite | 2-propynyl (R)-2-(methanesulfonyloxy)propionate | 1 | 83 | 87 |
| Example I-9 | 1M LiPF$_6$ EC/FEC/MEC(28/2/70) | 2-propynyl (R)-2-(formyloxy)propionate | 1 | 79 | 84 |
| Example I-10 | 1M LiPF$_6$ EC/FEC/MEC(28/2/70) | 2-propynyl (R)-2-(acetyloxy)propionate | 1 | 76 | 81 |
| Example I-11 | 1M LiPF$_6$ EC/FEC/MEC(28/2/70) | 2-propynyl (R)-2-(methoxycarbonyloxy)propionate | 1 | 78 | 84 |
| Example I-12 | 1M LiPF$_6$ EC/FEC/MEC(28/2/70) | methyl (R)-2-(2-propynyloxycarbonyloxy)propionate | 1 | 79 | 85 |
| Example I-13 | 1M LiPF$_6$ EC/FEC/MEC(28/2/70) | 2-propynyl (R)-2-(dimethoxyphosphoryloxy)propionate | 1 | 76 | 81 |
| Example I-14 | 1M LiPF$_6$ EC/FEC/MEC(28/2/70) | dimethyl (2R,3R)-(+)-2,3-di(methanesulfonyloxy)succinate | 1 | 82 | 85 |
| Example I-15 | 1M LiPF$_6$ EC/FEC/MEC(28/2/70) | 2-propynyl (R)-2-(4-methylbenzenesulfonyloxy)propionate | 1 | 81 | 87 |
| Comparative Example I-1 | 1M LiPF$_6$ EC/MEC(3/7) | none | — | 62 | 65 |
| Comparative Example I-2 | 1M LiPF$_6$ EC/MEC(3/7) | dimethyl malonate | 1 | 65 | 62 |

Example I-16, Comparative Example I-3

A negative electrode sheet was produced, using silicon (negative electrode active material) in place of the negative electrode active material used in Example I-5 and Comparative Example I-1. Precisely, 80% by mass of silicon and 15% by mass of acetylene black (electroconductive agent) were mixed, and added to and mixed in a solution previously prepared by dissolving 5% by mass of polyvinylidene fluoride (binder) in 1-methyl-2-pyrrolidone, thereby preparing a negative electrode mixture paste. The negative electrode mixture paste was applied onto a copper foil (collector), dried, processed under pressure, and blanked into a predetermined size, thereby producing a negative electrode sheet. Coin batteries were produced and evaluated in the same manner as in Example I-5 and Comparative Example I-1, except that the negative electrode sheet produced herein was used. The results are shown in Table 2.

Example I-17, Comparative Example I-4

A positive electrode sheet was produced by changing the positive electrode active material used in Example I-5 and Comparative Example I-1 to LiFePO$_4$ (positive electrode active material). Concretely, 90% by mass of LiFePO$_4$ and 5% by mass of acetylene black (electroconductive agent) were mixed, and added to and mixed in a solution previously prepared by dissolving 5% by mass of polyvinylidene fluoride (binder) in 1-methyl-2-pyrrolidone, thereby preparing a positive electrode mixture paste. The positive electrode mixture paste was applied onto an aluminium foil (collector), dried, processed under pressure and blanked into a predetermined size, thereby producing a positive electrode sheet. Coin batteries were produced and evaluated in the same manner as in Example I-5 and Comparative Example I-1, except that the positive electrode sheet thus produced herein was used and that the charging final voltage was changed to 3.6 V and the discharging final voltage was changed to 2.0 V. The results are shown in Table 3.

TABLE 2

| | Composition of Electrolyte Salt Composition of Nonaqueous Electrolytic Solution (ratio by volume of solvents) | Compound | Amount Added (content in nonaqueous electrolytic solution) (wt %) | 0° C. Discharge Capacity Retention Rate after 50 cycles (%) | 60° C. Discharge Capacity Retention Rate after 100 cycles (%) |
|---|---|---|---|---|---|
| Example I-16 | 1M LiPF$_6$ EC/MEC(3/7) | 2-propynyl (R)-2-(methanesulfonyloxy)propionate | 1 | 71 | 60 |
| Comparative Example I-3 | 1M LiPF$_6$ EC/MEC(3/7) | none | — | 59 | 32 |

TABLE 3

| Composition of Electrolyte Salt Composition of Nonaqueous Electrolytic Solution (ratio by volume of solvents) | Compound | Amount Added (content in nonaqueous electrolytic solution) (wt %) | 0° C. Discharge Capacity Retention Rate after 50 cycles (%) | 60° C. Discharge Capacity Retention Rate after 100 cycles (%) |
|---|---|---|---|---|
| Example I-17 | 1M LiPF$_6$ EC/MEC(3/7) | 2-propynyl (R)-2-(methanesulfonyloxy)propionate | 1 | 81 | 83 |
| Comparative Example I-4 | 1M LiPF$_6$ EC/MEC(3/7) | none | — | 64 | 70 |

The lithium secondary batteries of Examples I-1 to I-15 were all remarkably bettered in point of the low-temperature and high-temperature cycle properties thereof, as compared with the lithium secondary battery of Comparative Example I-1 in which the hydroxy acid derivative of the present invention was not added, and the lithium secondary battery of Comparative Example I-2 in which dimethyl malonate having the same two substituents (alkoxycarbonyl groups) bonded to each other via a hydrocarbon group was added. It has been known that the compounds having a structure where two different substituents of any substituent selected from an alkyloxycarbonyl group, an alkenyloxycarbonyl group and an alkynyloxycarbonyl group, and any substituent selected from a sulfonyloxy group, an acyloxy group, an alkyloxycarbonyloxy group, an alkenyloxycarbonyloxy group, an alkynyloxycarbonyloxy group, a formyloxy group, a dialkylphosphoryl group, an alkyl(alkoxy)phosphoryl group and a dialkoxyphosphoryl group are bonded to each other via a hydrocarbon group therebetween bring about an unexpected specific effect.

In addition, from comparison between Example I-16 and Comparative Example I-3, and from comparison between Example I-17 and Comparative Example I-4, the same effect is seen in the case where a lithium-containing olivine-type iron phosphate was used as the positive electrode, and in the case where Si was used as the negative electrode. Accordingly, it is obvious that the effect of the present invention does not depend on any specific positive electrode or negative electrode.

In addition, it has been confirmed that the lithium primary battery using a nonaqueous electrolytic solution that contains the hydroxy acid derivative compound in Examples I-1 to I-16 is excellent in the low-temperature and high-temperature discharge performance after long-term storage.

Synthesis Example II-1

Synthesis of 2-propenyl 2-(trimethylsilyloxy)propionate 52.99 g (0.50 mol) of an aqueous solution of 85% 2-hydroxypropionic acid and 45 mL of toluene were dissolved in 84.09 g (1.50 mol) of propargyl alcohol, and 1.0 mL of concentrated sulfuric acid was added thereto. Using a Dean-Stark device under normal pressure, the formed water was removed from the system, and this was further reacted under reflux under normal pressure. After 3 hours, the reaction liquid was analyzed through liquid chromatography, and the disappearance of the starting materials was confirmed. Then, the reaction liquid was neutralized with sodium acetate added thereto, filtered, and the filtrate was concentrated. The residue was purified through reduced pressure distillation to give 28.81 g (45% yield) of 2-propynyl 2-hydroxypropionate.

7.69 g (60 mmol) of 2-propenyl 2-hydroxypropionate and 7.29 g (72 mmol) of triethylamine were dissolved in 130 ml of toluene, and 7.17 g (66 mmol) of trimethylsilyl chloride was dropwise added thereto at 5 to 10° C., taking 10 minutes. This was reacted at room temperature for 4 hours, the reaction liquid was washed twice with water, and the organic layer was separated and concentrated. The concentrate was purified through reduced pressure distillation to give 6.24 g (yield 52%) of 2-propenyl 2-(trimethylsilyloxy)propionate.

The structure of the obtained 2-propenyl 2-(trimethylsilyloxy)propionate was identified through $^1$H-NMR, $^{13}$C-NMR and mass spectrometry. The results are shown below.

(1) $^1$H-NMR (300 MHz, CDCl$_3$): 4.67-4.78 (m, 2H), 4.36 (q, J=6.8 Hz, 1H), 2.47-2.49 (m, 1H), 1.43 (d, J=6.8 Hz, 3H), 0.15 (s, 9H).

(2) $^{13}$C-NMR (75 MHz, CDCl$_3$): δ=173.3, 77.5, 75.2, 68.0, 52.4, 21.4, 0.00.

(3) mass spectrometry: MS (CI) [M+1]=201.

Examples II-1 to II-19, Comparative Examples II-1 to II-2

Production of Lithium Ion Secondary Battery

94% by mass of LiNi$_{1/3}$Mn$_{1/3}$Co$_{1/3}$O$_2$ (positive electrode active material) and 3% by mass of acetylene black (electro-conductive agent) were mixed, and added to and mixed in a solution previously prepared by dissolving 3% by mass of polyvinylidene fluoride (binder) in 1-methyl-2-pyrrolidone, thereby preparing a positive electrode mixture paste. The positive electrode mixture paste was applied on one surface of an aluminium foil (collector), then dried, processed under pressure and blanked into a predetermined size, thereby producing a positive electrode sheet. The density of the part of the positive electrode except the collector was 3.6 g/cm$^3$. On the other hand, 95% by mass of artificial graphite (d$_{002}$=0.335 nm, negative electrode active material) coated with low-crystalline carbon was added to and mixed in a solution previously prepared by dissolving 5% by mass of polyvinylidene fluoride (binder) in 1-methyl-2-pyrrolidone, thereby preparing a negative electrode mixture paste. The negative electrode mixture paste was applied onto one surface of a copper foil (collector), dried, processed under pressure and blanked into a predetermined size, thereby producing a negative electrode sheet. The density of the part of the negative electrode except the collector was 1.7 g/cm³. The positive electrode sheet, a porous polyethylene film separator and the negative electrode sheet were laminated in that order, and a nonaqueous electrolytic solution having the composition shown in Table 1 was added thereto to construct a 2032-type coin battery.

[Evaluation of Low-Temperature Properties after High-Temperature Cycle Test]

(Initial Discharge Capacity)

In a thermostatic chamber kept at 25° C., the coin battery fabricated according to the above-mentioned method was charged up to a final voltage of 4.2 V for 3 hours with a constant current of 1 C and under a constant voltage, then the temperature of the thermostatic chamber was lowered to 0° C., and the battery was discharged under a constant current of 1 C to a final voltage of 2.75 V. The initial discharge capacity at 0° C. was measured.

(High-Temperature Cycle Test)

Next, in a thermostatic chamber at 60° C., the coin battery was charged up to a final voltage of 4.2 V for 3 hours with a constant current of 1 C and under a constant voltage, and then discharged under a constant current of 1 C to a final voltage of 2.75 V. This is one cycle. The process was repeated for a total of 100 cycles.

(Discharge Capacity after High-Temperature Cycles)

Further after that, the discharge capacity at 0° C. after the high-temperature cycles was measured in the same manner as that for the measurement of the initial discharge capacity.

(Low-Temperature Properties after High-Temperature Cycle Test)

The low-temperature properties after the high-temperature cycles were determined based on the 0° C. discharge capacity retention rate mentioned below.

0° C. Discharge Capacity Retention Rate after high-temperature cycles(%)=(discharge capacity at 0° C. after high-temperature cycles/initial discharge capacity at 0° C.)×100.

The condition in producing the batteries and the battery characteristics are shown in Table 4.

TABLE 4

| | Composition of Electrolyte Salt Composition of Nonaqueous Electrolytic Solution (ratio by volume of solvents) | Compound | Amount Added (content in nonaqueous electrolytic solution) (wt %) | 0° C. Discharge Capacity Retention Rate after high-temperature cycles (%) |
|---|---|---|---|---|
| Example II-1 | 1M LiPF6 EC/MEC/DMC(30/35/35) | methyl 2-(trimethylsilyloxy)propionate | 0.1 | 68 |
| Example II-2 | 1M LiPF6 EC/MEC/DMC(30/35/35) | methyl 2-(trimethylsilyloxy)propionate | 1 | 73 |
| Example II-3 | 1M LiPF6 EC/MEC/DMC(30/35/35) | methyl 2-(trimethylsilyloxy)propionate | 4 | 72 |
| Example II-4 | 1M LiPF6 EC/MEC/DMC(30/35/35) | methyl 2-(trimethylsilyloxy)propionate | 7 | 70 |
| Example II-5 | 1M LiPF6 EC/MEC/DMC(30/35/35) | 2-propenyl 2-(trimethylsilyloxy)propionate | 1 | 75 |
| Example II-6 | 1M LiPF6 EC/MEC/DMC(30/35/35) | 2-propenyl 2-(trimethylsilyloxy)propionate | 1 | 78 |
| Example II-7 | 1M LiPF6 EC/MEC/DMC(30/35/35) | methyl trimethylsilyloxyacetate | 1 | 71 |
| Example II-8 | 1M LiPF6 EC/MEC/DMC(30/35/35) | methyl 2-methyl-2-(trimethylsilyloxy)propionate | 1 | 74 |
| Example II-9 | 1M LiPF6 EC/MEC/DMC(30/35/35) | dimethyl 2,3-di(trimethylsilyloxy)succinate | 1 | 76 |
| Example II-10 | 1M LiPF6 EC/MEC/DMC(30/35/35) | trimethylsilyl methoxyacetate | 1 | 72 |
| Example II-11 | 1M LiPF6 EC/MEC/DMC(30/35/35) | trimethylsilyl methoxycarbonyloxyacetate | 1 | 74 |
| Example II-12 | 1M LiPF6 EC/MEC/DMC(30/35/35) | trimethylsilyl 2-propynyloxycarbonyloxyacetate | 1 | 75 |
| Example II-13 | 1M LiPF6 EC/MEC/DMC(30/35/35) | trimethylsilyl formyloxyacetate | 1 | 76 |
| Example II-14 | 1M LiPF6 EC/MEC/DMC(30/35/35) | trimethylsilyl acetyloxyacetate | 1 | 77 |
| Example II-15 | 1M LiPF6 EC/MEC/DMC(30/35/35) | trimethylsilyl dimethoxyphosphoryloxyacetate | 1 | 76 |
| Example II-16 | 1M LiPF6 EC/MEC/DMC(30/35/35) | trimethylsilyl 2-(methanesulfonyloxy)propionate | 1 | 78 |
| Example II-17 | 0.95M LiPF6 + 0.05M LiN(SO2CF3)2 EC/VC/MEC/DMC(23/2/50/25) + 2-propynyl methanesulfonate: 1 wt % | methyl 2-(trimethylsilyloxy)propionate | 1 | 80 |
| Example II-18 | 1M LiPF6 EC/MEC/DMC(30/35/35) | trimethylsilyl 2-(4-methylbenzenesulfonyloxy)propionate | 1 | 79 |
| Example II-19 | 1M LiPF6 EC/VC/DFEC/MEC/DMC (22/2/1/50/25) | methyl 2-(trimethylsilyloxy)propionate | 1 | 79 |
| Comparative Example II-1 | 1M LiPF6 EC/MEC/DMC(30/35/35) | none | — | 52 |
| Comparative Example II-2 | 1M LiPF6 EC/MEC/DMC(30/35/35) | trimethylsilyl trimethylsilyloxyacetate | 1 | 51 |

Example II-20, Comparative Example II-3

A negative electrode sheet was produced, using Si (negative electrode active material) in place of the negative electrode active material used in Example II-2 and Comparative Example II-1. Precisely, 80% by mass of Si and 15% by mass of acetylene black (electroconductive agent) were mixed, and added to and mixed in a solution previously prepared by dissolving 5% by mass of polyvinylidene fluoride (binder) in 1-methyl-2-pyrrolidone, thereby preparing a negative electrode mixture paste. The negative electrode mixture paste was applied onto a copper foil (collector), dried, processed under pressure, and blanked into a predetermined size, thereby producing a negative electrode sheet. Coin batteries were produced and evaluated in the same manner as in Example II-2 and Comparative Example II-1, except that the negative electrode sheet produced herein was used. The results are shown in Table 5.

properties after high-temperature cycles, as compared with the lithium secondary battery of Comparative Example II-1 to which the hydroxy acid derivative compound of the present invention was not added, and the lithium secondary battery of Comparative Example II-2 to which was added trimethylsilyl trimethylsilyloxyacetate where the hydrogen atoms of both the hydroxyl group and the carboxyl group of the hydroxy acid were substituted with an alkylsilyl group. It has been known that use of the nonaqueous electrolytic solution, which contains a hydroxy acid derivative compound where any one hydrogen atom alone of the hydroxyl group or the carboxyl group of the hydroxy acid is substituted with a silyloxy group and the other is substituted with a specific substituent, brings about an unexpected specific effect.

In addition, from comparison between Example II-20 and Comparative Example II-3, and from comparison between Example II-21 and Comparative Example II-4, the same effect is seen in the case where a lithium-containing olivine-

TABLE 5

| | Composition of Electrolyte Salt Composition of Nonaqueous Electrolytic Solution (ratio by volume of solvents) | Compound | Amount Added (content in nonaqueous electrolytic solution) (wt %) | 0° C. Discharge Capacity Retention Rate after high-temperature cycles (%) |
|---|---|---|---|---|
| Example II-20 | 1M LiPF6 EC/MEC/DMC(30/35/35) | methyl 2-(trimethylsilyloxy)propionate | 1 | 55 |
| Comparative Example II-3 | 1M LiPF6 EC/MEC/DMC(30/35/35) | none | — | 10 |

Example II-21, Comparative Example II-4

A positive electrode sheet was produced by changing the positive electrode active material used in Example II-2 and Comparative Example II-1 to LiFePO$_4$ (positive electrode active material). Concretely, 90% by mass of LiFePO$_4$ and 5% by mass of acetylene black (electroconductive agent) were mixed, and added to and mixed in a solution previously prepared by dissolving 5% by mass of polyvinylidene fluoride (binder) in 1-methyl-2-pyrrolidone, thereby preparing a positive electrode mixture paste. The positive electrode mixture paste was applied onto an aluminium foil (collector), dried, processed under pressure and blanked into a predetermined size, thereby producing a positive electrode sheet. Coin batteries were produced and evaluated in the same manner as in Example II-2 and Comparative Example II-1, except that the positive electrode sheet thus produced herein was used and that the charging final voltage was changed to 3.6 V and the discharging final voltage was changed to 2.0 V. The results are shown in Table 6.

type iron phosphate was used as the positive electrode, and in the case where Si was used as the negative electrode. Accordingly, it is obvious that the effect of the present invention does not depend on any specific positive electrode or negative electrode.

In addition, it has been confirmed that the lithium primary battery using a nonaqueous electrolytic solution that contains the hydroxy acid derivative compound in Examples II-1 to II-21 is excellent in the low-temperature and high-temperature discharge performance after long-term storage.

Synthesis Example III-1

Synthesis of 2-propynyl 5-cyanovalerate 7.5 g (154 mmol) of sodium cyanide was added to 80 mL of dimethyl sulfoxide, and dissolved therein under heat at 90° C. 25.0 g (128 mmol) of methyl 5-bromovalerate was dropwise added to the solution at an inner temperature of 130° C. or lower, and stirred at 100° C. for 2 hours. After cooled to room

TABLE 6

| | Composition of Electrolyte Salt Composition of Nonaqueous Electrolytic Solution (ratio by volume of solvents) | Compound | Amount Added (content in nonaqueous electrolytic solution) (wt %) | 0° C. Discharge Capacity Retention Rate after high-temperature cycles (%) |
|---|---|---|---|---|
| Example II-21 | 1M LiPF6 EC/MEC/DMC(30/35/35) | methyl 2-(trimethylsilyloxy)propionate | 1 | 84 |
| Comparative Example II-4 | 1M LiPF6 EC/MEC/DMC(30/35/35) | none | — | 61 |

The lithium secondary batteries of Examples II-1 to II-19 were all remarkably bettered in point of the low-temperature temperature, 50 mL of water was added to this, which was then extracted with 60 mL of ethyl acetate. The organic layer was dried with magnesium sulfate, and the solvent was evaporated away under reduced pressure to give 18.0 g (yield 99%) of methyl 5-cyanovalerate.

15.1 g (269 mmol) of propargyl alcohol and 1.92 g (7 mmol) of titanium tetraisopropoxide were added to 18.0 g of the obtained methyl 5-cyanovalerate, and heated and stirred at 120° C. for 8 hours while methanol was removed. After the reaction, methanol and excessive propargyl alcohol were evaporated away under reduced pressure, and the residue was purified through column chromatography (Wakogel C-200, elution with hexane/ethyl acetate=1/9) to give 16.7 g (yield 75%) of 2-propynyl 5-cyanovalerate.

The structure of the obtained 2-propynyl 5-cyanovalerate was identified through $^1$H-NMR. The results are shown below.

(1) $^1$H-NMR (300 MHz, CDCl$_3$): δ=4.69 (d, J=2.69 Hz, 2H), 2.69 (t, J=2.44 Hz, 1H), 2.45-2.35 (m, 4H), 1.84-1.72 (m, 4H).

Synthesis Example III-2

Synthesis of (2-cyanoethyl)(2-propynyl)succinate 5.00 g (50 mmol) of succinic anhydride, 3.55 g (50 mmol) of ethylene cyanohydrin and 61 mg (0.5 mmol) of N,N-dimethylaminopyridine were dissolved in 40 mL of toluene, and heated under reflux for 10 hours. After the reaction, the reaction liquid was concentrated under reduced pressure to give 8.71 g of 4-(2-cyanoethoxy)-4-oxobutanoic acid as a mixture.

8.71 g of the obtained 4-(2-cyanoethoxy)-4-oxobutanoic acid mixture and 11.35 g (55 mmol) of N,N'-dicyclohexylcarbodiimide (DCC) were dissolved in 100 mL of methylene chloride, then 4.20 g (75 mmol) of propargyl alcohol was added thereto and stirred at room temperature for 6 hours. After the reaction, 100 mL of acetone was added to the reaction liquid, which was filtered, and the filtrate was concentrated under reduced pressure. 100 mL of ethyl acetate was added to the concentrate, which was washed with 40 ml of aqueous saturated sodium hydrogencarbonate solution and then with 40 ml of saturated saline water. The organic layer was dried with magnesium sulfate, and concentrated under reduced pressure. The residue was purified through column chromatography (Wakogel C-200, elution with hexane/ethyl acetate=3/1) to give 6.49 g (yield 620) of the intended (2-cyanoethyl)(2-propynyl)succinate.

The structure of the obtained (2-cyanoethyl)(2-propynyl)succinate was identified through $^1$H-NMR. The results are shown below.

(1) $^1$H-NMR (300 MHz, CDCl$_3$): δ=4.71 (d, J=2.44 Hz, 2H), 4.32 (t, J=6.35 Hz, 2H), 2.72 (t, J=6.35 Hz, 2H), 2.65-2.77 (m, 4H), 2.50 (t, J=2.44 Hz, 1H).

Examples III-1 to III-12, Comparative Examples III-1 to III-2

Production of Lithium Ion Secondary Battery

94% by mass of LiNi$_{1/3}$Mn$_{1/3}$Co$_{1/3}$O$_2$ and 3% by mass of acetylene black (electroconductive agent) were mixed, and added to and mixed in a solution previously prepared by dissolving 3% by mass of polyvinylidene fluoride (binder) in 1-methyl-2-pyrrolidone, thereby preparing a positive electrode mixture paste. The positive electrode mixture paste was applied on one surface of an aluminium foil (collector), then dried, processed under pressure and blanked into a predetermined size, thereby producing a positive electrode sheet. The density of the part of the positive electrode except the collector was 3.6 g/cm$^3$. On the other hand, 95% by mass of artificial graphite (d$_{002}$=0.335 nm, negative electrode active material) was added to and mixed in a solution previously prepared by dissolving 5% by mass of polyvinylidene fluoride (binder) in 1-methyl-2-pyrrolidone, thereby preparing a negative electrode mixture paste. The negative electrode mixture paste was applied onto one surface of a copper foil (collector), dried, processed under pressure and blanked into a predetermined size, thereby producing a negative electrode sheet. The density of the part of the negative electrode except the collector was 1.5 g/cm$^3$. Analyzed through X-ray diffractometry, I(110)/I(004) of the electrode sheet was 0.1. The positive electrode sheet, a porous polyethylene film separator and the negative electrode sheet were laminated in that order, and a nonaqueous electrolytic solution having the composition shown in Table 7 was added thereto to construct a 2032-type coin battery.

[Evaluation of Low-Temperature Cycle Properties]

In a thermostatic chamber kept at 25° C., the coin battery fabricated according to the above-mentioned method was charged up to a final voltage 4.2 V for 3 hours with a constant current of 1 C and under a constant voltage, and thereafter discharged under a constant current of 1 C to a final voltage of 2.75 V. This is a precycle.

Next, in a thermostatic chamber at 0° C., this was charged up to 4.2 V for 3 hours with a constant current of C and under a constant voltage, and thereafter discharged under a constant current of 1 C to a final voltage of 2.75 V. The cycle was repeated up to 50 cycles. According to the formula mentioned below, the discharge capacity retention rate after 50 cycles was calculated.

Discharge Capacity Retention Rate(%)=[(discharge capacity after 50 cycles/discharge capacity after 1 cycle)×100.

The condition in producing the batteries and the battery characteristics are shown in Table 7.

TABLE 7

| | Composition of Electrolyte Salt Composition of Nonaqueous Electrolytic Solution (ratio by volume of solvents) | Added Amount of Carboxylate (content in nonaqueous electrolytic solution) (wt %) | Added Amount of Second Additive (content in nonaqueous electrolytic solution) (wt %) | Discharge Capacity Retention Rate (%) |
|---|---|---|---|---|
| Example III-1 | 1M LiPF6 FEC/EC/MEC/DMC(20/10/40/30) | di(2-propynyl) 2-methylsuccinate (0.05) | — | 75 |
| Example III-2 | 1M LiPF6 FEC/EC/MEC/DMC(20/10/40/30) | di(2-propynyl) 2-methylsuccinate (0.5) | — | 78 |
| Example III-3 | 1M LiPF6 FEC/EC/MEC/DMC(20/10/40/30) | di(2-propynyl) 2-methylsuccinate (4) | — | 76 |

TABLE 7-continued

| | Composition of Electrolyte Salt Composition of Nonaqueous Electrolytic Solution (ratio by volume of solvents) | Added Amount of Carboxylate (content in nonaqueous electrolytic solution) (wt %) | Added Amount of Second Additive (content in nonaqueous electrolytic solution) (wt %) | Discharge Capacity Retention Rate (%) |
|---|---|---|---|---|
| Example III-4 | 1M LiPF6 FEC/EC/MEC/DMC(20/10/40/30) | di(2-propynyl) adipate (0.5) | — | 77 |
| Example III-5 | 1M LiPF6 FEC/EC/MEC/DMC(20/10/40/30) | 2-propynyl 5-cyanovalerate (0.5) | — | 80 |
| Example III-6 | 1M LiPF6 FEC/EC/MEC/DMC(20/10/40/30) | 2-propynyl 3-cyanopropionate (0.5) | — | 76 |
| Example III-7 | 1M LiPF6 FEC/EC/MEC/DMC(20/10/40/30) | di(2-propynyl) succinate (0.5) | — | 76 |
| Example III-8 | 1M LiPF6 FEC/EC/MEC/DMC(20/10/40/30) | (2-cyanoethyl)(2-propynyl) succinate (0.5) | — | 81 |
| Example III-9 | 1M LiPF6 FEC/EC/MEC/DMC(20/10/40/30) | di(2-cyanoethyl) succinate (0.5) | — | 74 |
| Example III-10 | 1M LiPF6 FEC/EC/MEC/DMC(20/10/40/30) | methyl(2-propynyl) succinate (0.5) | — | 73 |
| Example III-11 | 1M LiPF6 FEC/EC/MEC/DMC(20/10/40/30) | (2-cyanoethyl)methyl succinate (0.5) | — | 71 |
| Example III-12 | 1M LiPF6 FEC/PC/EC/MEC/DMC (15/5/10/40/30) | di(2-propynyl) 2-methylsuccinate (0.5) | 1,5-pentanediol dimethanesulfonate (1) | 85 |
| Comparative Example III-1 | 1M LiPF6 FEC/EC/MEC/DMC(20/10/40/30) | — | — | 64 |
| Comparative Example III-2 | 1M LiPF6 FEC/EC/MEC/DMC(20/10/40/30) | 2-propynyl valerate (0.5) | — | 62 |

Example III-13, Comparative Example III-3

A negative electrode sheet was produced, using Si (negative electrode active material) in place of the negative electrode active material used in Example III-2 and Comparative Example III-1. Precisely, 80% by mass of Si and 15% by mass of acetylene black (electroconductive agent) were mixed, and added to and mixed in a solution previously prepared by dissolving 5% by mass of polyvinylidene fluoride (binder) in 1-methyl-2-pyrrolidone, thereby preparing a negative electrode mixture paste. The negative electrode mixture paste was applied onto a copper foil (collector), dried, processed under pressure, and blanked into a predetermined size, thereby producing a negative electrode sheet. Coin batteries were produced and evaluated in the same manner as in Example III-2 and Comparative Example III-1, except that the negative electrode sheet produced herein was used. The results are shown in Table 8.

Example III-14, Comparative Example III-4

A positive electrode sheet was produced by changing the positive electrode active material used in Example III-2 and Comparative Example III-1 to LiFePO$_4$ (positive electrode active material) coated with amorphous carbon. Concretely, 90% by mass of LiFePO$_4$ coated with amorphous carbon and 5% by mass of acetylene black (electroconductive agent) were mixed, and added to and mixed in a solution previously prepared by dissolving 5% by mass of polyvinylidene fluoride (binder) in 1-methyl-2-pyrrolidone, thereby preparing a positive electrode mixture paste. The positive electrode mixture paste was applied onto an aluminium foil (collector), dried, processed under pressure and blanked into a predetermined size, thereby producing a positive electrode sheet. Coin batteries were produced and evaluated in the same manner as in Example III-2 and Comparative Example III-1, except that the positive electrode sheet thus produced herein was used and that the charging final voltage was changed to 3.6 V and the discharging final voltage was changed to 2.0 V. The results are shown in Table 9.

TABLE 8

| | Composition of Electrolyte Salt Composition of Nonaqueous Electrolytic Solution (ratio by volume of solvents) | Added Amount of Carboxylate (content in nonaqueous electrolytic solution) (wt %) | Discharge Capacity Retention Rate (%) |
|---|---|---|---|
| Example III-13 | 1M LiPF$_6$ FEC/EC/MEC/DMC(20/10/40/30) | di(2-propynyl) 2-methylsuccinate (0.5) | 60 |
| Comparative Example III-3 | 1M LiPF$_6$ FEC/EC/MEC/DMC(20/10/40/30) | — | 46 |

TABLE 9

| | Composition of Electrolyte Salt Composition of Nonaqueous Electrolytic Solution (ratio by volume of solvents) | Added Amount of Carboxylate (content in nonaqueous electrolytic solution) (wt %) | Discharge Capacity Retention Rate (%) |
|---|---|---|---|
| Example III-14 | 1M LiPF$_6$ FEC/EC/MEC/DMC(20/10/40/30) | di(2-propynyl) 2-methylsuccinate (0.5) | 82 |
| Comparative Example III-4 | 1M LiPF$_6$ FEC/EC/MEC/DMC(20/10/40/30) | — | 64 |

The lithium secondary batteries of Examples III-1 to III-12 were all remarkably bettered in point of the low-temperature cycle properties, as compared with the lithium secondary battery of Comparative Example III-1 to which no additive was added, and the lithium secondary battery of Comparative Example III-2 to which was added a carboxylate where the alcohol moiety of the ester group of the carboxylate had a carbon-carbon triple bond (ethynyl group), but any of an ester, an ethynyl group or a cyano group was not bonded to the carbonyl carbon of the carboxylate via an alkylene group. From the above, it has been clarified that the effect of the present invention is specific to the case of adding a carboxylate where the alcohol moiety of the ester group of the carboxylate has a carbon-carbon triple bond (ethynyl group) or a carbon-nitrogen triple bond (cyano group), and any of an ester, an ethynyl group or a cyano group is bonded to the carbonyl carbon of the carboxylate via an alkylene group.

In addition, from comparison between Example III-13 and Comparative Example III-3, and from comparison between Example III-14 and Comparative Example III-4, the same effect is seen in the case where a lithium-containing olivine-type iron phosphate was used as the positive electrode, and in the case where Si was used as the negative electrode. Accordingly, it is obvious that the effect of the present invention does not depend on any specific positive electrode or negative electrode.

Further, the nonaqueous electrolytic solution of Examples III-1 to III-14 has an effect of improving the low-temperature charge characteristics of lithium primary batteries.

Synthesis Example IV-1

Synthesis of di(2-propynyl) 2-(methanesulfonyloxy)succinate 20.00 g (0.149 mol) of 2-hydroxysuccinic acid and 0.2 mL of methanesulfonic acid were dissolved in 100 mL of toluene, 50.16 g (0.895 mol) of propargyl alcohol was added thereto. Using a Dean-Stark device, this was reacted for 4 hours while water formed as a side product was removed under normal pressure. The disappearance of the starting materials was confirmed through gas chromatography, and sodium acetate was added to the system. The resulting salt was filtered away, and the filtrate was concentrated under reduced pressure. The residue was purified through column chromatography (Wakogel C-200, elution with hexane/ethyl acetate=2/1) to give 13.35 g (yield 43%) of di(2-propynyl) 2-hydroxysuccinate.

6.10 g (0.029 mol) of the obtained di(2-propynyl) 2-hydroxysuccinate and 3.32 g (0.029 mol) of methanesulfonyl chloride were added to 40 g of ethyl acetate, and 2.93 g (0.029 mol) of triethylamine was dropwise added thereto within a range of from 5° C. to 15° C., taking 15 minutes. This was reacted at room temperature for 1 hour, the disappearance of the starting materials was confirmed through gas chromatography, and 20 ml of water was added for liquid-liquid separation. The organic layer was concentrated under reduced pressure. The residue was purified through column chromatography (Wakogel C-200, elution with hexane/ethyl acetate=2/1) to give 4.50 g (yield 54%) of the intended di(2-propynyl) 2-(methanesulfonyloxy)succinate.

The structure of the obtained di(2-propynyl) 2-(methanesulfonyloxy)succinate was identified through $^1$H-NMR. The results are shown below.

(1) $^1$H-NMR (300 MHz, CDCl$_3$): δ=5.43 (dd, J=6.9, 4.9 Hz, 1H), 4.82 (d, J=2.5 Hz, 2H), 4.82 (d, J=2.5 Hz, 2H), 3.20 (s, 3H), 3.08-3.07 (m, 2H), 2.56 (t, J=2.5 Hz, 1H), 2.52 (t, J=2.5 Hz, 1H).

Examples IV-1 to IV-15, Comparative Examples IV-1 to IV-2

Production of Lithium Ion Secondary Battery

93% by mass of LiCoO$_2$ (positive electrode active material) and 3% by mass of acetylene black (electroconductive agent) were mixed, and added to and mixed in a solution previously prepared by dissolving 4% by mass of polyvinylidene fluoride (binder) in 1-methyl-2-pyrrolidone, thereby preparing a positive electrode mixture paste. The positive electrode mixture paste was applied on both surfaces of an aluminium foil (collector), then dried, processed under pressure and cut into a predetermined size, thereby producing a belt-like positive electrode sheet. The density of the part of the positive electrode except the collector was 3.6 g/cm$^3$. On the other hand, 95% by mass of artificial graphite (d$_{002}$=0.335 nm, negative electrode active material) coated with low-crystalline carbon was added to and mixed in a solution previously prepared by dissolving 5% by mass of polyvinylidene fluoride (binder) in 1-methyl-2-pyrrolidone, thereby preparing a negative electrode mixture paste. The negative electrode mixture paste was applied onto both surfaces of a copper foil (collector), dried, processed under pressure and cut into a predetermined size, thereby producing a belt-like negative electrode sheet. The density of the part of the negative electrode except the collector was 1.7 g/cm$^3$. The positive electrode sheet, a porous polyethylene film separator, the negative electrode sheet and the separator were laminated in that order, and the resulting laminate was coiled up. The coil was housed in a nickel-plated, iron-made cylindrical battery can serving also as a negative electrode terminal. Further, a nonaqueous electrolytic solution prepared by adding a predetermined amount of the compound shown in Table 10 was introduced into the can, then the battery cap having a positive electrode terminal was caulked with a gasket, thereby constructing a 18650-type cylindrical battery. In this, the positive electrode terminal was previously interconnected inside the battery, using the positive electrode sheet and an aluminium lead tab, and the negative electrode can was also inside the battery, using the negative electrode sheet and a nickel lead tab.

[Evaluation of Low-Temperature Load Characteristics after High-Temperature Charging Storage]

(Initial Discharge Capacity)

In a thermostatic chamber kept at 25° C., the cylindrical battery fabricated according to the above-mentioned method was charged up to a final voltage of 4.3 V for 3 hours with a constant current of 1 C and under a constant voltage, then the temperature of the thermostatic chamber was lowered to 0° C., and the battery was discharged under a constant current of 1 C to a final voltage of 2.75 V. The initial discharge capacity at 0° C. was measured.

(Low-Temperature Load Characteristics after High-Temperature Charging Storage Test)

The low-temperature load characteristics after high-temperature charging storage were determined based on the 0° C. discharge capacity retention rate mentioned below.

0° C. Discharge Capacity Retention Rate after high-temperature charging storage(%)=[(discharge capacity at 0° C. after high-temperature charging storage/initial discharge capacity at 0° C.)×100.

The condition in producing the batteries and the battery characteristics are shown in Table 10.

TABLE 10

| | Composition of Electrolyte Salt Composition of Nonaqueous Electrolytic Solution (ratio by volume of solvents) | Compound | Added Amount (content in nonaqueous electrolytic solution) (wt %) | 0° C. Discharge Capacity Retention Rate after high-temperature charging storage (%) |
|---|---|---|---|---|
| Example IV-1 | 1M LiPF6 EC/FEC/MEC/DMC(20/10/50/20) | dimethyl 2-(methanesulfonyloxy)succinate | 0.1 | 71 |
| Example IV-2 | 1M LiPF6 EC/FEC/MEC/DMC(20/10/50/20) | dimethyl 2-(methanesulfonyloxy)succinate | 1 | 78 |
| Example IV-3 | 1M LiPF6 EC/FEC/MEC/DMC(20/10/50/20) | dimethyl 2-(methanesulfonyloxy)succinate | 4 | 76 |
| Example IV-4 | 1M LiPF6 EC/FEC/MEC/DMC(20/10/50/20) | dimethyl 2-(methanesulfonyloxy)succinate | 7 | 72 |
| Example IV-5 | 1M LiPF6 EC/FEC/MEC/DMC(20/10/50/20) | di(2-propenyl) 2-(methanesulfonyloxy)succinate | 1 | 79 |
| Example IV-6 | 1M LiPF6 EC/FEC/MEC/DMC(20/10/50/20) | di(2-propenyl) 2-(methanesulfonyloxy)succinate | 1 | 80 |
| Example IV-7 | 1M LiPF6 EC/FEC/MEC/DMC(20/10/50/20) | dimethyl 2-(formyloxy)succinate | 1 | 76 |
| Example IV-8 | 1M LiPF6 EC/FEC/MEC/DMC(20/10/50/20) | dimethyl 2-(dimethoxyphosphoryloxy)succinate | 1 | 77 |
| Example IV-9 | 1M LiPF6 EC/FEC/MEC/DMC(20/10/50/20) | dimethyl 2-(trimethylsilyloxy)succinate | 1 | 73 |
| Example IV-10 | 1M LiPF6 EC/FEC/MEC/DMC(20/10/50/20) | dimethyl 2-methoxysuccinate | 1 | 71 |
| Example IV-11 | 1M LiPF6 EC/FEC/MEC/DMC(20/10/50/20) | trimethyl 1-(methanesulfonyloxy)propane-1,2,3-tricarboxylate | 1 | 77 |
| Example IV-12 | 1M LiPF6 EC/FEC/MEC/DMC(20/10/50/20) | tri(2-propenyl) 2-(methanesulfonyloxy)propane-1,2,3-tricarboxylate | 1 | 79 |
| Example IV-13 | 1M LiPF6 EC/PC/VC/MEC/DMC(23/5/2/35/35) | dimethyl 2-(methanesulfonyloxy)succinate | 1 | 77 |
| Example IV-14 | 1M LiPF6 EC/VC/FEC/MEC/DMC(10/1/14/50/25) | dimethyl 2-(methanesulfonyloxy)succinate | 1 | 82 |
| Example IV-15 | 1M LiPF6 EC/FEC/MEC/DMC(20/10/50/20) | dimethyl 2-(4-methylbenzenesulfonyloxy)succinate | 1 | 79 |
| Comparative Example IV-1 | 1M LiPF6 EC/FEC/MEC/DMC(20/10/50/20) | none | — | 59 |
| Comparative Example IV-2 | 1M LiPF6 EC/FEC/MEC/DMC(20/10/50/20) | dimethyl succinate | 1 | 58 |

(High-Temperature Charging Storage Test)

Next, in a thermostatic chamber at 60° C., the cylindrical battery was charged up to a final voltage of 4.3 V for 3 hours with a constant current of 1 C and under a constant voltage, and then, while kept at 4.3 V, this was stored for 3 days. Afterwards, the battery was put into a thermostatic chamber at 25° C., and then once discharged to a final voltage of 2.75 V under a constant current of 1 C.

(Discharge Capacity after High-Temperature Charging Storage)

Further afterwards, the discharge capacity at 0° C. after high-temperature charging storage of the battery was measured, in the same manner as that for the measurement of the initial discharge capacity thereof.

Example IV-16, Comparative Example IV-3

A negative electrode sheet was produced, using Si (negative electrode active material) in place of the negative electrode active material used in Example IV-2 and Comparative Example IV-1. Precisely, 80% by mass of Si and 15% by mass of acetylene black (electroconductive agent) were mixed, and added to and mixed in a solution previously prepared by dissolving 5% by mass of polyvinylidene fluoride (binder) in 1-methyl-2-pyrrolidone, thereby preparing a negative electrode mixture paste. The negative electrode mixture paste was applied onto a copper foil (collector), dried, processed under pressure, and cut into a predetermined size, thereby producing a belt-like negative electrode sheet. Cylindrical batteries were produced and evaluated in the same manner as in Example IV-2 and Comparative Example IV-1, except that the negative electrode sheet produced herein was used. The results are shown in Table 11.

having a specific functional group quite differing from the carboxylate in the linking group that links these functional groups.

TABLE 11

| | Composition of Electrolyte Salt Composition of Nonaqueous Electrolytic Solution (ratio by volume of solvents) | Compound | Added Amount (content in nonaqueous electrolytic solution) (wt %) | 0° C. Discharge Capacity Retention Rate after high-temperature charging storage (%) |
|---|---|---|---|---|
| Example IV-16 | 1M LiPF6 EC/FEC/MEC/DMC(20/10/50/20) | dimethyl 2-(methanesulfonyloxy)succinate | 1 | 63 |
| Comparative Example IV-3 | 1M LiPF6 EC/FEC/MEC/DMC(20/10/50/20) | none | — | 49 |

Example IV-17, Comparative Example IV-4

A positive electrode sheet was produced by changing the positive electrode active material used in Example IV-2 and Comparative Example IV-1 to $LiFePO_4$ (positive electrode active material) coated with amorphous carbon. Concretely, 90% by mass of $LiFePO_4$ coated with amorphous carbon and 5% by mass of acetylene black (electroconductive agent) were mixed, and added to and mixed in a solution previously prepared by dissolving 5% by mass of polyvinylidene fluoride (binder) in 1-methyl-2-pyrrolidone, thereby preparing a positive electrode mixture paste. The positive electrode mixture paste was applied onto an aluminium foil (collector), dried, processed under pressure and cut into a predetermined size, thereby producing a belt-like positive electrode sheet. Cylindrical batteries were produced and evaluated in the same manner as in Example IV-2 and Comparative Example IV-1, except that the positive electrode sheet thus produced herein was used and that the charging final voltage was changed to 3.6 V and the discharging final voltage was changed to 2.0 V. The results are shown in Table 12.

In addition, from comparison between Example IV-16 and Comparative Example IV-3, and from comparison between Example IV-17 and Comparative Example IV-4, the same effect is seen in the case where a lithium-containing olivine-type iron phosphate was used as the positive electrode, and in the case where Si was used as the negative electrode. Accordingly, it is obvious that the effect of the present invention does not depend on any specific positive electrode or negative electrode.

Further, the nonaqueous electrolytic solution of Examples IV-1 to IV-17 has an effect of improving the low-temperature load characteristics after high-temperature storage of lithium primary batteries.

INDUSTRIAL APPLICABILITY

The electrochemical elements such as lithium batteries using the nonaqueous electrolytic solution of the present invention are excellent in low-temperature and high-temperature cycle properties and can maintain excellent battery performance for a long period of time.

TABLE 12

| | Composition of Electrolyte Salt Composition of Nonaqueous Electrolytic Solution (ratio by volume of solvents) | Compound | Added Amount (content in nonaqueous electrolytic solution) (wt %) | 0° C. Discharge Capacity Retention Rate after high-temperature charging storage (%) |
|---|---|---|---|---|
| Example IV-17 | 1M LiPF6 EC/FEC/MEC/DMC(20/10/50/20) | dimethyl 2-(methanesulfonyloxy)succinate | 1 | 81 |
| Comparative Example IV-4 | 1M LiPF6 EC/FEC/MEC/DMC(20/10/50/20) | none | — | 65 |

The lithium secondary batteries of Examples IV-1 to IV-15 were all remarkably bettered in point of the low-temperature load characteristics after high-temperature charging storage, as compared with the lithium secondary battery of Comparative Example IV-1 to which no additive was added, and the lithium secondary battery of Comparative Example IV-2 to which was added a carboxylic diester containing two carboxylate moieties alone in the molecular structure. From the above, it has been clarified that the effect of the present invention is specific to the compound having at least two carboxylate moieties in the molecular structure and further In addition, the novel hydroxy acid derivative compound and carboxylate compound of the present invention are useful as intermediate materials for medicines, agricultural chemicals, electronic materials, polymer materials and others, or as electrochemical element materials.

When the nonaqueous electrolytic solution of the present invention is used in electrochemical elements to be mounted on hybrid vehicles, plug-in hybrid vehicles, electric vehicles and others, then it exhibits excellent battery performance in high-temperature cycle properties and low-temperature properties after high-temperature cycles.

The invention claimed is:

1. A nonaqueous electrolytic solution of an electrolyte salt dissolved in a nonaqueous solvent, which comprises a carboxylate represented by the following general formula (8) in an amount of from 0.01 to 5% by mass of the nonaqueous electrolytic solution:

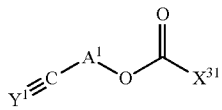

(8)

wherein $X^{31}$ represents $-A^2-C\equiv Y^2$, $-A^2-C(=O)O-A^3-C\equiv Y^2$ or $-A^2-C(=O)O-A^4$; $A^1$, $A^2$ and $A^3$ each independently represent an alkylene group having from 1 to 6 carbon atoms; $A^4$ represents an alkyl group having from 1 to 6 carbon atoms; $Y^1$ and $Y^2$ each independently represent CH or N.

2. The nonaqueous electrolytic solution according to claim 1, wherein the carboxylate represented by the general formula (8) is at least one selected from the group consisting of 2-propynyl 3-butynoate, 2-cyanoethyl 3-butynoate, 2-propynyl 3-cyanopropionate, 2-propynyl 4-cyanobutanoate, 2-propynyl 5-cyanovalerate, 2-cyanoethyl 3-cyanopropionate, 2-cyanoethyl 4-cyanobutanoate, 2-cyanoethyl 5-cyanovalerate, di(2-propynyl) succinate, di(2-propynyl) glutarate, di(2-propynyl) adipate, di(2-propynyl) 2-methylsuccinate, (2-propynyl) (2-cyanoethyl) succinate, di(2-cyanoethyl) succinate, di(2-cyanoethyl) glutarate, di(2-cyanoethyl) adipate, di(2-cyanoethyl) 2-methylsuccinate, (2-propynyl)methyl succinate, (2-cyanoethyl)methyl succinate, and (2-cyanoethyl) ethyl succinate.

3. The nonaqueous electrolytic solution according to claim 2, wherein the nonaqueous solvent comprises at least one selected from the group consisting of:
a cyclic carbonate, a linear carbonate, a linear ester, an ether, an amide, a phosphate, a sulfone, a lactone, a nitrile, a carboxylic acid anhydride, an aromatic compound, and a S=O bond-containing compound,
and wherein the electrolyte salt comprises at least one selected from the group consisting of:
a lithium salt and an onium salt.

4. The nonaqueous electrolytic solution according to claim 2, wherein the carboxylate represented by the general formula (8) is di(2-propynyl) succinate.

5. The nonaqueous electrolytic solution according to claim 1, wherein the nonaqueous solvent comprises a cyclic carbonate and a linear carbonate, and the linear carbonate comprises at least one asymmetric linear carbonate selected from methyl ethyl carbonate, methyl propyl carbonate, methyl isopropyl carbonate, methyl butyl carbonate, and ethyl propyl carbonate.

6. The nonaqueous electrolytic solution according to claim 1, wherein $X^{31}$ represents $-A^2-C\equiv Y^2$.

7. The nonaqueous electrolytic solution according to claim 1, wherein $X^{31}$ represents $-A^2-C(=O)O-A^3-C\equiv Y^2$.

8. The nonaqueous electrolytic solution according to claim 1, wherein $X^{31}$ represents $-A^2-C(=O)O-A^4$.

9. The nonaqueous electrolytic solution according to claim 1, wherein the nonaqueous solvent comprises at least one selected from the group consisting of:
a cyclic carbonate, a linear carbonate, a linear ester, an ether, an amide, a phosphate, a sulfone, a lactone, a nitrile, a carboxylic acid anhydride, an aromatic compound, and a S=O bond-containing compound,
and wherein the electrolyte salt comprises at least selected from the group consisting of:
a lithium salt and an onium salt.

* * * * *